(12) United States Patent
Hill et al.

(10) Patent No.: US 11,214,605 B2
(45) Date of Patent: *Jan. 4, 2022

(54) LIGHT SINGLE-CHAIN FUSION POLYPEPTIDES, ENCODING NUCLEIC ACID MOLECULES AND HOST CELLS

(71) Applicant: APOGENIX AG, Heidelberg (DE)

(72) Inventors: Oliver Hill, Neckarsteinach (DE); Christian Gieffers, Dossenheim (DE); Meinolf Thiemann, Schriesheim (DE)

(73) Assignee: APOGENIX AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/832,183

(22) Filed: Mar. 27, 2020

(65) Prior Publication Data
US 2020/0247860 A1    Aug. 6, 2020

Related U.S. Application Data

(63) Continuation of application No. 16/156,867, filed on Oct. 10, 2018, now Pat. No. 10,640,543, which is a continuation of application No. 15/643,787, filed on Jul. 7, 2017, now Pat. No. 10,118,953, which is a continuation of application No. 15/172,393, filed on Jun. 3, 2016, now Pat. No. 9,725,495, which is a continuation of application No. 14/320,261, filed on Jun. 30, 2014, now Pat. No. 9,359,420, which is a continuation of application No. 13/902,328, filed on May 24, 2013, now Pat. No. 8,921,519, which is a continuation of application No. 13/055,109, filed as application No. PCT/EP2009/059269 on Jul. 18, 2009, now Pat. No. 8,450,460.

(30) Foreign Application Priority Data

Jul. 21, 2008    (EP) .................................... 08013112

(51) Int. Cl.
| | |
|---|---|
| *C12N 15/62* | (2006.01) |
| *C12N 15/79* | (2006.01) |
| *C07K 14/705* | (2006.01) |
| *C07K 14/525* | (2006.01) |
| *C07K 16/00* | (2006.01) |
| *A61K 38/00* | (2006.01) |

(52) U.S. Cl.
CPC ...... *C07K 14/525* (2013.01); *C07K 14/70575* (2013.01); *C07K 14/70578* (2013.01); *C07K 16/00* (2013.01); *C12N 15/62* (2013.01); *C12N 15/79* (2013.01); *A61K 38/00* (2013.01); *C07K 2317/41* (2013.01); *C07K 2317/52* (2013.01); *C07K 2317/55* (2013.01); *C07K 2319/00* (2013.01); *C07K 2319/22* (2013.01); *C07K 2319/30* (2013.01); *C07K 2319/32* (2013.01); *C07K 2319/35* (2013.01); *C07K 2319/74* (2013.01)

(58) Field of Classification Search
CPC .......... C07K 14/70575; C07K 2319/00; C07K 2319/35; C07K 2319/74; C12N 15/62; C12N 15/79
See application file for complete search history.

*Primary Examiner* — Robert S Landsman
(74) *Attorney, Agent, or Firm* — Perkins Coie LLP; Viola T. Kung

(57) ABSTRACT

The present invention refers to single-chain fusion proteins comprising three soluble TNF superfamily (TNFSF) cytokine domains and nucleic acid molecules encoding these fusion proteins. The fusion proteins are substantially non-aggregating and suitable for therapeutic, diagnostic and/or research applications.

11 Claims, 15 Drawing Sheets

Specification includes a Sequence Listing.

9A  9B

A   TNF-SF protein Aggregation

B   TNF-SF protein defined soluble protein

A

```
        Gly281        1.   2.        Arg121
I.           G  G  S  G  N  G  S  G  S  R
II.          G  G  S  G  S  G  N  G  S  R
III.         G  G  S  G  S  G  S  G  S  R
```

B

C

| Protein | Linker-layout |
|---|---|
| scTRAILwt-NSNS | both linkers with Asn in pos-1 |
| scTRAILwt-NSSN | Linker-1 with Asn in pos-1, linker-2 with Asn in pos-2 |
| scTRAILwt-NSSS | Linker-1 with Asn in pos-1, linker-2 with Ser in pos-2 |
| scTRAILwt-SNNS | Linker-1 with Ser in pos-1, linker-2 with Asn in pos-2 |
| scTRAILwt-SNSN | both linkers with Asn in position-2 |

LIGHT SINGLE-CHAIN FUSION POLYPEPTIDES, ENCODING NUCLEIC ACID MOLECULES AND HOST CELLS

This application is a continuation of U.S. application Ser. No. 16/156,867, filed Oct. 10, 2018, now U.S. Pat. No. 10,640,543; which is a continuation of U.S. application Ser. No. 15/643,787, filed Jul. 7, 2017, now U.S. Pat. No. 10,118,953; which is a continuation of U.S. application Ser. No. 15/172,393, filed Jun. 3, 2016, now U.S. Pat. No. 9,725,495; which is a continuation of application Ser. No. 14/320,261, filed Jun. 30, 2014, now U.S. Pat. No. 9,359,420; which is a continuation of U.S. application Ser. No. 13/902,328, filed May 24, 2013, now U.S. Pat. No. 8,921,519; which is a continuation of U.S. application Ser. No. 13/055,109, filed Mar. 10, 2011, now U.S. Pat. No. 8,450,460; which is a National Stage of International Application PCT/EP2009/059269, filed Jul. 18, 2009, published Jan. 28, 2010, under PCT Article 21(2) in English; which claims the priority of EP 08013112.1, filed Jul. 21, 2008. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Oct. 10, 2018, and a size of 150 kilobytes. The Sequence_Listing filed via EFS-Web is part of the specification and is hereby incorporated in its entirety by reference herein.

DESCRIPTION

The present invention refers to single-chain fusion proteins comprising three soluble TNF superfamily (TNFSF) cytokine domains and nucleic acid molecules encoding the fusion proteins. The fusion proteins are substantially non-aggregating and suitable for therapeutic, diagnostic and/or research applications.

STATE OF THE ART

It is known that trimerization of TNFSF cytokines, e.g., the CD95 ligand (CD95L), is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerisation domain usually has a large molecular weight and/or that the trimerisation is rather inefficient.

Schneider et al. (J Exp Med 187 (1989), 1205-1213) describe that trimers of TNF cytokines are stabilised by N-terminally positioned stabilisation motifs. In CD95L, the stabilisation of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilised by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

It was an object of the present invention to provide single-chain fusion proteins comprising at least three TNF cytokine domains which allow efficient recombinant manufacturing combined with good stability concerning aggregation.

SUMMARY OF THE INVENTION

The present invention relates to a single-chain fusion polypeptide comprising:
(i) a first soluble TNF-family cytokine domain,
(ii) a first peptide linker,
(iii) a second soluble TNF-family cytokine domain,
(iv) a second peptide linker, and
(v) a third soluble TNF-family cytokine domain,
which is substantially non-aggregating.

The invention further relates to a nucleic acid molecule encoding a fusion protein as described herein and to a cell or a non-human organism transformed or transfected with a nucleic acid molecule as described herein.

The invention also relates to a pharmaceutical or diagnostic composition comprising as an active agent a fusion protein, a nucleic acid molecule, or a cell as described herein.

The invention also relates to a fusion protein, a nucleic acid molecule, or a cell as described herein for use in therapy, e.g., the use of a fusion protein, a nucleic acid molecule, or a cell as described herein for the preparation of a pharmaceutical composition in the prophylaxis and/or treatment of disorders caused by, associated with and/or accompanied by dysfunction of TNFSF cytokines, particularly proliferative disorders, such as tumours, e.g. solid or lymphatic tumours; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

DESCRIPTION OF THE FIGURES

FIG. 9 9A Single-chain fusion polypeptide comprising an additional Fab antibody fragment.

9B Single-chain fusion polypeptide comprising an additional scFv antibody fragment.

Figure 10:
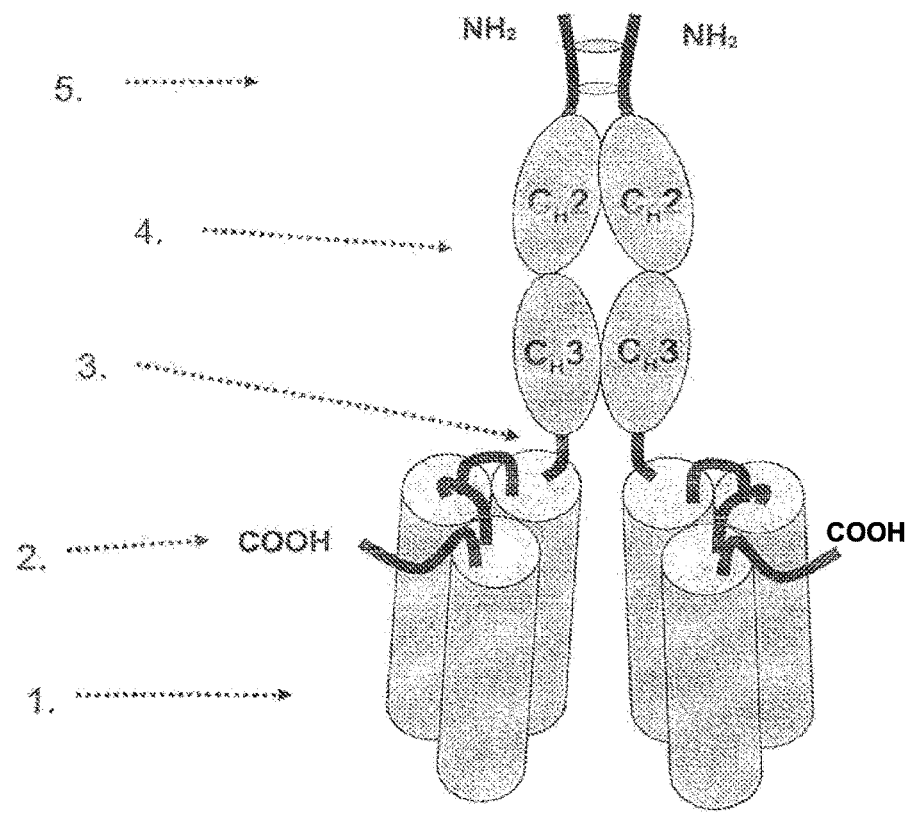

FIG. 10 Dimerization of two N-terminally fused scFc fusion polypeptides via disulfide bridges.

Figure 11:
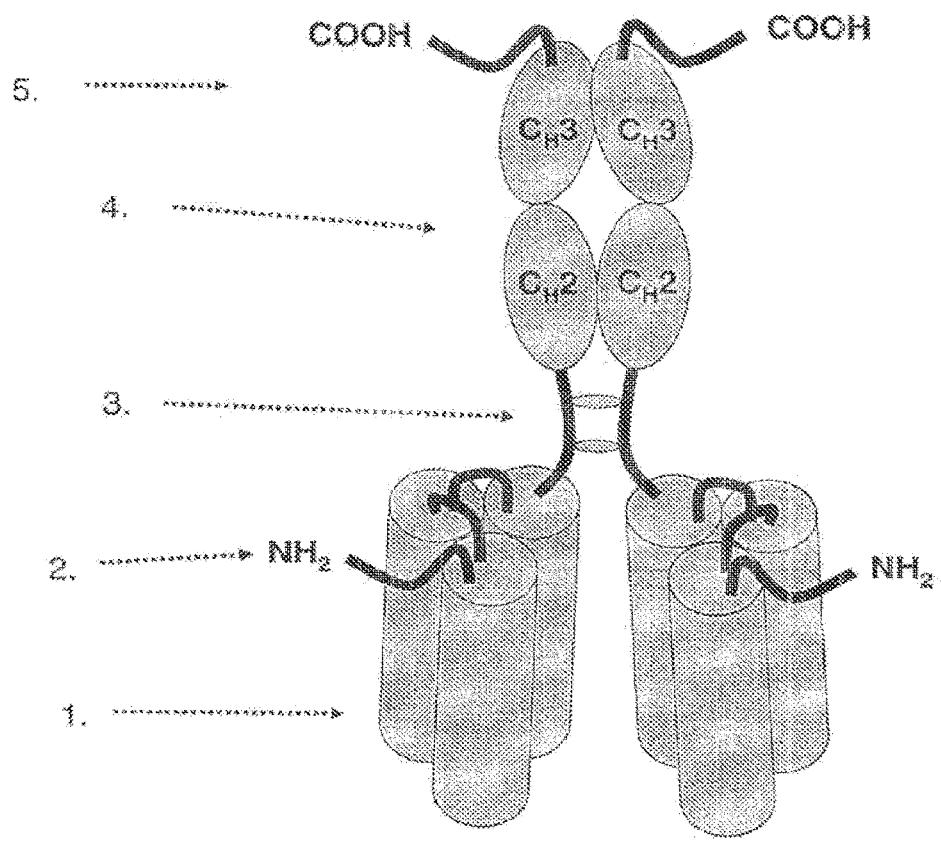

FIG. 11 Dimerization of two C-terminally fused scFc fusion polypeptides via disulfide bridges.

Figure 12:
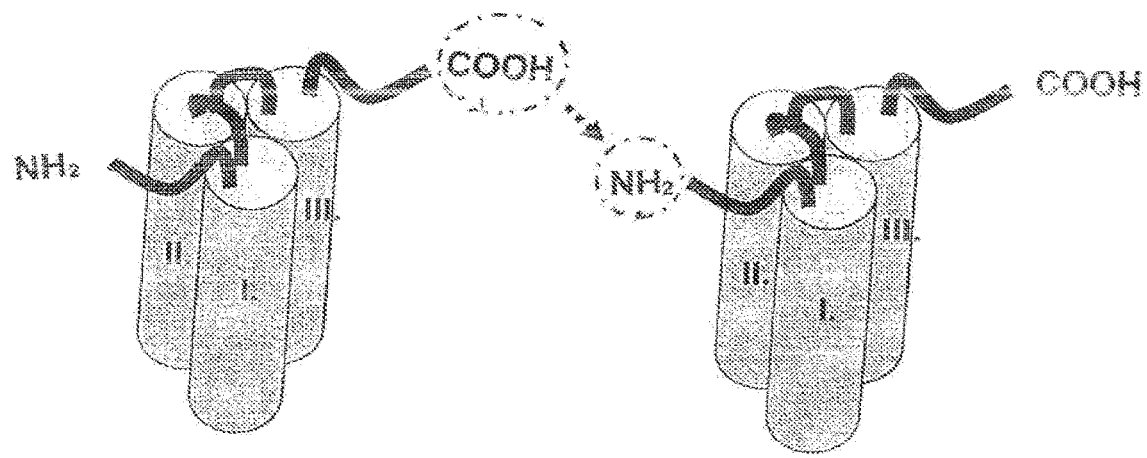

FIG. 12 Dimerization of single-chain fusion polypeptides via a linker.

Figure 13:
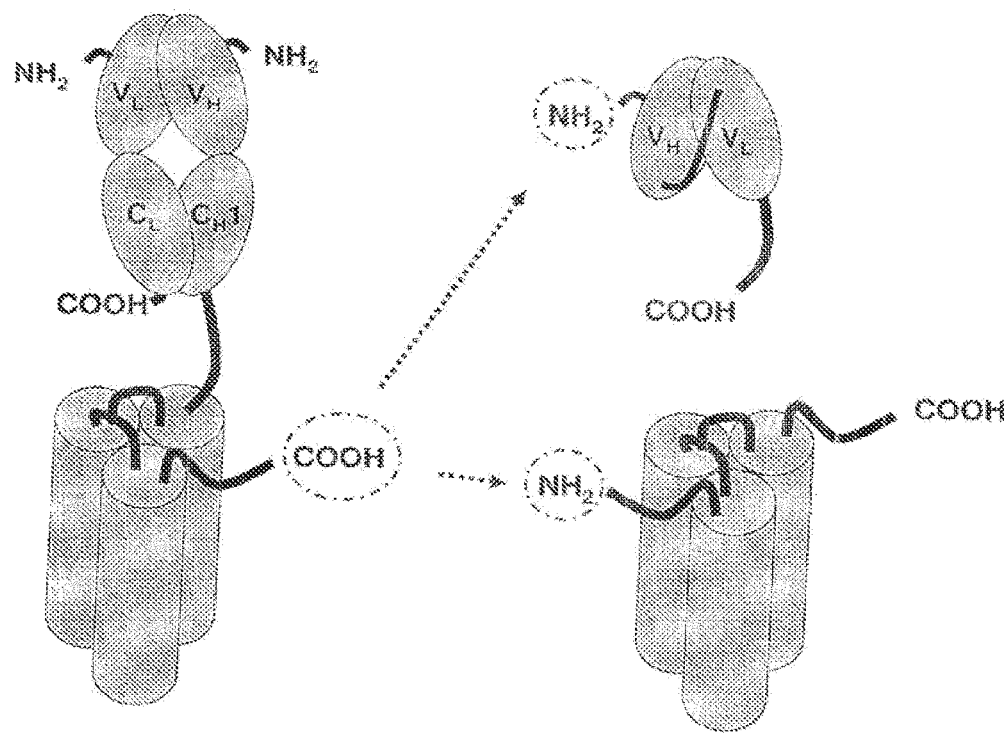

FIG. 13 Single-chain fusion polypeptide comprising an additional Fab antibody fragment further fused to a second fusion polypeptide or to a scFv fusion polypeptide.

Figure 14:
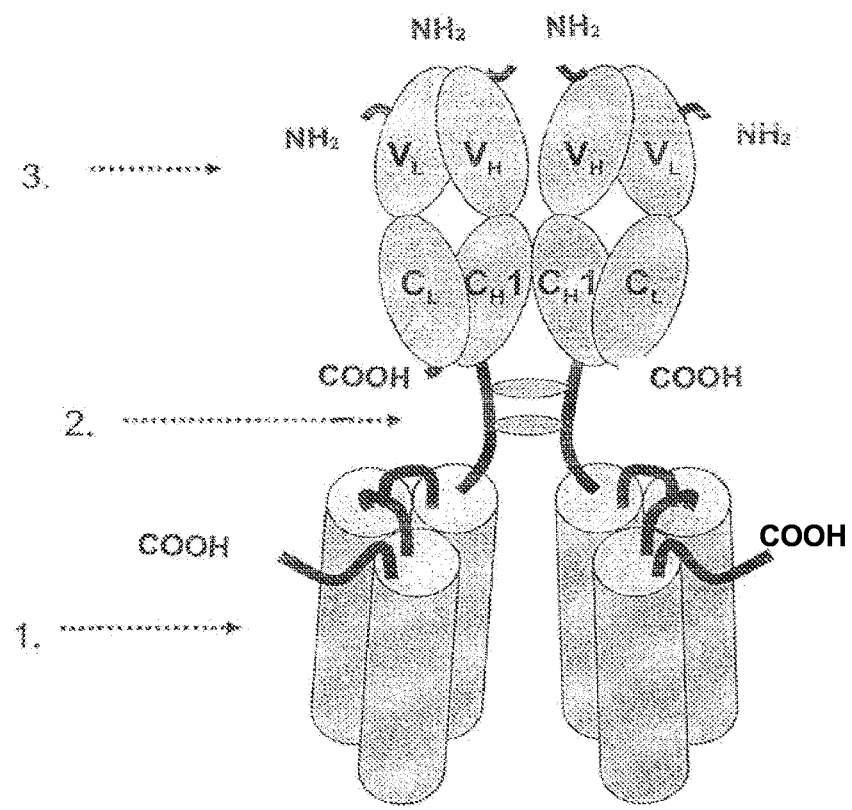

FIG. 14 Dimerization of two scFab fusion polypeptides via disulfide bridges.

Figure 15:
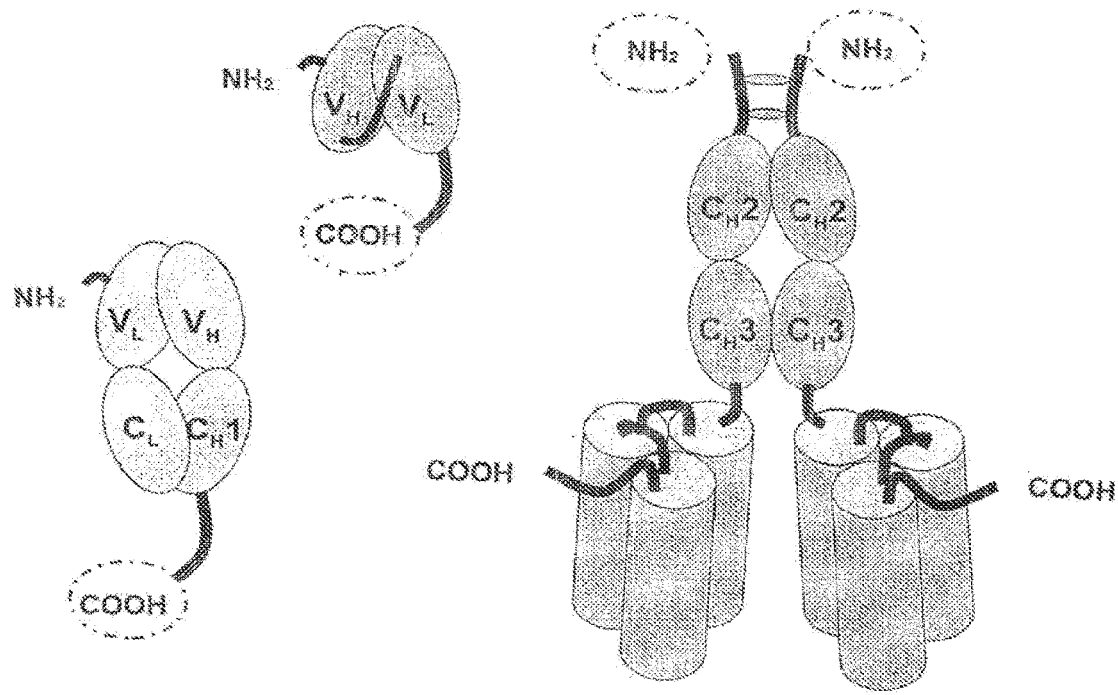

FIG. 15 N-terminally fused scFc fusion polypeptides further comprising a Fv and/or Fab antibody fragment.

Figure 16:
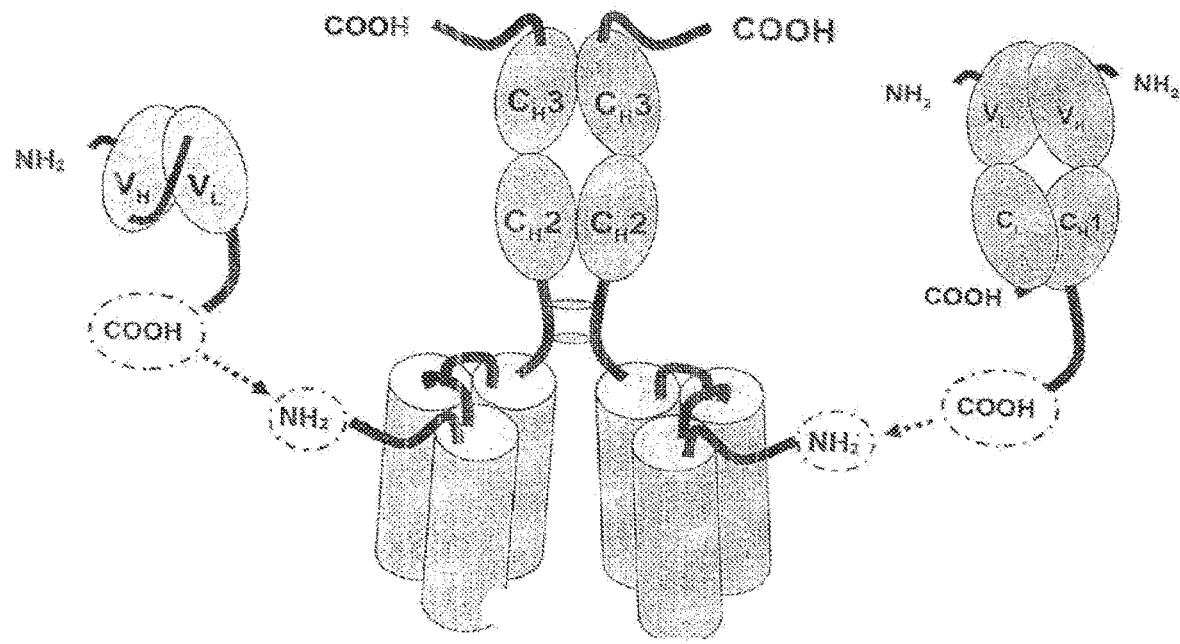

FIG. 16 C-terminally fused scFc fusion polypeptides further comprising a Fv and/or Fab antibody fragment.

Figure 17:
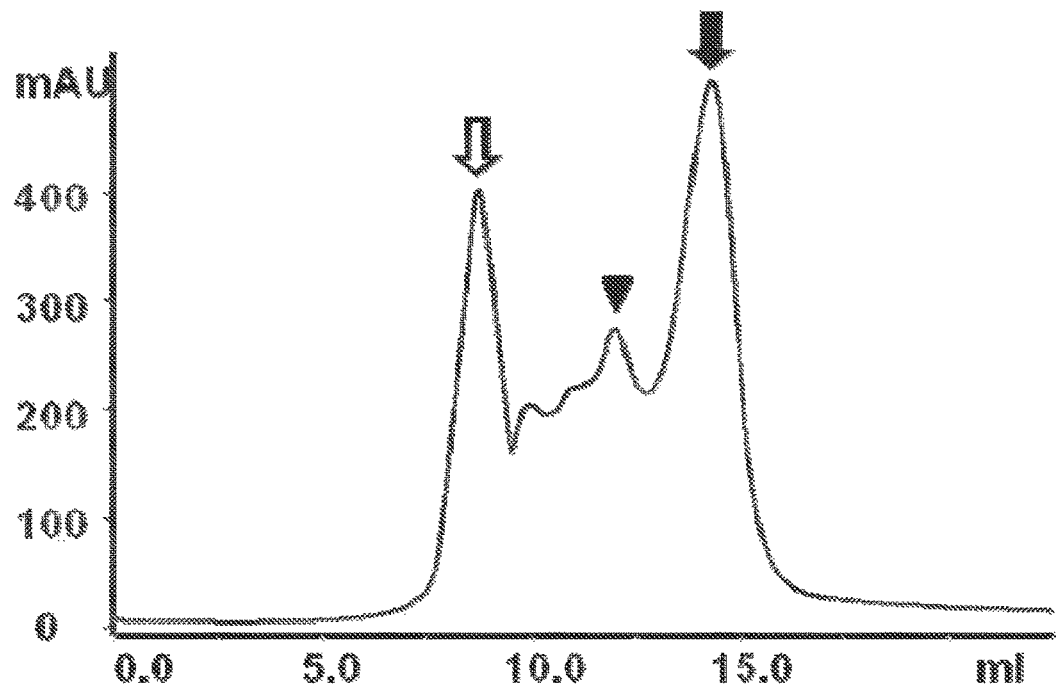
Figure 17:
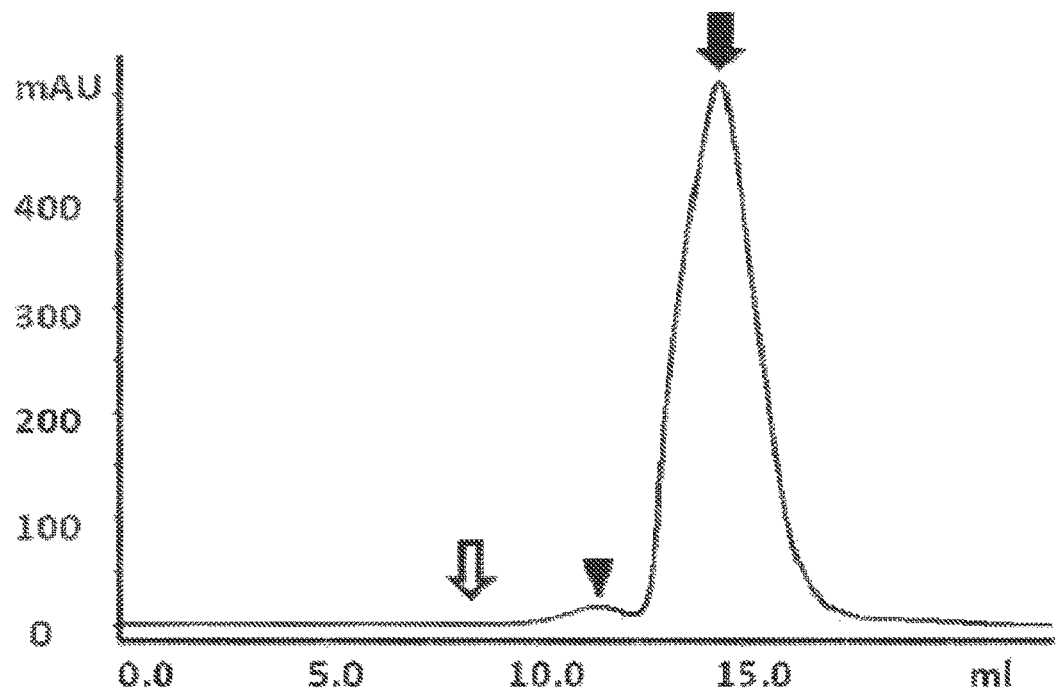

FIG. 17 SEC analysis of recombinantly expressed, purified TNF-SF members under native conditions. Exemplarily shown are two SEC analyses of purified TNF-SF members on a Superdex200 column under native condition (e.g.: PBS, pH 7.4). The diagrams show the absorption at 280 nm (mAU) plotted against the elution volume (ml). The filled arrow indicates the elution peak for the fraction containing defined, soluble trimeric TNF-SF protein. The triangle indicates the elution peak for the oligomerised TNF-SF. The open arrow indicates the void volume of the SEC-column that contains protein-aggregates, which are too big to be separated (>800 kDa).
- A: TNF-SF protein Aggregation Diagram A exemplarily shows an analysis of a TNF-SF protein preparation that contains a high amount of oligomerised/aggregated protein (indicated by the high amount of protein eluting in the void volume and the high amount of oligomeric protein).
- B: TNF-SF protein defined soluble protein Diagram B exemplarily shows an analysis for a TNF-SF protein preparation that contains almost exclusively defined soluble protein (indicated by the absence of protein eluting in the void volume and by the very limited amount of protein eluting as oligomer).

Figure 18:
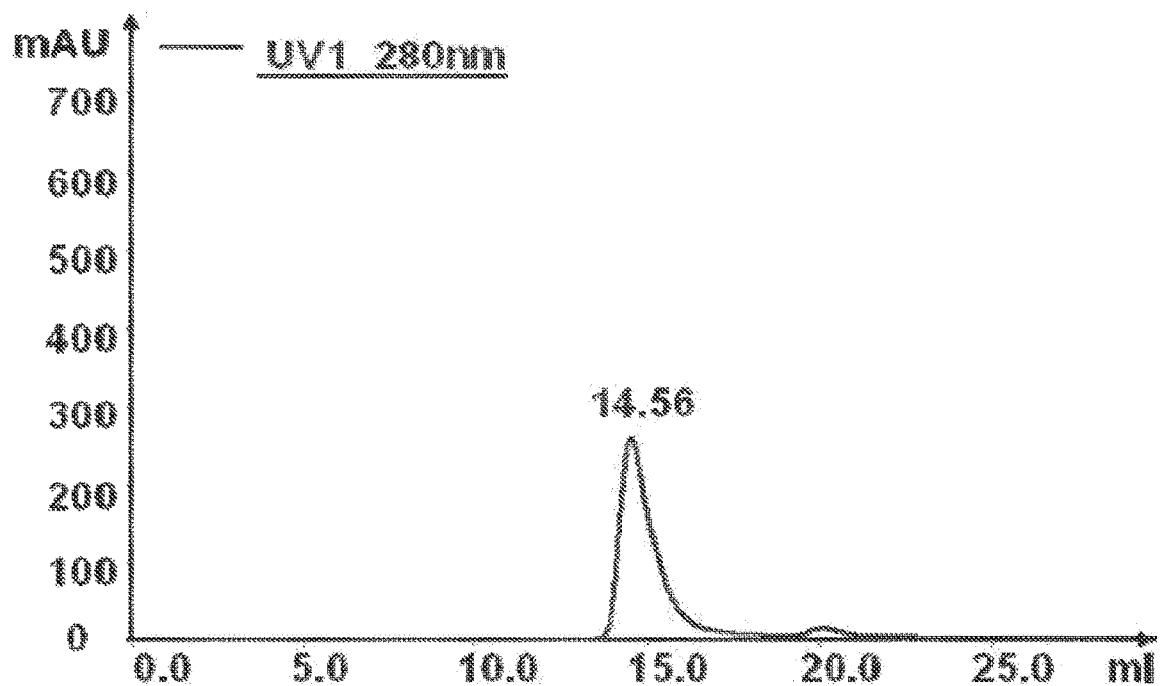

FIG. 18 SEC analysis of recombinantly expressed, affinity purified Fab-scTRAILR2-SSSS. SEC analysis of Fab-sc-TRAILR2-SSSS on a Superdex200 column using PBS, pH 7.4. The diagram shows the absorption at 280 nm (mAU) plotted against the elution volume (ml). The protein elutes as a distinct peak with an elution volume of 14.56 ml, corresponding to an apparent MW of 68 kDa. No additional protein peaks with lower retention volume, indicating oligomerised/aggregated protein, could be observed.

Figure 19:
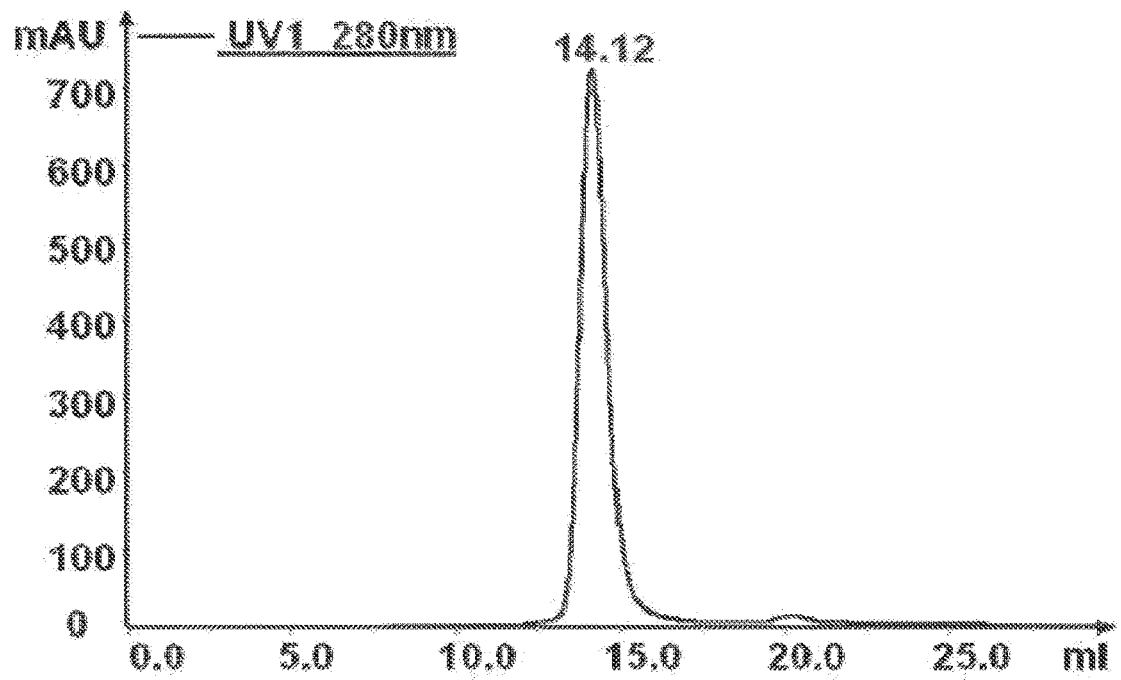

FIG. 19 SEC analysis of recombinantly expressed, affinity purified Fab-scTRAILR2-SNSN. SEC analysis of Fab-sc-TRARR2-SNSN on a Superdex200 column using PBS, pH 7.4. The diagram shows the absorption at 280 nm (mAU) plotted against the elution volume (ml). The protein elutes as a distinct peak with an elution volume of 14.12 ml, corresponding to an apparent MW of 87 kDa. No additional protein peaks with lower retention volume, indicating oligomerised/aggregated protein, could be observed.

Figure 20:
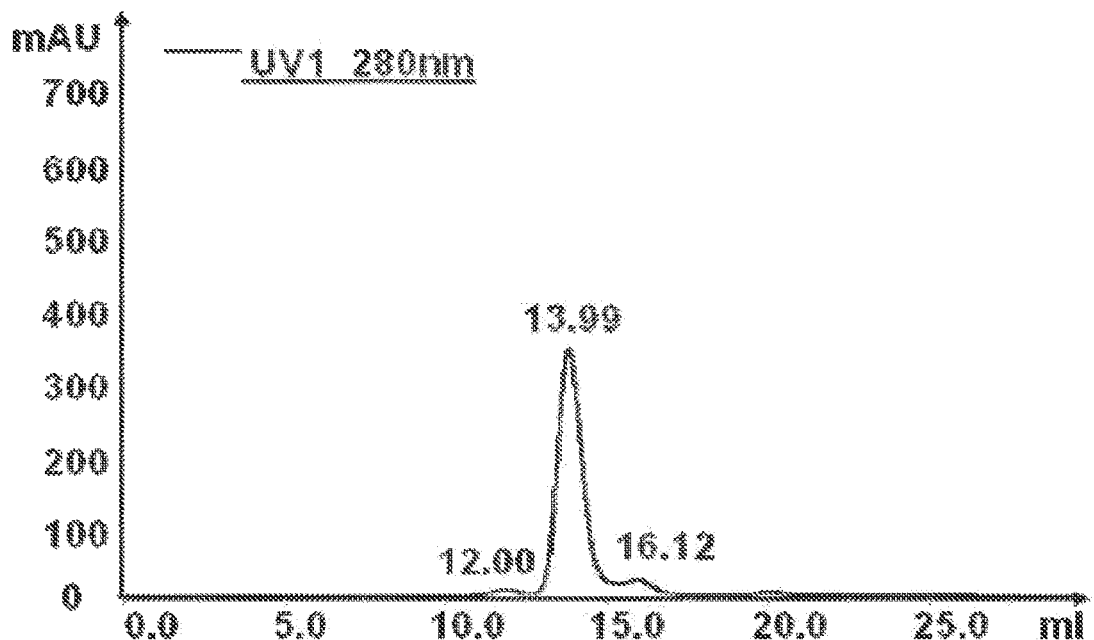

FIG. 20 SEC analysis of recombinantly expressed, affinity purified Fab-scTRAILwt-SNSN. SEC analysis of Fab-sc-TRAILwt-SNSN on a Superdex200 column using PBS, pH 7.4. The diagram shows the absorption at 280 nm (mAU) plotted against the elution volume (ml). The protein elutes as a distinct peak with an elution volume of 13.99 ml, corresponding to an apparent MW of 94 kDa. A small additional protein peak at 12.00 ml could be observed. The apparent Mw of this peak corresponds to about 270 kDa, indicating a defined trimerisation of Fab-scTRAILwt-SNSN. The total protein amount of the peak at 12.00 ml accounts for <3% of the total protein. More than 97% of the analysed Fab-scTRAILwt-SNSN has a defined soluble state (correct assembly of the three receptor binding modules). The peak at 16.12 ml corresponding to a MW of 28 kDa contains Fab-light-chain polypeptide and was not included for the analysis of peak areas.

Figure 21:
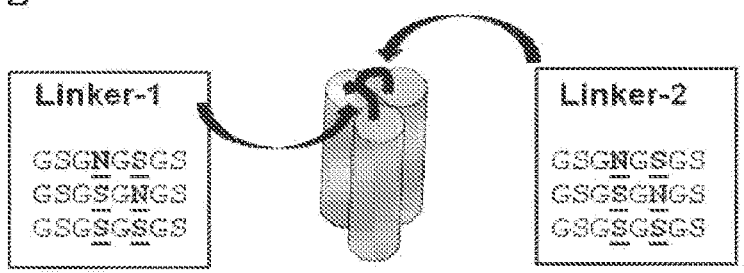

FIG. 21 Human scTRAIL Linker glycosylation
- A: Amino acid sequence of the linker(s) used to combine the receptor binding modules of single chain TRAIL constructs. Gly281 encodes the last amino acid of a respective receptor binding module, the sequence GSGN/SGN/SGS (SEQ ID NOs: 52-54) encodes the linker sequence, Arg121 encodes the first amino acid of the following TRAIL receptor binding domain. The designed linker sequences contains two putative N-linked glycosylation sites at position 1 or 2 as indicated. These positions were permutated as indicated (version I, II, III, SEQ ID NOs: 52-54).
- B: Combination of linker positions: The scTRAIL molecules contain three homologue modules (grey barrels) that are connected with linker 1 (SEQ ID NOs: 52-54) and linker 2 (SEQ ID NOs: 52-54) as indicated. Each of the two linkers, can be designed for N-linked glycosylation as described in "A". A complete set of 9 different proteins containing all possible combinations of linkers can be designed based on the sequences shown in B for linker 1 and 2. (Six of these proteins were expressed—see "C").
- C: Nomenclature of scTRAIL constructs expressed to test the influence of different linker sequences on glycosylation FIG. 22 Western Blot analysis of recombinant scTRAIL constructs
Single chain TRAIL proteins with different linker sequences were recombinantly expressed, separated by SDS-PAGE and transferred to a PVDF-membrane. Bound proteins were detected with a mouse monoclonal antibody recognising the Strep-Tag followed by a Peroxidase-conjugated secondary anti-mouse antibody. Different TRAIL variants were loaded as indicated. Note the MW-shift indicating differential glycosylation of scTRAIL-linker variants.

Figure 23:
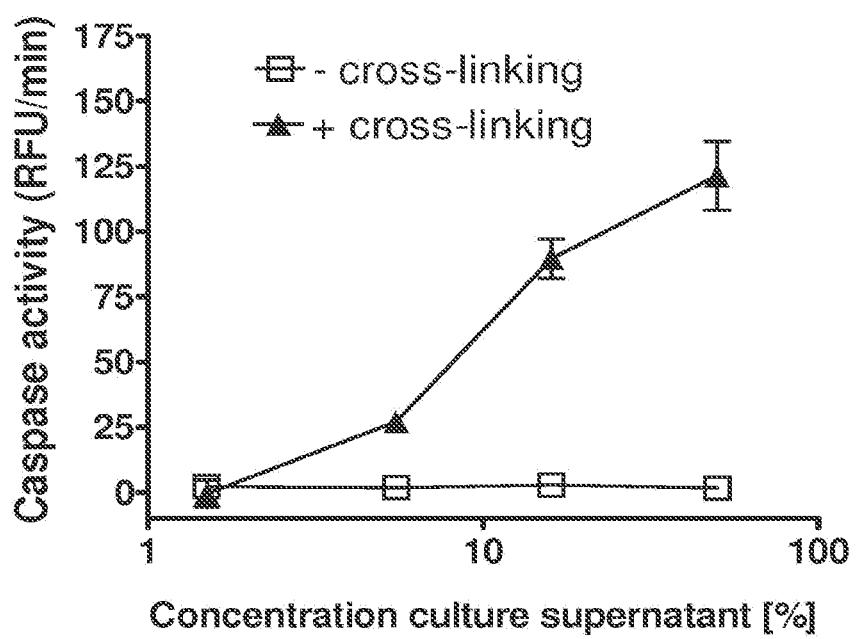

FIG. 23 Cell culture supernatant of HEK293 cells, transiently expressing scCD95L (SEQ ID NO:27) was collected and used to stimulate Jurkat cells at varying concentrations. The supernatant was used either directly without further modifications or an anti-Streptag antibody (2 microgram/ml) was added to cross-link the scCD95L protein. Jurkat cells were incubated with HEK293 cell culture supernatant for three hours at 37°, lysed and analysed for caspase activity. Only cell supernatant that contained cross-linked scCD95L-St increased caspase activity in Jurkat cells, indicating that scCD95L alone does not form higher order aggregates able to be pro-apoptotic.

Figure 2:
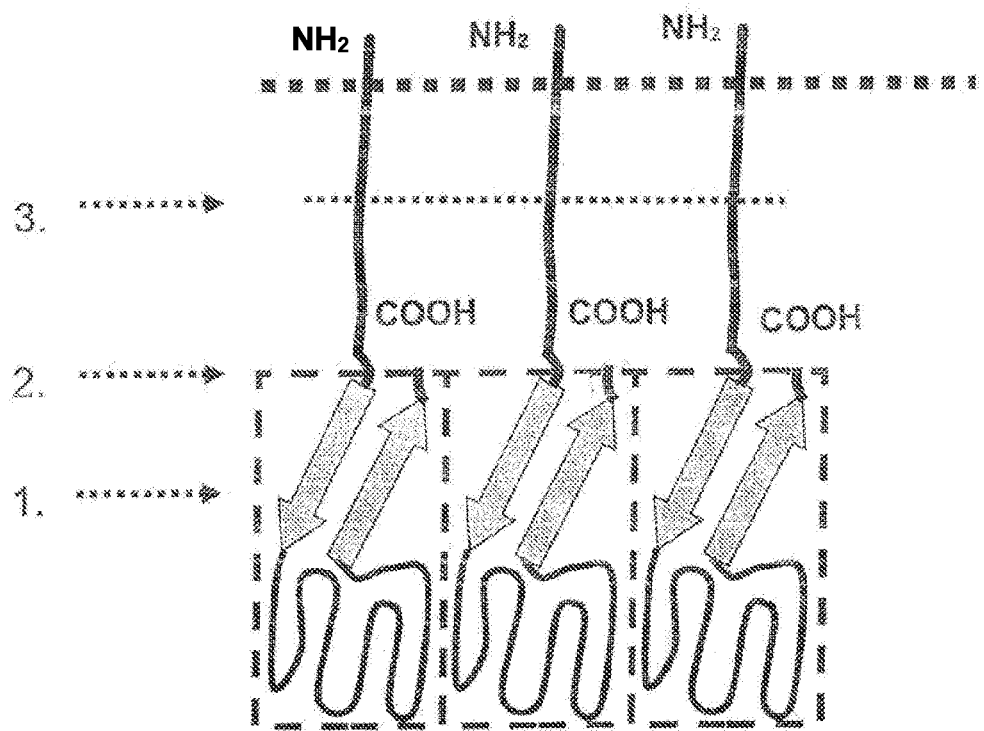
FIG. 2 Schematic picture representing the general structure of TNF-SF
proteins. ■ ■ ■ cell membrane, N-terminus located within the cell, 1. anti-parallel β-fold of receptor-binding domain (RBD), 2. interface of RBD and cell membrane, 3. protease cleavage site.
Figure 24:
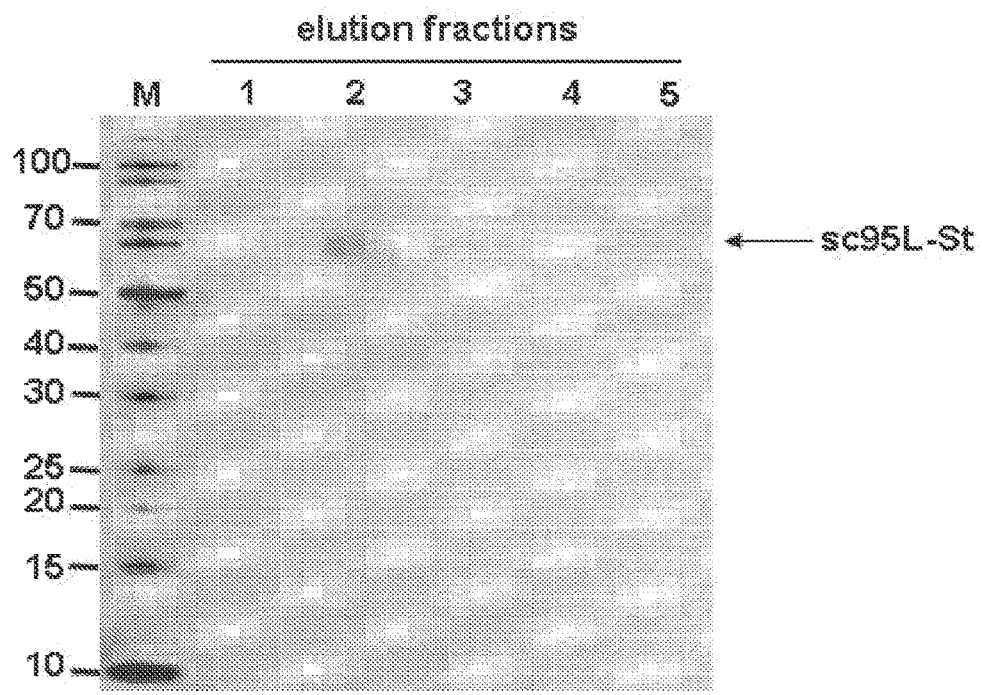

FIG. 24 The protein scCD95L (SEQ ID NO:27) can be produced by transient transfection of HEK293 cells, stable transfection of other eukaryotic cells or by expression using prokaryotic cells. The recombinant protein can be affinity purified by using StrepTactin Sepharose matrix. Bound protein can be eluted with a buffer containing desthio-biotin. FIG. 2 shows a silver stained SDS-PAGE of the elution fractions (lanes 1 to 5; fraction 2 is positive) of the affinity purification. The elution fraction containing scCD95L could be applied to size exclusion chromatography (SEC). It is expected, that the protein shows only a low aggregate content.

Figure 25:
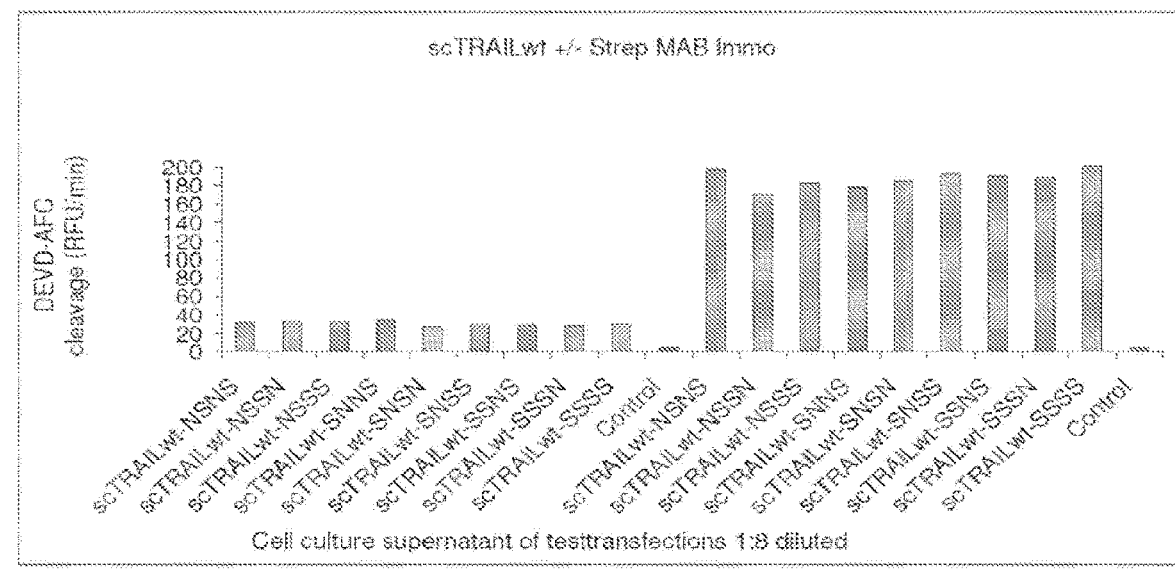

FIG. 25 Cell culture supernatants of HEK293 cells, transiently expressing single chain TRAIL proteins with different linkers (derived from SEQ ID NO: 28) were collected and used to stimulate Jurkat cells at varying dilutions (exemplarily, a dilution of 1:8 is shown in this figure). The supernatants were used either directly without further modifications or an anti-Streptag antibody (2 microgram/ml Strep MAB Immo) was added to cross-link the scTRAIL proteins. Jurkat cells were incubated with HEK293 cell culture supernatant for three hours at 37°, lysed and analysed for caspase activity. Cell culture supernatant that contained cross-linked scTRAILwt proteins induced an increased caspase activity in Jurkat cells, indicating that scTRAILwt proteins alone do form only a low amount of higher order aggregates able to be pro-apoptotic.

Figure 26:
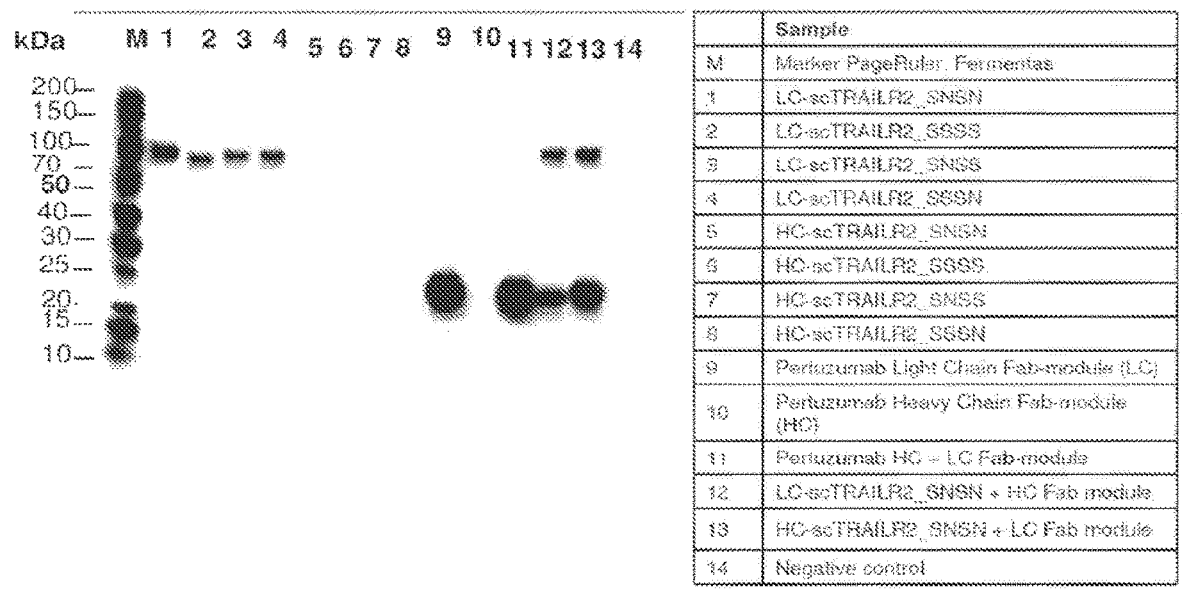

FIG. 26 Influence of the module succession of scTRAIL-construct components on their expression rate of Fab-scTRAIL fusion proteins. Western blot of HEK293T cell culture supernatants from transient expression experiments. The polypeptide chains necessary for the formation of the Fab-scTRAIL proteins were either expressed separately (lanes 1 to 10) or alternatively co-expression experiments were performed (lanes 11-13). After reducing SDS-PAGE, proteins were transferred to a nitrocellulose membrane and proteins containing a Streptag were detected, using an anti-Streptag specific mAB as primary AB. The light-chain-scTRAIL(R2-specific) proteins were secreted even in the absence of the accessory heavy chain (lanes 1-4). In contrast, the heavy-chain-scTRAIL(R2-specific) fusion proteins were not secreted in the absence of the accessory light chain (lanes 5-8). As exemplified in lane 13, the heavy-chain-scTRAIL(R2-specific) fusion proteins were only secreted in the presence of the light chain.

Figure 27:
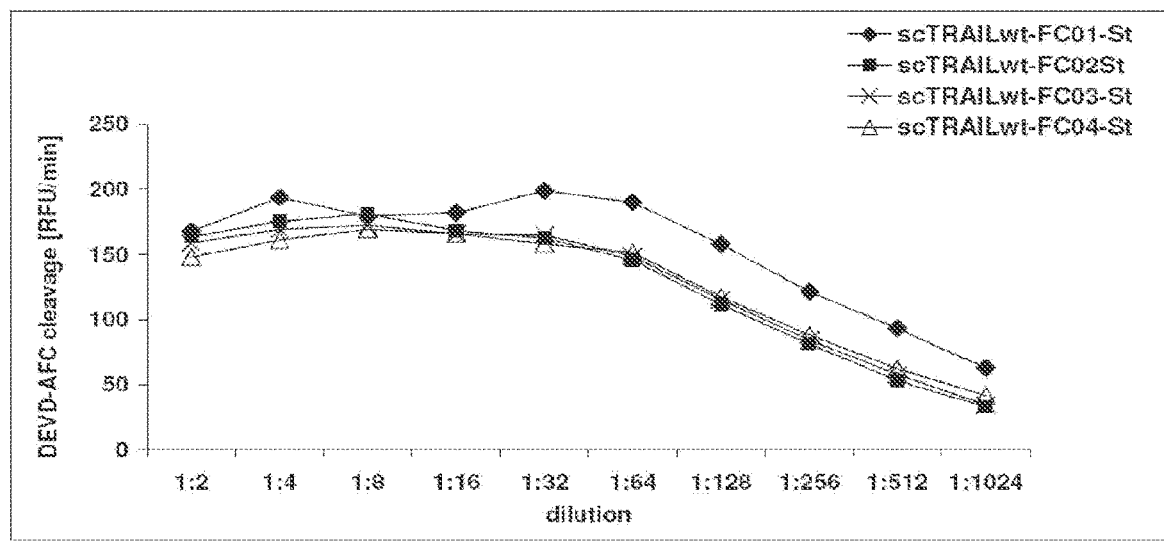

FIG. 27 Cell culture supernatants of HEK293T cells, transiently expressing scTRAILwt-Fc fusion proteins with different linkers were collected and used to stimulate Jurkat cells at varying dilutions. The supernatants were used directly without further modifications. Jurkat cells were incubated with HEK293T cell culture supernatant for three hours at 37°, lysed and analysed for caspase activity. There was already a pronounced pro-apoptotic capacity present in the scTRAILwt-Fc containing supernatants, indicating that scTRAILwt-Fc fusion proteins alone do form dimeric assemblies able to be pro-apoptotic.

Figure 28:
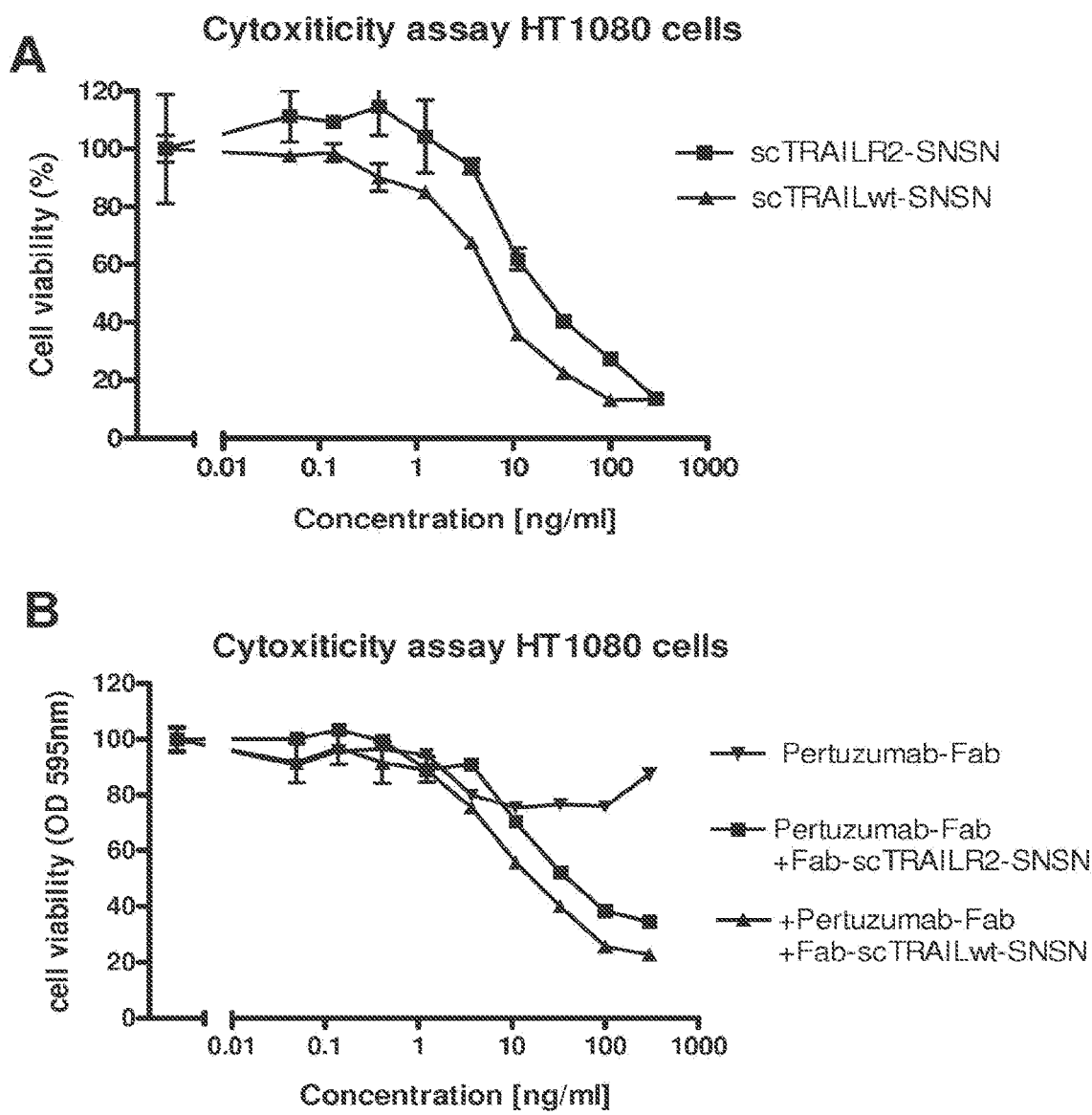

FIG. 28 It is well known that the use of artificially cross-linked or a membrane-bound ligand of the TNF superfamily has superior bioactivity as compared to soluble, homotrimeric ligand. Thus the local enrichment of single chain TRAIL (scTRAIL) constructs on cells that express the antigen Her2 via the Her2-selective Fab-fragment ("Pertuzumab") fused to these scTRAIL proteins should increase their cytotoxic bioactivity. Likewise, the blocking of the Her2 binding sites on cells by pre-incubation with the Her2-specific Fab-fragment (Pertuzumab-Fab) only should decrease the cytotoxic bioactivity of Fab-scTRAIL fusion proteins. As shown in A, scTRAIL constructs induce the death of HT1080 cells, as the viability decreases with increasing protein concentration. As shown in B, the pre-incubation of HT1080 cells with the Fab-fragment (Pertuzumab-Fab), followed by co-incubation with the Fab-scTRAIL constructs (Fab-scTRAILR2-SNSN or Fab-scTRAILwt-SNSN) overnight, reduced the cytotoxic activity of the Fab-scTRAIL constructs, whereas the Fab only induced no cell death (Pertuzumab-Fab). This means that the Fab-scTRAIL constructs bind to HT1080 cells via the Fab fragment thus increasing the cytotoxic bioactivity of scTRAIL.

DETAILED DESCRIPTION OF THE INVENTION

According to the present invention a substantially non-aggregating fusion polypeptide comprising at least three soluble TNF family ligand domains connected by two peptide linkers is provided.

The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the monomer content is as defined above after a time period of several days, e.g. 10 days, more preferably after several weeks, e.g. 2, 3 or 4 weeks, and most preferably after several months, e.g. 2 or 3 months of storage at 4° C., or 25° C. As an increase of e.g. the apoptosis inducing potential in the case of scCD95L on human Jurkat cells correlates with its aggregation state, the stability of the fusion polypeptide concerning aggregation may also be determined by examining the biological activity of the fusion polypeptide.

The single-chain fusion polypeptide may comprise additional domains which may be located at the N- and/or C-termini thereof. Examples for additional fusion domains are e.g. single-chain antibodies or antibody fragments or other targeting molecules or a further cytokine domain, e.g. an interleukin.

The single-chain fusion protein comprises three soluble domains derived from a cytokine of the TNF superfamily. Preferably, those soluble domains are derived from a mammalian, particularly human cytokine including allelic variants and/or derivatives thereof. The soluble domains comprise the extracellular portion of a TNFSF cytokine including the receptor binding domain without membrane located domains. Proteins of the TNF superfamily are anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD).

Figure 3:
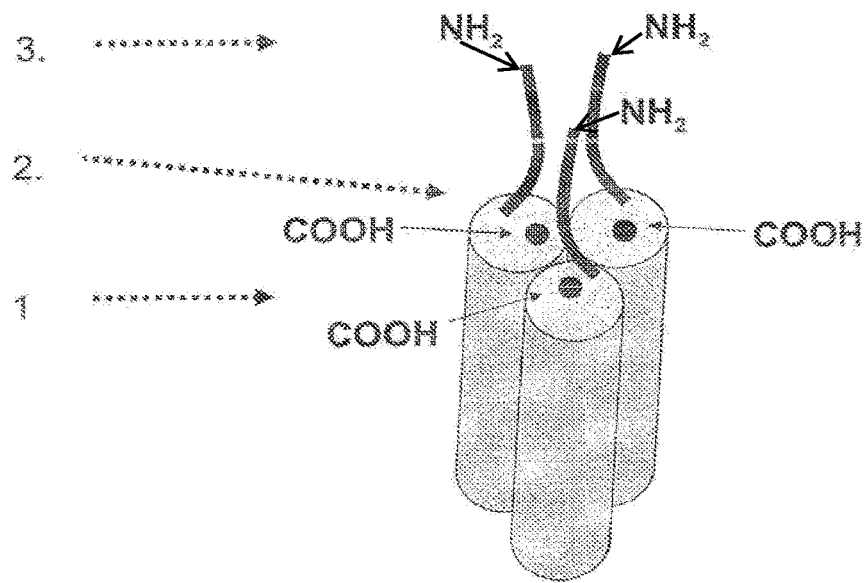
FIG. 3 Schematic picture representing the structure of the native TNF-SF trimer. Cylindric structures represent RBDs, N-termini connect RBD with the cell membrane.

Importantly, the RBD is characterised by a particular localisation of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIGS. 2 and 3).

Figure 4:
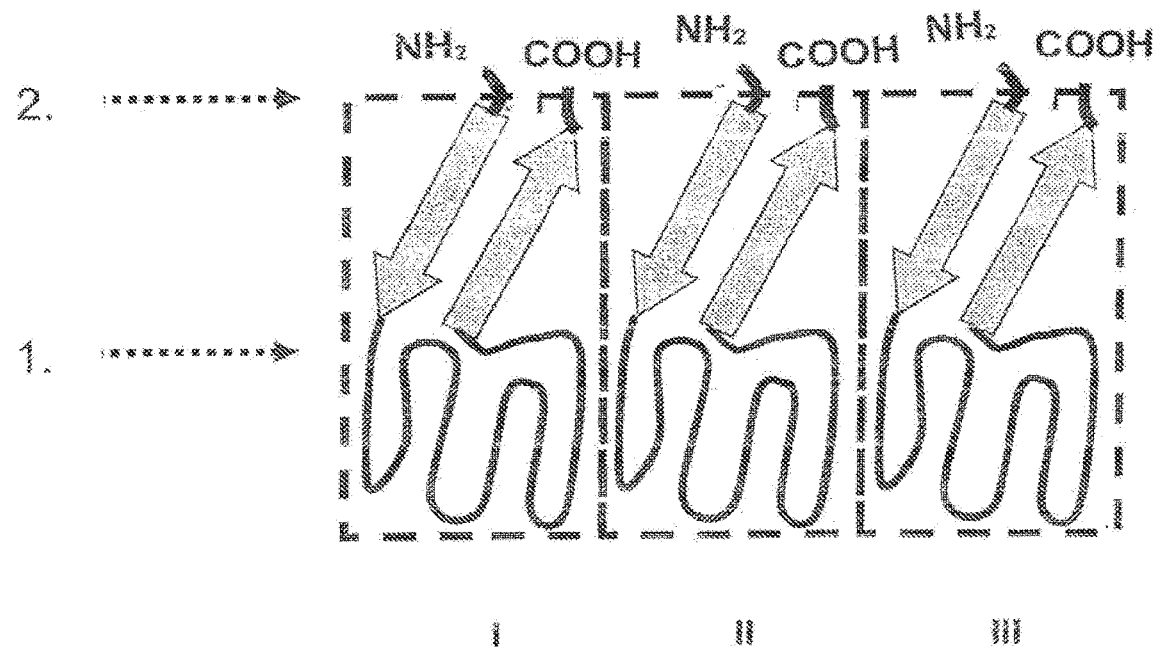
FIG. 4 Schematic picture representing the structure of three soluble domains comprising the receptor-binding domain of a TNF cytokine. I., II., III. soluble TNF-family cytokine domains.
Figure 5:
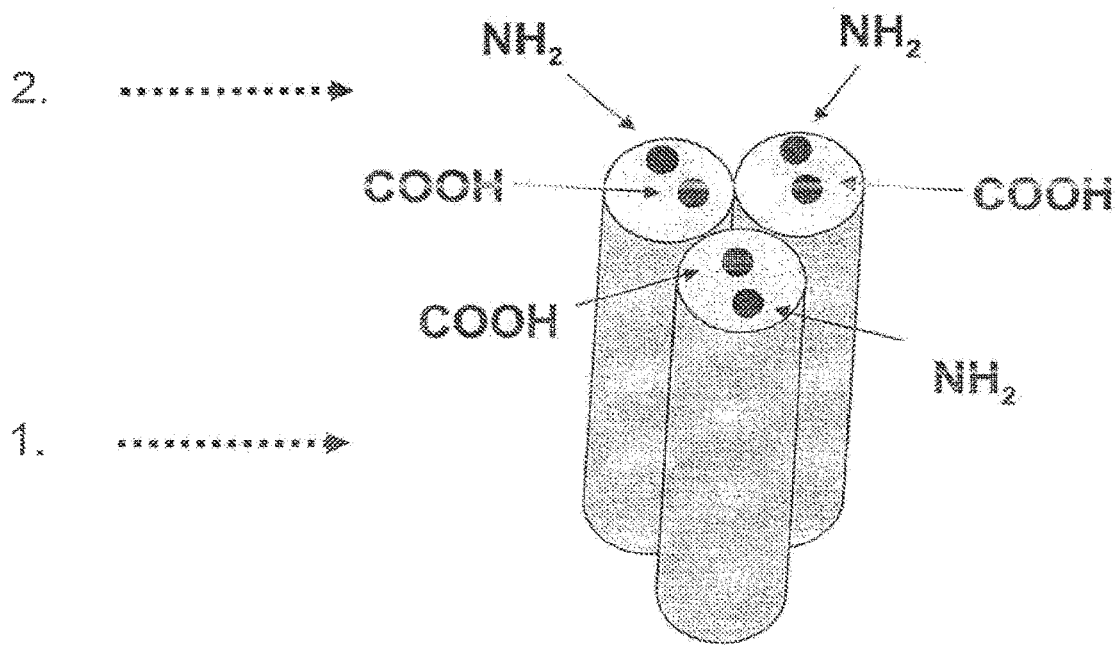
FIG. 5 Trimerisation of the soluble domains comprising the RBD of a TNF cytokine, characterised in that the N- and C-termini of the three soluble domains form a surface.
Figure 6:
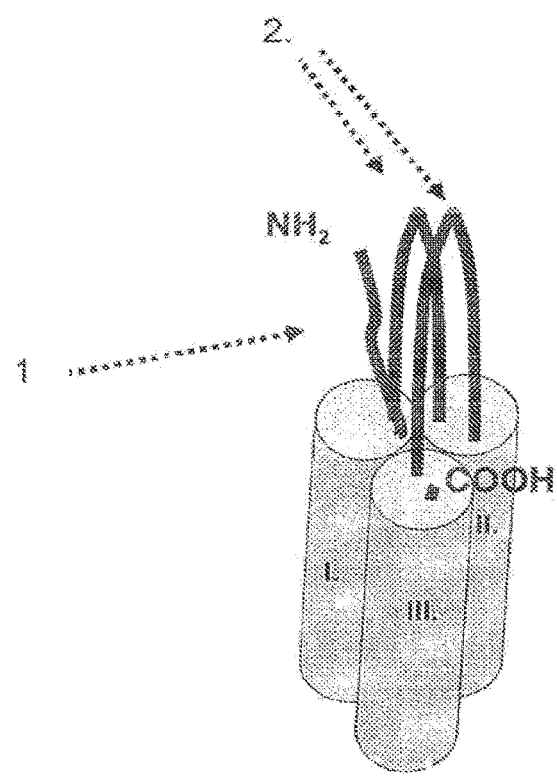
FIG. 6 Schematic picture representing the structure of the single-chain TNF-SF comprising all or a part of the stalk-region illustrating the requirement of longer linkers to compensate for the distance to the N-terminus of the next soluble domain.

Thus, the anti-parallel beta-strand of the RBD forms an interface with the cell membrane, which is connected to and anchored within the cell membrane via the amino acids of the stalk region. It is highly preferred that the soluble domains of the single-chain fusion protein comprises a receptor binding domain of the TNF-SF cytokine lacking any amino acids from the stalk region (FIGS. 4 and 5). Otherwise, a long linker connecting the C-terminus of one of the soluble domains with the N-terminus of the next soluble domain would be required to compensate for the N-terminal stalk-region of the next soluble domain (FIG. 6), which might result in instability and/or formation of aggregates.

A further advantage of such soluble domains is that the N- and C-terminal amino acids of the RBD are not accessible for any anti-drug antibodies.

Preferably, the single-chain fusion polypeptide is capable of forming an ordered trimeric structure comprising at least one functional binding site for the respective cytokine receptor. The fusion polypeptide may comprise one, two or three functional cytokine receptor binding sites, i.e. amino acid sequences capable of forming a complex with a cytokine receptor. Thus, at least one of the soluble domains is capable of binding to the corresponding cytokine receptor. In one embodiment, at least one of the soluble domains is capable of receptor activation, whereby apoptotic and/or proliferative activity may be effected. In a further embodiment, one or more of the soluble domains are selected as not being capable of receptor activation.

The soluble domain may be derived from TNF superfamily members, e.g. human TNFSF-1 to −18 and EDA-A1 to -A2 as indicated in Table 1, preferably from LTA (SEQ ID NO:1), TNFa (SEQ ID NO:2), LTB (SEQ ID NO:3), OX40L (SEQ ID NO:4), CD40L (SEQ ID NO:5), CD95L (SEQ ID NO:6), CD27L (SEQ ID NO:7), CD30L (SEQ ID NO:8), CD137L (SEQ ID NO:9), TRAIL (SEQ ID NO:10), RANKL (SEQ ID NO:11), TWEAK (SEQ ID NO:12), APRIL 1 (SEQ ID NO:13), APRIL 2 (SEQ ID NO:14), BAFF (SEQ ID NO:15), LIGHT (SEQ ID NO:16), TL1A (SEQ ID NO:17), GITRL (SEQ ID NO:18), EDA-A1 (SEQ ID NO:19) and EDA-A2 (SEQ ID NO:20). Preferred soluble domains of the respective proteins are indicated in Table 1 (NH2-aa to COOH-aa) and, e.g., comprise amino acids 59-205, 60-205 or 64-205 of LTA (SEQ ID NO:1), 86-233 of TNFα (SEQ ID NO:2), 82-244 or 86-244 of LTB (SEQ ID NO:3), 52-183 or 55-183 of OX40L (SEQ ID NO:4), 112-261, 117-261 or 121-261 of CD40L (SEQ ID NO:5), 51-193 or 56-193 of CD27L (SEQ ID NO:7), 97-234, 98-234 or 102-234 of CD30L (SEQ ID NO:8), 86-254 of CD137L (SEQ ID NO:9), 161-317 of RANKL (SEQ ID NO:11), 103-249, 104-249, 105-249 or 106-249 of TWEAK (SEQ ID NO:12), 112-247 of APRIL 1 (SEQ ID NO:13), 112-250 of APRIL 2 (SEQ ID NO:14), 140-285 of BAFF (SEQ ID NO:15), 91-251, 93-251 or 97-251 of TL1A (SEQ ID NO:17), 52-177 of GITRL (SEQ ID NO:18), 245-391 of EDA-A1 (SEQ ID NO:19), 245-389 of EDA-A2 (SEQ ID NO:20).

More preferably, the soluble domains are derived from CD95L, TRAIL or LIGHT. In an especially preferred embodiment, the soluble domains are selected from human CD95L, particularly starting from amino acids 144, 145 or 146 and comprise particularly amino acids 144-281 or 145-281 or 146-281 of SEQ ID NO:6 or human TRAIL, particularly starting from amino acids 120-122 and comprise particularly amino acids 120-281, 121-281 or 122-281 of SEQ ID NO:10. Optionally, amino acid Lys145 of SEQ ID NO:6 may be replaced by a non-charged amino acid, e.g. Ser or Gly. Optionally, amino acid Arg121 of SEQ ID NO:10 may be replaced by a non-charged amino acid, e.g. Ser or Gly. In a further preferred embodiment, the soluble domains are selected from human LIGHT, particularly starting from amino acids 93, 94 or 95 of SEQ ID NO:16 and particularly comprise amino acids 93-240, 94-240 or 95-240 of SEQ ID NO:16.

As indicated above, the soluble domains may comprise the wild-type sequences as indicated in SEQ ID NO: 1-20. It should be noted, however, that it is possible to introduce mutations in one or more of these soluble domains, e.g. mutations which alter (e.g. increase or decrease) the binding properties of the soluble domains. In one embodiment, soluble domains may be selected which cannot bind to the corresponding cytokine receptor. An example of such a mutation is a replacement of amino acid Y218 in human CD95L (SEQ ID NO:6) by another amino acid, e.g. R, K, S or D. Further, a mutation may be introduced which alters the binding to other cellular and/or extracellular components, e.g. the extracellular matrix. An example of such a mutation is a replacement of amino acid K177 in CD95L (SEQ ID NO: 6) by another amino acid, e.g. E, D or S.

In a further preferred embodiment of the invention, the soluble cytokine domain (i) comprises a mutant of the cytokine of the TNF superfamily or a receptor binding domain thereof which binds and/or activates TRAIL-receptor 1 (TRAILR1) and/or TRAIL-receptor 2 (TRAILR2). The binding and/or activity of the mutant may be, e.g., determined by the assays as described in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270).

The mutant may be generated by any technique and is known by the skilled person, e.g., the techniques described in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270) and may comprise any type of structural mutations, e.g., substitution, deletion, duplication and/or insertion of an amino acid. A preferred embodiment is the generation of substitutions. The substitution may affect at least one amino acid of the cytokine of the TNF superfamily or a receptor binding domain thereof as described herein. In a preferred embodiment, the substitution may affect at least one of the amino acids of TRAIL, e.g., human TRAIL (e.g., SEQ ID NO: 10). Preferred substitutions in this regard affect at least one of the following amino acids of human TRAIL of SEQ ID NO:10: R130, G160, Y189, R191, Q193, E195, N199, K201, Y213, T214, S215, H264, I266, D267, D269. Preferred amino acid substitutions of human TRAIL of SEQ ID NO:10 are at least one of the following substitutions: R130E, G160M, Y189A, Y189Q, R191K, Q193S, Q193R, E195R, N199V, N199R, K201R, Y213W, T214R, S215D, H264R, I266L, D267Q, D269H, D269R, or D269K.

The amino acid substitution(s) may affect the binding and/or activity of TRAIL, e.g., human TRAIL, to or on either the TRAILR1 or the TRAILR2. Alternatively, the amino acid substitution(s) may affect the binding and/or activity of TRAIL, e.g., human TRAIL, to or on both, the TRAILR1 and the TRAILR2. The binding and/or activity of the TRAILR1 and/or TRAILR2 may be affected positively, i.e., stronger, more selective or more specific binding and/or more activation of the receptor. Alternatively, the binding and/or activity of the TRAILR1 and/or TRAILR2 may be affected negatively, i.e., weaker, less selective or less specific binding and/or less or no activation of the receptor.

Examples of mutants of TRAIL with amino acid substitution(s) of the invention that affect binding and/or activation of both TRAILR1 and TRAILR2 may be found, e.g., in Table 1 of MacFarlane et al. (cf. above) and may comprise a human TRAIL mutant with the following two amino acid substitutions of SEQ ID NO: 10 Y213W and S215D or with the following single amino acid substitution: Y189A.

Examples of mutants of TRAIL with amino acid substitution(s) of the invention that affect binding and/or activation of TRAILR1 may be found, e.g., in Table 1 of MacFarlane et al. (cf. above) and may comprise a human TRAIL mutant with the following four amino acid substitutions of SEQ ID NO: 10 N199V, K201R, Y213W and S215D or with the following five amino acid substitutions: Q193S, N199V, K201R, Y213W and S215D, or may be found in Table 2 of Kelley et al. (cf. above) and may comprise a human TRAIL mutant with the following six amino acid substitutions: Y213W, S215D, Y189A, Q193S, N199V, and K201R, or with Y213W, S215D, Y189A, Q193S, N199R, and K201R.

Examples of mutants of TRAIL with amino acid substitution(s) of the invention that affect binding and/or activation of TRAILR2 may be found, e.g., in Table 1 of MacFarlane et al. (cf. above) or in Table 2 of Kelley et al. (cf. above) and may comprise a human TRAIL mutant with the following six amino acid substitutions of SEQ ID NO: 10: Y189Q, R191K, Q193R, H264R, I266L, and D267Q, or may be found in Table 2 of van der Sloot et al. (cf. above) and may comprise a human TRAIL mutant with the following single amino acid substitution: D269H, or with the following two amino acid substitutions: D269H and E195R or D269H and T214R.

Thus one preferred embodiment is a fusion protein as described herein wherein at least one of the soluble domains comprises a mutant of TRAIL or of a receptor binding domain thereof which binds and/or activates TRAILR1 and/or TRAILR2.

Further examples of mutants of TRAIL, which show reduced TRAIL induced receptor aggregation are H168 (S, T, Q), R170 (E, S, T, Q) and H177 (S, T).

One preferred embodiment of a fusion protein comprising a mutant of TRAIL or of a receptor binding domain as described herein is a fusion protein wherein component (i) comprises at least one amino acid substitution, particularly as indicated below.

Such an amino acid substitution affects at least one of the following amino acid positions of human TRAIL (SEQ ID NO: 10): R130, G160, H168, R170, H177, Y189, R191, Q193, E195, N199, K201, Y213, T214, S215, H264, I266, D267, D269.

Such an amino acid substitution is at least one of the following: R130E, G160M, H168 (S, T, Q), R170 (E, S, T, Q), H177 (S,T), Y189A, Y189Q, R191K, Q193S, Q193R, E195R, N199V, N199R, K201R, Y213W, T214R, S215D, H264R, I266L, D267Q, D269H, D269R, or D269K.

A preferred TRAIL-R2 selective domain comprises amino acid substitutions Y189Q, R191K, Q193R, H264R, I266L and D267Q.

A preferred TRAIL-R1 selective domain comprises amino acid substitutions Y189A, Q193S, N199V, K201R, Y213W and S215D.

The single-chain fusion molecule of the present invention comprises additionally three soluble cytokine domains, namely components (i), (iii) and (v). According to the present invention, it was surprisingly found that the stability of a single-chain TNF family cytokine fusion polypeptide against aggregation is enhanced, if the second and/or third soluble TNF family cytokine domain is an N-terminally shortened domain which optionally comprises amino acid sequence mutations. Thus, preferably, both the second and the third soluble TNF family cytokine domain are N-terminally shortened domains which optionally comprise amino acid sequence mutations in the N-terminal regions, preferably within the first five amino acids of the N-terminus of the soluble cytokine domain. These mutations may comprise replacement of charged, e.g. acidic or basic amino acids, by neutral amino acids, particularly serine or glycine.

In contrast thereto, the selection of the first soluble TNF family cytokine domain is not as critical. Here, a soluble domain having a full-length N-terminal sequence may be used. It should be noted, however, that also the first soluble cytokine domain may have an N-terminally shortened and optionally mutated sequence.

In a preferred embodiment of the present invention, the soluble TNF family cytokine domains (i), (iii) and (v) are soluble CD95L domains, particularly soluble human CD95L domains. The first soluble CD95L domain (i) may be selected from native, shortened and/or mutated sequences. The N-terminal sequence of the first domain (i) may e.g. start between amino acid Glu142 and Val146 of human CD95L, wherein Arg144 and/or Lys145 may be replaced by a neutral amino acid, e.g. by Ser or Gly. The second and third soluble CD95L domains (iii) and (v), however, are selected from shortened and/or mutated sequences. Preferably, at least one of the soluble CD95L domains, (iii) and (v), has an N-terminal sequence which starts between amino acid Arg144 and Val146 of human CD95L, and wherein Arg144 and/or Lys145 may be replaced by a neutral amino acid, e.g. by Ser and/or Gly. In an especially preferred embodiment, the second and third soluble CD95L domain start with an N-terminal sequence selected from:

(a) Arg144-(Gly/Ser) 145-Val (146)
(b) (Gly/Ser) 144-Lys145-Val (146) and
(c) (Gly/Ser) 144-(Gly/Ser) 145-Val (146).

Further, it is preferred that the CD95L domain ends with amino acid Leu 281 of human CD95L.

The soluble CD95L domain may comprise a mammalian, e.g. a human wild-type sequence. In certain embodiments, however, the CD95L sequence may comprise a mutation which results in a reduction or complete inhibition of the binding to the extracellular matrix, e.g. a mutation at position Lys177, e.g. Lys177→Glu, Asp or Ser and/or a mutation which reduces and/or inhibits binding to the CD95L receptor, e.g. a mutation at position Tyr218, e.g. Tyr218→Arg, Lys, Ser, Asp. In certain embodiments of the present invention, one of the three soluble CD95L modules is a sequence variant with a reduced receptor binding. In other embodiments, two of the modules contain mutations resulting in reduced receptor binding.

In a further preferred embodiment of the present invention, the soluble TNF family cytokine domains (i), (iii) and (v) are soluble TRAIL domains, particularly soluble human TRAIL domains. The first soluble TRAIL domain (i) may be selected from native, shortened and/or mutated sequences. Thus, the first soluble TRAIL domain (i) has an N-terminal sequence which may start between amino acid Glu116 and Val122 of human TRAIL, and wherein Arg121 may be replaced by a neutral amino acid, e.g. by Ser or Gly. The second and third soluble TRAIL domains (iii) and (v) have a shortened N-terminal sequence which preferably starts between amino acid Gly120 and Val122 of human TRAIL and wherein Arg121 may be replaced by another amino acid, e.g. Ser or Gly.

Preferably, the N-terminal sequence of the soluble TRAIL domains (iii) and (v) is selected from:
(a) Arg121-Val122-Ala123 and
(b) (Gly/Ser)121.

The soluble TRAIL domain preferably ends with amino acid Gly281 of human TRAIL. In certain embodiments, the TRAIL domain may comprise internal mutations as described above.

In a further preferred embodiment of the present invention, the soluble TNF family cytokine domains (i), (iii) and (v) are soluble LIGHT domains, particularly soluble human LIGHT domains. The first soluble LIGHT domain (i) may be selected from native, shortened and/or mutated sequences. Thus, the first soluble LIGHT domain (i) has an N-terminal sequence which may start between amino acid Glu91 and Ala95 of human LIGHT. The second and third soluble LIGHT domains (iii) and (v) have a shortened N-terminal sequence which preferably starts between amino acid Pro94 and Ala95 of human LIGHT. The soluble LIGHT domain preferably ends with amino acid Val240.

Components (ii) and (iv) of the single-chain fusion polypeptide are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in which the soluble cytokine domain terminates with S or G (C-terminus), e.g. human TRAIL, the linker starts after S or G. In cases in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavourable aggregations properties.

If desired, the linker may comprise an asparagine residue which may form a glycosylation site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the scTNF-SF proteins and/or in order to reduce the potential immunogenicity, it may be preferred that linker (ii) or linker (iv) or both comprise a glycosylation site.

Preferred linker sequences are selected from GSGSGSGS (SEQ ID NO:52), GSGSGNGS (SEQ ID NO:53), GGSGSGSG (SEQ ID NO:21), GGSGSG (SEQ ID NO:22), GGSG (SEQ ID NO:23), GGSGNGSG (SEQ ID NO:24), GGNGSGSG (SEQ ID NO:25) and GGNGSG (SEQ ID NO:26)

The fusion protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. Further, the fusion protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain.

Further, the fusion polypeptide may additionally comprise N-terminally and/or C-terminally a further domain, e.g. a targeting domain such as a single-chain antibody or an antibody fragment domain. Specific examples of suitable antibodies are anti-tumour antibodies, such as antibodies against EGFR-family members. Suitable examples of other targeting molecules are cytokines, such as interleukins.

Examples of specific fusion proteins of the invention are SEQ ID NOs: 27, 28, 29, 43, 45, 47, 49 and 51.

A further aspect of the present invention relates to a nucleic acid molecule encoding a fusion protein as described herein. The nucleic acid molecule may be a DNA molecule, e.g. a double-stranded or single-stranded DNA molecule, or an RNA molecule. The nucleic acid molecule may encode the fusion protein or a precursor thereof, e.g. a pro- or pre-proform of the fusion protein which may comprise a signal sequence or other heterologous amino acid portions for secretion or purification which are preferably located at the N- and/or C-terminus of the fusion protein. The heterologous amino acid portions may be linked to the first and/or second domain via a protease cleavage site, e.g. a Factor $X_a$, thrombin or IgA protease cleavage site.

Examples of specific nucleic acid sequences of the invention are SEQ ID NOs: 30, 31 32, 44, 46, 48 and 50.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosal integration vector, etc. Examples of suitable expression control sequences and vectors are described for example by Sambrook et al. (1989) *Molecular Cloning, A Laboratory Manual*, Cold Spring Harbor Press, and Ausubel et al. (1989), *Current Protocols in Molecular Biology*, John Wiley & Sons or more recent editions thereof.

Various expression vector/host cell systems may be used to express the nucleic acid sequences encoding the fusion proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells.

Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one fusion protein, a respective nucleic acid encoding therefore, or a transformed or transfected cell, all as described herein.

At least one fusion protein, respective nucleic acid encoding therefore, or transformed or transfected cell, all as described herein may be used in therapy, e.g., in the prophylaxis and/or treatment of disorders caused by, associated with and/or accompanied by dysfunction of TNF-SF cytokines, particularly proliferative disorders, such as tumours, e.g. solid or lymphatic tumours; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of TNF-SF cytokines" as used herein is to be understood as any function or expression of a TNF-SF cytokine that deviates from the normal function or expression of a TNF-SF cytokine, e.g., overexpression of the TNF-SF gene or protein, reduced or abolished expression of the TNF-SF cytokine gene or protein compared to the normal physiological expression level of said TNF-SF cytokine, increased activity of the TNF-SF cytokine, reduced or abolished activity of the TNF-SF cytokine, increased binding of the TNF-SF cytokine to any binding partners, e.g., to a receptor, particularly a CD95 or TRAIL receptor or another cytokine molecule, reduced or abolished binding to any binding partner, e.g. to a receptor, particularly a CD95 or TRAIL receptor or another cytokine molecule, compared to the normal physiological activity or binding of said TNF-SF cytokine.

The composition may be administered as monotherapy or as combination therapy with further medications, e.g. cytostatic or chemotherapeutic agents, corticosteroids and/or antibiotics.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, intramuscularly or intravenously or locally, e.g. intranasally, subcutaneously or intrathecally. Preferred is intravenous administration.

The dose of the fusion protein administered will of course be dependent on the subject to be treated, on the subject's weight, the type and severity of the disease, the manner of administration and the judgement of the prescribing physician. For the administration of fusion proteins, a daily dose of 0.001 to 100 mg/kg is suitable.

Examples

1. Manufacture of a Single-Chain CD95L Fusion Protein (scCD95L)

Figure 1:
FIG. 1 Domain structure of the inventive single-chain fusion polypeptide. I., II., III. soluble TNF-family cytokine domains.
Figure 1:
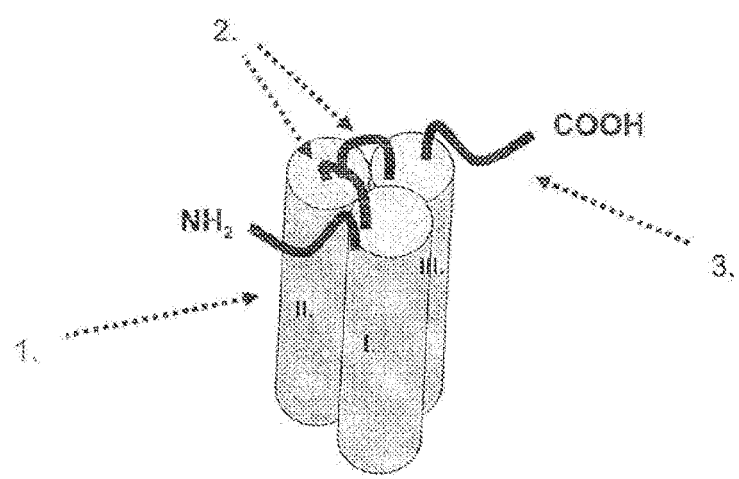

In the following, the general structure of the recombinant proteins of the invention (FIG. 1) is shown exemplified for the receptor binding domain of the human CD95 ligand.

1.1 Polypeptide Structure
A) Amino acids Met1-Ser21
   IgKappa-signal peptide, assumed signal peptidase cleavage site after amino acid Gly20
B) Amino acids Glu22-Leu161
   First soluble cytokine domain of the human CD95 ligand (CD95L; amino acids 142-281 of SEQ ID NO: 6 including a K145S mutation).
C) Amino acids Gly162-Gly169
   First peptide linker element.
D) Amino acids Arg170-Leu307
   Second soluble cytokine domain of the human CD95 ligand (CD95L; amino acids 144-182 of SEQ ID NO: 6 including a K145S mutation).
E) Amino acids Gly308-315
   Second peptide linker element.
F) Amino acids Arg316-Leu453
   Third soluble cytokine domain of the human CD95 ligand (CD95L; amino acids 144-281 of SEQ ID NO: 6 including a K145S mutation).
G) Amino acid Gly457-Lys472
   Peptide linker with a Strep-tag II motif.

The amino acid sequence of sc CD95L is shown in SEQ ID NO. 27. The fusion polypeptide comprises first and second peptide linkers having the sequence GGSGSGSG (SEQ ID NO: 21). Further preferred linker sequences are SEQ ID NOs: 22-26 as described above. It should be noted that the first and second peptide linker sequences need not to be identical.

The signal peptide sequence (A) may be replaced by any other suitable, e.g. mammalian signal peptide sequence. The Strep-tag II motif (G) may be replaced by other motifs, if desired, or deleted.

As shown in FIG. 23, cell culture supernatant of HEK293 cells, transiently expressing scCD95L (SEQ ID NO:27) was collected and used to stimulate Jurkat cells at varying concentrations. The supernatant was used either directly without further modifications or an anti-Streptag antibody (2 microgram/ml) was added to cross-link the scCD95L protein. Only cell supernatant that contained cross-linked scCD95L-St increased caspase activity in Jurkat cells, indicating that scCD95L alone does not form higher order aggregates able to be pro-apoptotic.

1.2 Gene Cassette Encoding the Polypeptide

The synthetic gene may be optimised in view of its codon-usage for the expression in suitable host cells, e.g. insect cells or mammalian cells. A preferred nucleic acid sequence is shown in SEQ ID NO: 30.

1.3 Cloning Strategy

The synthetic gene may be cloned, e.g. by means of a restriction enzyme hydrolysis into a suitable expression vector.

2. Manufacture of a Single-Chain TRAIL Fusion Protein (Sc TRAIL Wt)

2.1 Polypeptide Structure
A) Amino acids Met1-Gly20
   Ig-Kappa-signal peptide, assumed signal peptidase cleavage site after amino acid Gly 20.
B) Amino acids Gln21-Gly182
   First soluble cytokine domain of the human TRAIL ligand (TRAIL, amino acid 120-281 of SEQ ID NO:10)
C) Amino acids Gly183-Ser 190
   First peptide linker element, wherein the two amino acids designated X are both S or one is S and the other one is N.
D) Amino acids Arg191-Gly351
   Second soluble cytokine domain of the human TRAIL ligand (TRAIL, amino acids 121-281 of SEQ ID NO:10)
E) Amino acids Gly 352-Ser359
   Second peptide linker element wherein the two amino acids designated X are both S or one is S and the other one is N.

F) Amino acids Arg360-Gly520
Third soluble cytokine domain of the human TRAIL ligand (TRAIL, amino acids 121-Gly281 of SEQ ID NO:10).
G) Amino acids Gly521-Lys538
Peptide linker element with a Streptag II motif.

The amino acid sequence of sc TRAIL wt is shown in SEQ ID NO: 28.

The indicated linkers may be replaced by other preferred linkers, e.g. as shown in SEQ ID NOs: 21.26. It should be noted that the first and second peptide linkers do not need to be identical.

The signal peptide sequence (A) may be replaced by any other suitable, e.g. mammalian signal peptide sequence. The Strep-tag II motif (G) may be replaced by other motifs, if desired, or deleted.

Cell culture supernatants of HEK293 cells, transiently expressing single chain TRAIL proteins with different linkers (derived from SEQ ID 28, in total nine different linker combinations) were collected and used to stimulate Jurkat cells at varying dilutions (exemplarily, a dilution of 1:8 is shown in FIG. 25). The supernatants were used either directly without further modifications or an anti-Streptag antibody (2 microgram/ml Strep MAB Immo) was added to cross-link the scTRAILwt proteins. Jurkat cells were incubated with HEK293 cell culture supernatant for three hours at 37°, lysed and analysed for caspase activity. Cell culture supernatant that contained cross-linked scTRAILwt proteins induced an increased caspase activity in Jurkat cells (results shown on the right hand side of the graph), indicating that scTRAILwt proteins alone do form only a low amount of higher order aggregates able to be pro-apoptotic.

2.2 Gene Cassette Encoding the Polypeptide

The synthetic gene may be optimised in view of its codon usage for the expression in suitable host cells, e.g. insect cells or mammalian cells. A preferred nucleic acid sequence is shown in SEQ ID NO: 31.

3. Manufacture of a Single-Chain Mutated TRAIL Fusion Protein (scTRAIL (R2-Specific))

In the following, the structure of a single-chain TRAIL polypeptide comprising a mutation for selective binding to TRAIL receptor R2 is shown.

3.1 Polypeptide Structure
A) Amino acids Met1-Ser29
Ig-Kappa signal peptide, assumed signal peptidase cleavage site after amino acid Gly20 and peptide linker
B) Amino acids Arg29-Gly190
First soluble cytokine domain of the human TRAIL ligand (TRAIL, amino acids 121-281 of SEQ ID NO: 10 including the mutations Y189Q, R191K, Q193R, H264R, I266L and D267Q)
C) Amino acid Gly191-Ser198
First peptide linker element, wherein the amino acids designated X are as indicated in Example 2
D) Amino acids Arg199-Gly359
Second soluble cytokine domain of the human TRAIL ligand (TRAIL amino acids 121-281 of SEQ ID NO: 10 including the mutations as indicated in B)
E) Amino acids Gly360-Ser367
Second peptide linker element, wherein the amino acids X are as indicated in Example 2
F) Amino acids Arg368-Gly528
Third soluble cytokine domain of the human TRAIL ligand (TRAIL, amino acids 121-281 of SEQ ID NO: 10 including the mutations as indicated in B)
G) Amino acids Gly529-Lys546
Peptide linker with a Strep-tag II motif The amino acid sequence of scTRAIL(R2-specific) is shown in SEQ ID NO: 29.

The indicated linkers may be replaced by other preferred linkers, e.g. as shown in SEQ ID NOs: 21-26. It should be noted that the first and second peptide linkers do not need to be identical.

The signal peptide sequence (A) may be replaced by any other suitable, e.g. mammalian signal peptide sequence. The Streptag II motif (G) may be replaced by other motifs, if desired, or deleted.

3.2 Gene Cassette Encoding the Polypeptide

The synthetic gene may be optimised in view of its codon usage for the expression in suitable host cells, e.g. insect cells or mammalian cells. A preferred nucleic acid sequence is shown in SEQ ID NO: 32.

4. Expression and Purification a) Cloning, Expression and Purification of Fusion Polypeptides Hek293T cells grown in DMEM+GlutaMAX (GibCo) supplemented with 10% FBS, 100 units/ml Penicillin and 100 μg/ml Streptomycin were transiently transfected with a plasmid containing an expression cassette for a fusion polypeptide. In those cases, where a plurality of polypeptide chains is necessary to achieve the final product, e.g. for the Fab-scTNF-SF fusion proteins (FIG. 9A), the expression cassettes were either combined on one plasmid or positioned on different plasmids during the transfection. Cell culture supernatant containing recombinant fusion polypeptide was harvested three days post transfection and clarified by centrifugation at 300×g followed by filtration through a 0.22 μm sterile filter. For affinity purification Streptactin Sepharose was packed to a column (gel bed 1 ml), equilibrated with 15 ml buffer W (100 mM Tris-HCl, 150 mM NaCl, pH 8.0) or PBS pH 7.4 and the cell culture supernatant was applied to the column with a flow rate of 4 ml/min. Subsequently, the column was washed with 15 ml buffer W and bound polypeptide was eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step. The protein amount of the eluate fractions was quantitated and peak fractions were concentrated by ultrafiltration and further purified by size exclusion chromatography (SEC).

SEC was performed on a Superdex 200 column using an Akta chromatography system (GE-Healthcare). The column was equilibrated with phosphate buffered saline and the concentrated, Streptactin-purified polypeptide was loaded onto the SEC column at a flow rate of 0.5 ml/min. The elution profile of the polypeptide was monitored by absorbance at 280 nm.

For determination of the apparent molecular weight of purified fusion polypeptide under native conditions a Superdex 200 column was loaded with standard proteins of known molecular weight. Based on the elution volume of the standard proteins a calibration curve was plotted and the apparent molecular weight of purified fusion polypeptide was determined.

5. Apoptosis Assay

A cellular assay with a Jurkat A3 permanent T-cell line was used to determine the apoptosis inducing activity of different CD95-ligand (CD95L) and TRAIL fusion polypeptide constructs. Jurkat cells were grown in flasks with RPMI 1640-medium+GlutaMAX (GibCo) supplemented with 10% FBS, 100 units/ml Penicillin and 100 μg/ml Streptomycin. Prior to the assay, 100,000 cells were seeded per well into a 96-well microtiterplate. The addition of different concentrations of fusion peptides to the wells was followed by a 3 hour incubation at 37° C. Cells were lysed by adding lysis buffer (250 mM HEPES, 50 mM $MgCl_2$, 10 mM EGTA, 5% Triton-X-100, 100 mM DTT, 10 mM AEBSF, pH 7.5) and plates were put on ice for 30 minutes to 2 hours. Apoptosis is paralleled by an increased activity of caspases, e.g. Caspase-3. Hence, cleavage of the specific caspase substrate Ac-DEVD-AFC (Biomol) was used to determine the extent of apoptosis. In fact, Caspase activity correlates with the percentage of apoptotic cells determined morphologically after staining the cells with propidium iodide and Hoechst-33342. For the caspase activity assay, 20 µl cell lysate was transferred to a black 96-well microtiter plate. After the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan Infinite 500 microtiter plate reader and the increase in fluorescence intensity was monitored (excitation wavelength 400 nm, emission wavelength 505 nm).

5.1 Cell Death Assay

For the determination of cell death in HT1080 fibrosarcoma cells 15,000 cells were plated in 96-well plates overnight in RPMI 1640-medium+GlutaMAX (GibCo) supplemented with 10% FBS (Biochrom). Cells were coincubated with cycloheximide (Sigma) at a final concentration of 2.5 µg/ml. Cell death was quantified by staining with buffer KV (0.5% crystal violet, 20% methanol). After staining, the wells were washed with water and air-dried. The dye was eluted with methanol and optical density at 595 nm was measured with an ELISA reader.

6. Stability/Aggregation Test 6.1. Principle of the Aggregation Analysis (Definition for Soluble Protein)

The content of monomers (defined trimeric assembly of TNF-SF receptor binding modules) and aggregates is determined by analytical SEC as described in Example 4. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight.

Based on the elution volume of the standard proteins a calibration curve is plotted and the apparent molecular weight of purified fusion polypeptide is calculated based on the elution volume.

SEC analysis of soluble, non-aggregated proteins,—e.g. trimeric TNF-SF, typically shows a distinct single protein peak at a defined elution volume. This elution volume corresponds to the apparent native molecular weight of the particular protein and approximately complies to the theoretical molecular weight calculated on the basis of the primary amino acid sequence. If protein aggregation occurs the SEC analysis shows additional protein peaks with lower retention volumes. For TNF-SF family members the aggregation of soluble proteins occurs in a characteristic manner. The proteins tend to form oligomers of the "trimers", forming nonamers (3×3) and 27 mers (3×9). These oligomers serve as aggregation seeds and a high content of oligomers potentially leads to aggregation of the protein. Oligomers of large molecular weight and aggregates elute in the void volume of the Superdex200 column and cannot be analysed by SEC with respect to their native molecular weight. Examples for SEC analysis of a defined soluble trimeric and a oligomerized/aggregated preparation of TNF-SF proteins are shown in FIG. 17.

Due to the induction of (complete) aggregation, purified preparations of TNF-SF fusion proteins should preferably contain only defined trimeric proteins and only a very low amount of oligomerized protein.

The degree of aggregation/oligomerisation of a particular TNF-SF protein preparation is determined on basis of the SEC analysis by calculating the peak areas of the OD280 diagram for the defined trimeric and the oligomer/aggregate fraction, respectively. Based on the total peak area the percentage of defined trimeric protein is calculated as follows:

(% Trimer content=[Peak area trimer]/
[Total peak area]×100)

The definition for soluble protein as used in this text, describes a protein preparation of purified TNF-SF protein in a buffer of physiological salt concentrations at physiological pH that contains a defined soluble protein (trimeric assembly of TNF-SF domains) content of >90% within a typical protein concentration range from 0.2 to 10.0 mg/ml.

6.2 SEC Aggregation Analysis for Purified Sc-TRAIL Variants

Three different sc-TRAIL variants were transfected and affinity purified as described. The purified proteins were subsequently analysed for their content of defined soluble protein using SEC analysis as described in 6.1. In the particular case of single chain fusion proteins a trimer describes a trimeric assembly of three encoded TNF-SF domains encoded by a single polypeptide chain. (Formally single chain TNF-SF proteins are monomers, since single chain assemblies do only form intramolecular interactions [all protein domains are encoded by a single polypeptide chain] and do not form intermolecular interactions between distinct individual polypeptide chains.)

The proteins analysed by SEC were:

1.) Fab-sc-TRAIL(R2-specific)-SNSN (FIG. 19):
   Fusion protein comprising an Fab domain fused N-terminal to a single chain fusion protein of TRAIL specific for TRAIL-receptor 2 interaction, glycosylated 2.) Fab-sc-TRAIL(R2-specific)-SSSS (FIG. 18)
   Fusion protein comprising an Fab domain fused N-terminal to a single chain fusion protein of TRAIL specific for TRAIL-receptor 2 interaction, non-glycosylated 3.) Fab-sc-TRAIL-wt-SNSN (FIG. 20):
   Fusion protein comprising a Fab domain fused N-terminal to a single chain TRAIL, glycosylated The SEC analysis for the three purified Fab-sc-constructs of TRAIL revealed a single protein peak for all proteins indicating defined soluble protein fractions (>95% trimer). The calculated apparent MW for the proteins (based on calibration of the column) strongly indicate a trimeric association of the TNF-SF-domains for the purified proteins. None of the analysed proteins showed indications for aggregation (FIGS. 18, 19, 20).

Comparing the potentially glycosylated "Fab-sc-TRAIL-R2-SNSN" with the non glycolsylated "Fab-sc-TRAIL-R2-SSSS" indicates a significant difference of the apparent native MW that is due to glycosylation of Fab-sc-TRAIL (R2-specific)-SNSN.

Expression of sc-TNF-SF members as fusion protein with an antibody fv-fragment is known to facilitate aggregation of the protein. The construction principle of the Fab-sc-TRAIL variants revealed no aggregation of the expressed TRAIL variants and is therefore beneficial with respect to solubility of the protein.

6.3 Differential Glycolsylation of Sc-TRAIL-Linker Variants

Figure 22:
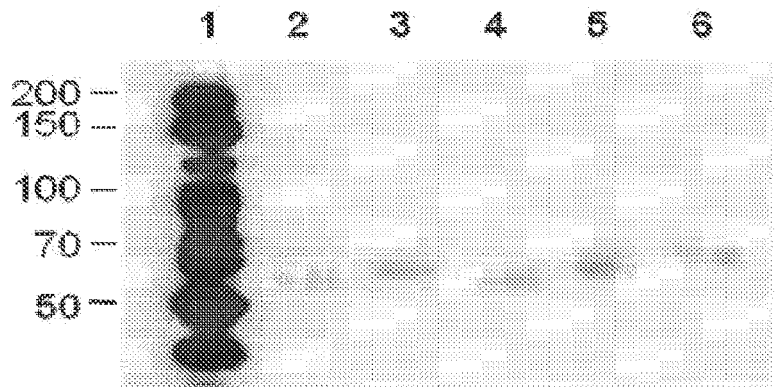

Glycosylation of proteins can be beneficial for recombinant sc-TNF-SF constructs with regard to potential immunogenicity and stability. In order to get glycosylation of the sc-TRAIL construct, specific linker sequences were designed that contained putative N-linked glycosylation sites at defined positions (see FIG. 21-A). Recombinant expression and subsequent Western-Blot analysis revealed that the respective position of the Asparagine (N) within the linker sequence is important for the subsequent glycosylation of the protein. Surprisingly, the preferential linker position of the glycosylated asparagine was identified to be at position "2" as described in FIG. 21-A, (G S G S G N G S, SEQ ID NO: 53). If the asparagine is localised at other positions (e.g. position "1" [G S G N G S G S] see FIG. 21-A), glycosylation of the respective asparagines(s) is abolished. This aspect could be confirmed by Western-Blot analysis of different sc-TRAIL variants. If both asparagines of linker 1 and linker 2 were localised at position"2" a significant glycosylation dependant MW-shift could be observed for the respective sc-TRAIL variant (FIG. 22). A MW-shift of the glycosylated sc-TRAIL linker variant could also be confirmed by calculating the apparent MW after SEC analysis (FIG. 18, 19). The non-glycosylated Fab-sc-TRAIL (R2-specific)SSSS has a clearly lower MW (68 kDa) compared to glycosylated Fab-sc-TRAIL(R2-specific)SNSN (87 kDa).

Based on this analysis we claim differential glycosylation of the sc-TRAIL constructs by modifying the position of the asparagines within the linker sequence(s). Glycosylation protects the linker sequence towards proteolytic degradation and might stabilise the protein. In addition glycosylation of the linker sequence potentially prevents recognition of the linker sequence by the immune system and potentially reduces the immunogenicity of the protein. Therefore glycosylation of the linker sequence is beneficial with regard to immunogenicity and proteolytic stability of the sc-TRAIL constructs and has potential influence on the half life of the protein. The linker specific differential glycosylation can be used to modify the immunogenicity and stability of recombinant TNF-SF members.

6.4. Expression and Analysis of a Sc-TRAIL with Prolonged Linker Sequence and N-Terminal Stalk Residues (Sc-TRAIL-(95-281)-Long)

In WO/2005/103077 a single chain TRAIL-fusion polypeptide, herein named sc-TRAIL-(95-281)-long, is described, wherein each TRAIL module comprises residues 95 to 281 of SEQ ID NO:10. The TRAIL modules are linked by Glycine Serine linker comprising of at least 12 amino acids (GGGSGGGSGGGS, SEQ ID NO: 103). Compared to the TRAIL modules of the present invention (comprising residues 121-281 of SEQ ID NO:10), additional 25 amino acids including the stalk region are present in each of the adjacent TRAIL modules.

In order to analyse the influence of the linker sequence on sc-TRIAL constructs, sc-TRAIL-(95-281)-long is analysed. Expression, purification and subsequent SEC analysis reveals that sc-TRAIL-(95-281)-long with the 12 aa linker and the additional stalk sequence is expressed and secreted to the cell culture supernatant of HEK293T cells. However, SEC analysis of the purified protein indicates that sc-TRAIL-(95-281)-long shows multiple peaks comprising a large amount of protein in an oligomerized or aggregated from. Aggregation of sc-TRAIL-(95-281)-long is a direct effect of the prolonged linker sequences in combination with the additional residues of the N-terminal stalk. The results indicate that the longer linker used in this construct leads to increased aggregation properties of the construct.

Figure 7:
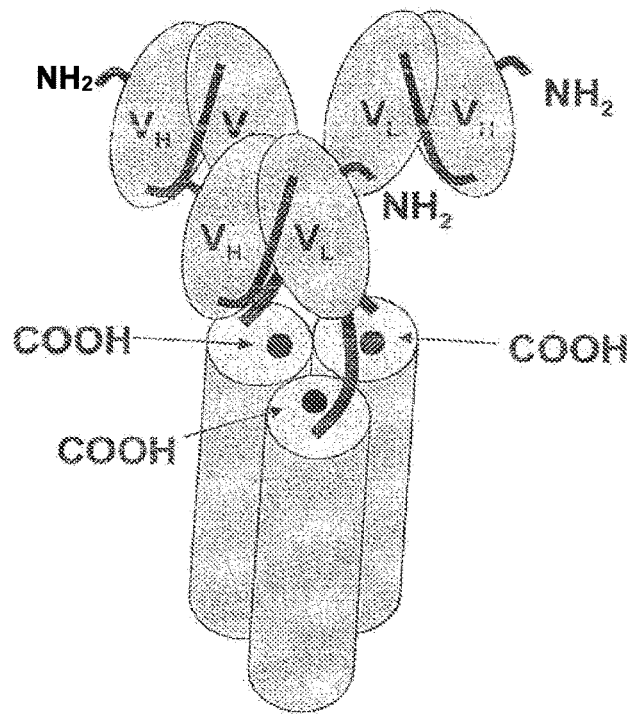
FIG. 7 scFv-TNF-SF fusion protein known from the art.

7. Construction of Single-Chain Fusion Polypeptides Comprising One or More Additional Domains 7.1. Assembly of Soluble TNF-SF and Antibody Fragments Known from the Art It is known from the art that soluble TNF-SF cytokine domains may be fused to antibody fragments in order to obtain trimerization and/or dimerization of trimers. Single-chain scFv-TNF-SF fusion proteins have been constructed consisting of a single-chain antibody and a soluble domain comprising a TNF-RBD and the stalk-region. The corresponding trimers consist of three single-chain antibodies and three soluble domains (FIG. 7).

Figure 8:
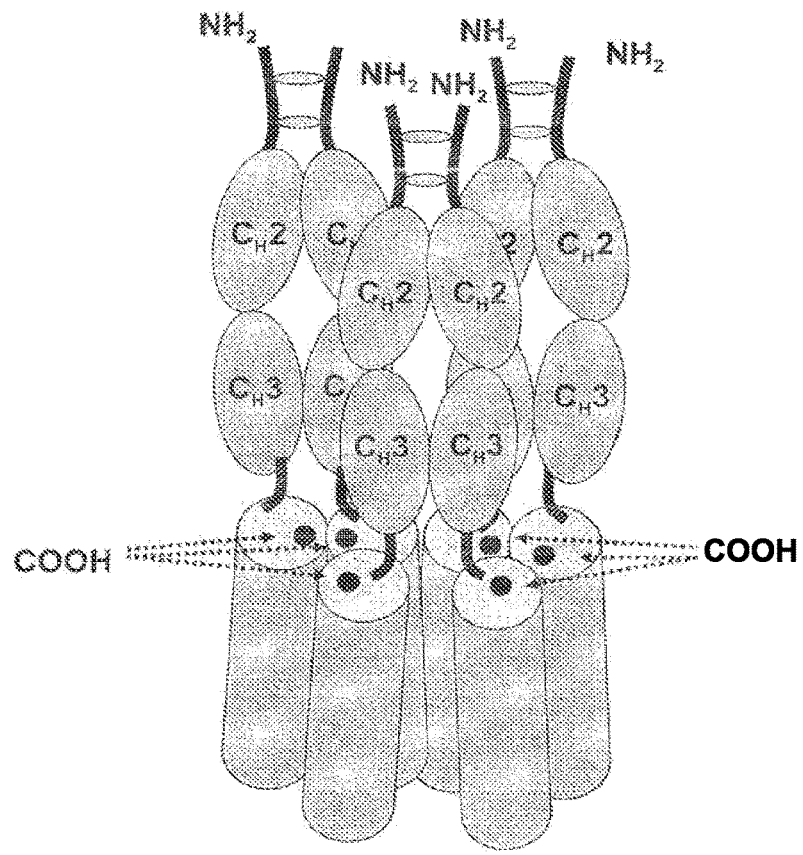
FIG. 8 Fc-TNF-SF fusion protein known from the art.

In addition, Fc-TNF-SF fusion proteins, wherein each fusion protein comprises an N-terminal intramolecular Fc-domain and a C-terminal soluble domain have been constructed (FIG. 8). The dimerization of soluble domains is accomplished by assembly of two Fc-domains via disulfide bridges. Trimers are subsequently obtained by a combination of two soluble domains from one Fc-TNF-SF fusion protein and one soluble domain from another Fc-TNF-SF fusion protein. As can be deduced from FIG. 4, dimerization of trimers is also mediated by the N-terminal Fc-TNF-SF fusion. In conclusion, three Fc-antibody fragments are present per dimer of the trimer. However, such fusion proteins are likely to form higher molecular weight aggregates, which represents a major disadvantage.

7.2 Fusion Proteins of the Invention Comprising One or More Additional Domains

The inventive fusion proteins comprising one or more additional domains can be constructed in several ways. In the following, the construction of fusion proteins with additional domains is exemplified with the antibody pertuzumab directed against the cell surface antigen ErbB2.

The amino acid sequence of the heavy chain is shown in SEQ ID NO: 33:

```
  1  EVQLVESGGG LVQPGGSLRL SCAASGFTFT DYTMDWVRQA PGKGLEWVAD VNPNSGGSIY

61  NQRFKGRFTL SVDRSKNTLY LQMNSLRAED TAVYYCARNL GPSFYFDYWG QGTLVTVSSA

121  STKGPSVFPL APSSKSTSGG TAALGCLVKD YFPEPVTVSW NSGALTSGVH TFPAVLQSSG

181  LYSLSSVVTV PSSSLGTQTY ICNVNHKPSN TKVDKKVEPK SC
```

The amino acid sequence of the light chain is shown in SEQ ID NO: 34

```
  1  DIQMTQSPSS LSASVGDRVT ITCKASQDVS IGVAWYQQKP GKAPKLLIYS ASYRYTGVPS

61  RFSGSGSGTD FTLTISSLQP EDFATYYCQQ YYIYPYTFGQ GTKVEIKRTV AAPSVFIFPP

121  SDEQLKSGTA SVVCLLNNFY PREAKVQWKV DNALQSGNSQ ESVTEQDSKD STYSLSSTLT

181  LSKADYEKHK VYACEVTHQG LSSPVTKSFN RGEC
```

7.2.1

Figure 9:
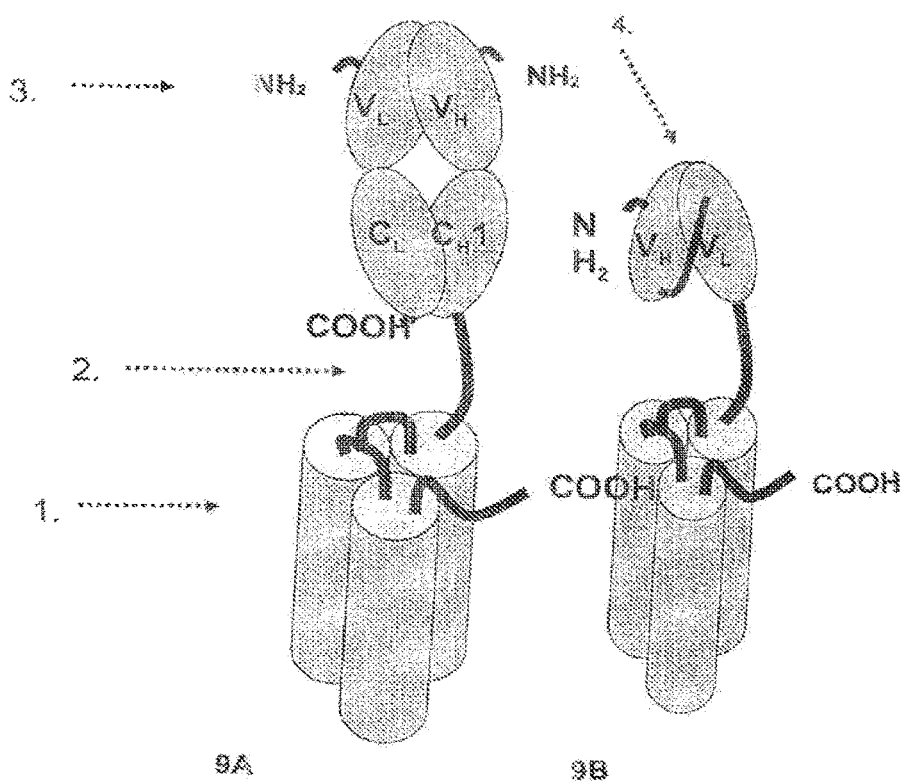

In one embodiment, the fusion polypeptide of the invention further comprises an N- or C-terminal Fab-antibody fragment (FIG. 9A).

The fusion of an antibody Fab-fragment to the N-terminus of scTNF-SF fusion polypeptide may be accomplished by the following two strategies:

(i) The heavy chain sequence is extended by further amino acids from the IgG1 hinge region and fused to the single-chain TNF-SF fusion protein.

The IgG1 hinge region comprises the amino acid sequence SEQ ID NO: 35:

... KS c.DKTHT c.PP c.PAPE ...

In a preferred embodiment, the Fab-domain is chosen such that the C-terminal cysteine of the heavy chain (C1 of the hinge region) terminates the CH1 domain. This cysteine is required for forming a disulfide linkage to the light chain.

The subsequent linker comprises portions of the IgG hinge region (e.g. DKTHT or DKT), however without further cysteines of the hinge region. Alternatively, a glycine/serine inker is used. Due to the absence of further cysteines, a monomeric fusion protein comprising two polypeptide chains is obtained. The linker preferably has a length of 3-15 amino acids. More preferably, the linker is selected from the linker 1-7 as shown below.

```
                                           SEQ ID NOs: 55-56
1. DKTHTG(S)a(G)b;
(a = 0-5; b = 0 or 1),

SEQ ID NOs: 57-61
2. DKTHTGS(S)a(GS)bG(S)c
(a, b = 0, 1-6; c = 0 or 1),

SEQ ID NO: 62
3. DKTG(S)a(G)b;
(a = 0-5; b = 0 or 1),

SEQ ID NOs: 63-67
4. DKTG(S)a(GS)bG(S)c
(a, b = 0, 1-6; c = 0 or 1),

SEQ ID NOs: 68-69
5. SSG(S)a(GS)bG(S)c
(a, b = 0, 1-6; c = 0 or 1),

SEQ ID NO: 71
6. SS(GGGS)aG(S)b
(a = 0, 1-4; b = 0 or 1),

SEQ ID NO: 72
7. GSPGSSSSSS(G)a
(a = 0 or 1),
```

Preferred amino acid sequences with the heavy chain module positioned N-terminal to the scTNF-SF module are shown in SEQ ID NO: 45, SEQ ID NO: 47 and SEQ ID NO: 49. For production purposes, these polypeptide chains are co-expressed with the Fab light chain polypeptide (SEQ ID NO: 40) to finally achieve the Fab-scTRAIL fusion polypeptides.

(ii) The light-chain sequence is fused to the single chain TNF-SF fusion protein.

The constant region of the light chain (e.g. SEQ ID NO: 34) ends with a C-terminal cysteine residue. This residue may be covalently bridged with the C1 hinge cysteine of the heavy chain. Preferably, the linkers 1-7 as shown below are used for the connection between the light chain sequence and the TNF-SF fusion protein. Linkers 5-7 are preferred (see above).

Preferably, the last amino acid in the linker adjacent to the cytokine module is either Gly or Ser. In the following, preferred linker sequences are shown:

Further, the linker may comprise N-glycosylation motifs (NXS/T, wherein X may be any amino acid).

One embodiment of the amino acid sequences with the light chain module positioned N-terminal to the scTNF-SF module is shown in SEQ ID NO: 51.

In the case of the Fab-scTNF-SF fusion proteins, the co-expression of two polypeptide chains is necessary to achieve the correct assembly of the Fab module in addition to the scTNF-SF module (see FIG. 9A). The Pertuzumab heavy and light chain modules (SEQ ID NO: 33 and SEQ ID NO: 34) were equipped with a signal peptide, back translated and the resulting synthetic genes (SEQ ID NO: 41 and SEQ ID NO: 42) genetically fused upstream of the scTRAILwt- or scTRAILR2-specific gene modules (SEQ ID NO: 31 and SEQ ID NO: 32). Examples for the resulting gene cassettes are shown in SEQ ID NO: 46, 48 and 50. After subcloning into appropriate expression vectors, a selection of the resulting plasmids was used for transient protein expression in HEK293T cells. The heavy chain TRAIL or light chain TRAIL expression plasmids were transfected either alone or in combination with the necessary light or heavy chain encoding vectors of the Fab-Fragment (FIG. 26). Surprisingly, the module combination within the fusion proteins influenced the relative stability of the scTRAIL-protein during secretory based expression. If the light-chain module of the Fab-domain is fused N-terminal to the scTRAIL-domain (exemplified in SEQ ID NO: 51), the expression product is stable itself and secreted, when expressed separately (Lanes 1-4, FIG. 26). It can be therefore expected, when such a fusion polypeptide is co-expressed with a heavy-chain module, that two major protein species will be formed during a potential production process: (1) the Fab-scTRAIL fusion protein consisting of two polypeptide chains and (2) as contamination a light-chain-scTRAIL fusion protein without a functional Fab domain.

Therefore, fusing the heavy-chain module N-terminal to the scTNF-SF-module for the expression is preferred to avoid this technical disadvantage.

A functional analysis of recombinant inventive Fab comprising-scTRAIL fusion proteins with the heavy-chain module fused N-terminal to the scTRAIL-module (Fab-scTRAILR2-SNSN or Fab-scTRAILwt-SNSN) is shown in FIG. 28. As final purification step, size exclusion chromatography was employed as exemplified in FIGS. 19 and 20.

Superior bioactivity compared to soluble, homotrimeric ligands can easily be achieved by the use of artificially cross-linked or a membrane-bound ligand of the TNF superfamily. Thus the local enrichment of single chain TRAIL (scTRAIL) constructs on cells that express the antigen Her2 via the Her2-selective Fab-fragment ("Pertuzumab") fused to these scTRAIL proteins should increase their cytotoxic bioactivity. Likewise, the blocking of the Her2 binding sites on cells by pre-incubation with the Her2-specific Fab-fragment (Pertuzumab-Fab) only should decrease the cytotoxic bioactivity of Fab-scTRAIL fusion proteins. As shown in FIG. 28A, scTRAIL constructs induce the death of HT1080 cells, as the viability decreases with increasing protein concentration. In accordance, the pre-incubation of HT1080 cells with the Fab-fragment (Pertuzumab-Fab), followed by co-incubation with the Fab-scTRAIL constructs (Fab-scTRAILR2-SNSN or Fab-scTRAILwt-SNSN) overnight, reduced the cytotoxic activity of the Fab-scTRAIL constructs (FIG. 28B), whereas the Fab only induced no cell death.

An increased technical effect may be achieved by use of artificially cross-linked or membrane-bound ligands of the TNF superfamily resulting especially in superior bioactivity as compared to soluble, homotrimeric ligand. Thus the local enrichment of ligands or single chain ligands such as exemplified by single chain TRAIL (scTRAIL) on cells or on neighbouring cells should increase the bioactivity of these fusion proteins. The local enrichment (or targeting) of these single chain ligands can be specifically induced for instance by fusing the single chain ligands with amino acid sequences that bind to any antigen present on cells such as for instance tumor cells. Examples for antigen binding sequences may be derived from antibodies such as scFv or Fab fragments. Examples for antigens expressed on target cells may be receptors such as from the EGFR family or any other antigen to which a binding antibody can be generated. Of special interest in this context are cell surface antigens specific for tumor or cancer cells.

7.2.2

In another embodiment, the fusion polypeptide of the invention further comprises an additional N- or C-terminal scFv-antibody fragment (FIG. 9B).

In this embodiment linkers 5-7 as described above may be used. Further, the linkers may comprise N-glycosylation motifs.

A preferred single chain Fv-pertuzumab fragment for fusing to the single-chain cytokine fusion protein may comprise amino acids Glu1-Ser119 of SEQ ID NO: 33 and Asp-Lys107 or Thr109 of SEQ ID NO: 34. The VH and VL fragments may be connected by a linker.

One embodiment of a scFv-domain of pertuzumab is shown in the following SEQ ID NO: 36:

```
  1  METDTLLLWV LLLWVPAGNG EVQLVESGGG LVQPGGSLRL SCAASGFTFT DYTMDWVRQA
 61  PGKGLEWVAD VNPNSGGSIY NQRFKGRFTL SVDRSKNTLY LQMNSLRAED TAVYYCARNL
121  GPSFYFDYWG QGTLVTVSSG GGGSGGGGSG GGGSDIQMTQ SPSSLSASVG DRVTITCKAS
181  QDVSIGVAWY QQKPGKAPKL LIYSASYRYT GVPSRFSGSG SGTDFTLTIS SLQPEDFATY
241  YCQQYYIYPY TFGQGTKVEI KRT
```

Amino acids 1-20 (underlined) constitute an N-terminal secretory signal peptide.

7.2.3

In a further embodiment, the fusion polypeptide of the invention comprises an additional N- or C-terminal Fc-antibody fragment (FIGS. 10 and 11).

Preferably, the Fc-antibody fragment domain is derived from a human immunoglobulin G heavy chain, particularly from a human immunoglobulin IgG1 heavy chain. In an especially preferred embodiment, the amino acid sequence of the Fc-domain is shown in SEQ ID NO: 37.

```
  1  KSCDKTHTCP PCPAPELLGG PSVFLFPPKP KDTLMISRTP EVTCVVVDVS HEDPEVKFNW
 61  YVDGVEVHNA KTKPREEQYN STYRVVSVLT VLHQDWLNGK EYKCKVSNKA LPAPIEKTIS
121  KAKGQPREPQ VYTLPPSREE MTKNQVSLTC LVKGFYPSDI AVEWESNGQP ENNYKTTPPV
181  LDSDGSFFLY SKLTVDKSRW QQGNVFSCSV MHEALHNHYT QKSLSLSPGK
```

Amino acids Lys1-Glu16 define the hinge region.

For a C-terminal fusion (FIG. 11) the Fc-domain preferably comprises the complete constant domain (amino acids 17-230 of SEQ ID NO: 37) and a part or the complete hinge region, e.g. the complete hinge region or the hinge region starting from amino acid Asp4.

Preferred linkers for connecting a C-terminal Fc-antibody fragment (e.g. FIG. 11) are shown in the following:

```
Linker 8
                                          SEQ ID NOs: 73-78
scCD95L/scTRAIL . . . GG(P/S)_a(GS)_b(G/S)_c KSCDKTHTC
PPCPAPE . . .
(a = 0 or 1; b = 0-8; c = 0-8),
```

```
Linker 9
                                    SEQ ID NOs: 79-80
scCD95L/scTRAIL . . . GG(P/S)_a(GSSGS)_bGS(G/S)_c DKTH TCPPCPAPE . . .
(a = 0 or 1; b = 0-8; c = 0-8), Linker 10
                                    SEQ ID NOs: 81-82
scCD95L/scTRAIL . . . GG(P/S)_a(S)_b(GS)_c(G/S)_d DKTHT CPPCPAPE . . .
(a = 0 or 1; b = 0-8; c = 0-8; d = 0-8),
```

All linkers start with GlyGly taking in account, however, that the C-terminal amino acid of TRAIL is a Gly. At position 3 of the linker, alternatively Pro or Ser are present. Linker 8 comprises the Cys1 cysteine of the heavy chain.

It should be noted that linkers 8-10 are also suitable for the C-terminal fusion of other polypeptides, e.g. a further scTNF-SF fusion protein.

In detail, the scTRAILwt module (SEQ ID NO: 28), the scTRAIL(R2-specific)-module (SEQ ID NO: 29) and the scCD95L-module (SEQ ID NO: 27) were fused N-terminally to the Fc-domain of human IgG1, starting with Asp4 of SEQ ID NO: 37 employing four linker elements as shown in Table 1.

TABLE 1

Sequences linking the Fc-domain C-terminally to scTNF-SF module. The N-terminal amino-acid of the IgG1 CH2-domain is underlined. The N-terminal Glycine of the linking sequence is shown in brackets. For TNF-SF proteins with a glycine as the C-terminal amino acid (e.g. TRAIL), the N-terminal glycine of the linking sequence formally belongs to the scTNF-SF module.

| Fc-Fusion | Amino-acid sequence of the linker element |
|---|---|
| FC01 | . . . (G)GSPGSSSSSSGS<u>D</u>KTH . . . SEQ ID NO: 97 |
| FC02 | . . . (G)GSPGSSSSGS<u>D</u>KTH . . . SEQ ID NO: 98 |
| FC03 | . . . (G)GSPGSSGS<u>D</u>KTH . . . SEQ ID NO: 99 |
| FC04 | . . . (G)GSS<u>D</u>KTH . . . SEQ ID NO: 100 |

For purification and characterisation, a Strep-tag II (amino acid sequence WSHPQFEK, SEQ ID NO: 102) was placed C-terminally to the Fc-domain. This affinity tag was linked to the CH3-domain by a flexible linker element (amino acid sequence SSSSSSA, SEQ ID NO: 101), replacing the C-terminal lysine residue of the CH3-sequence. The amino acid sequences of the scTNF-SF fusion proteins as well as for the described protein modules were backtranslated and their codon usage was optimised for mammalian cell-based expression. Gene synthesis was done by ENTELECHON GmbH (Regensburg, Germany). The expression cassettes for larger fusion proteins were assembled by common cloning procedures starting with DNA-modules of suitable size and suitable restriction enzyme pattern. Exemplarily, the resulting gene cassette for the single chain TRAILwt FC01 fusion protein (scTRAILwt-FC01) is shown in SEQ ID NO: 44 and the encoded protein sequence is shown in SEQ ID NO: 43. The gene cassettes encoding the shortened linker variants (table 1) were generated by PCR based subcloning strategies, starting from SEQ ID NO: 44. The final expression cassettes were released from intermediate cloning vectors and subcloned into to pCDNA4-HisMax-backbone, using unique Hind-III-, Not-I- or Xba-I sites of the plasmid. For the assembly of the Fab- and Fc-fusions proteins, a unique SgS-I site was introduced into the vector backbone, replacing the Not-I-site. All expression cassettes were routinely verified by DNA sequencing.

The proteins were transiently expressed in HEK293T cells and the cell culture supernatants were monitored regarding their pro-apoptotic activity. As shown in FIG. 27, the scTRAIL-Fc fusion proteins of the invention, were able to induce a pronounced increase in caspase activity, confirming the potency of the Fc-based dimerization of two scTRAILwt-modules. Similar results were obtained for scTRAIL(R2-specific)-Fc fusion proteins (data not shown).

If an Fc-antibody fragment is fused to the N-terminus of an scTNF-SF fusion protein (cf. FIG. 10), the amino acid sequence of the Fc-module is preferably as shown in SEQ ID NO: 38:

```
  1  METDTLLLWV LLLWVPAGNG DKTHTCPPCP APELLGGPSV FLFPPKPKDT LMISRTPEVT

61  CVVVDVSHED PEVKFNWYVD GVEVHNAKTK PREEQYNSTY RVVSVLTVLH QDWLNGKEYK

121  CKVSNKALPA PIEKTISKAK GQPREPQVYT LPPSREEMTK NQVSLTCLVK GFYPSDIAVE

181  WESNGQPENN YKTTPPVLDS DGSFFLYSKL TVDKSRWQQG NVFSCSVMHE ALHNHYTQKS

241  LSLSPG
```

Amino acids 1-20 (underlined) constitute an N-terminal secretory signal peptide.

For connecting the Fc-module to the ScTNF-SF fusion protein, preferably Gly/Ser linkers are used. All linkers preferably start with a serine and preferably end with glycine or serine. Preferred linker sequences 11-12 are shown in the following:

11. $(S)_a(GS)_b G(S)_c$ (a, b=0,1-6; c=0 or 1), SEQ ID Nos: 83-85

12. $S(GGGS)_a G_b(S)_c$ (a, b=0,1-6; c=0 or 1), SEQ ID NO: 86

7.3 Dimerization of the Single-Chain Fusion Proteins of the Invention 7.3.1 Single-Chain Fusion Polypeptides Comprising One Additional Domain The trimeric fusion proteins of the invention can further be dimerized.

In one embodiment, dimerization will be obtained if the C-terminus of a first fusion protein is directly connected to the N-terminus of a second fusion protein via a linker structure as defined herein (FIG. 12).

In another embodiment, a fusion protein of the invention comprising an Fab-antibody fragment as an additional domain, may be connected via a linker as defined herein directly with a further fusion protein of the invention or indirectly via a scFv-antibody fragment fused to a further fusion protein of the invention (FIG. 13). Thereby, dimerization of the trimeric fusion proteins of the invention is accomplished.

In another embodiment, dimerization of trimers may be obtained via the assembly of two fusion proteins of the invention comprising a Fab-antibody fragment as an additional domain (FIG. 14). In this case, intermolecular disulfide bridges are formed.

For the construction of dimerizing Fab fragments N-terminal to the scTNF-SF domain (e.g. FIG. 14), preferably the natural cysteine residues of the IgG hinge region (SEQ ID NO: 35) are used. Preferably the C-terminal cysteine of the Fab-sequence corresponds to the C1-residue of the hinge region, which forms a disulfide bond with the light chain. The second cysteine C2 may be used for the covalent linkage of two Fab-modules. A third cysteine residue C3 may be open or linked with the C3 of the neighbouring chain. Preferred linkers between the Fab heavy chain sequence and the N-terminus of the scTNF-SF domain are linkers 13-22 as shown below.

13. DKTHT$\underline{C}$ PGSS(GS)$_a$G(S)$_b$, SEQ ID NO: 87

14. DKTHT$\underline{C}$ PGSS$_a$G(S)$_b$, SEQ ID NO: 88

15. DKTHT$\underline{C}$(GSSGS)$_a$GSG(S)$_b$, SEQ ID NO: 89

16. DKTHT$\underline{C}$ GSS(GS)$_a$G(S)$_b$, SEQ ID NO: 90

17. DKTHT$\underline{C}$ GSS$_a$G(S)$_b$, SEQ ID NO: 91

18. DKTHT$\underline{C}$(GSSGS)$_a$GS(G)$_b$, SEQ ID NO: 92

19. DKTHT$\underline{C}$ PP$\underline{C}$ PGSSGSGSGS(G)$_b$, SEQ ID NO: 93

20. DKTHT$\underline{C}$ PP$\underline{C}$ P(GSSGS)$_a$GS(G)$_b$, SEQ ID NO: 94

21. DKTHT$\underline{C}$ PP$\underline{C}$ PGSS(GS)$_a$GS(G)$_b$, SEQ ID NO: 95

22. DKTHT$\underline{C}$PP$\underline{C}$PGSS$_a$GS(G)$_b$, SEQ ID NO: 96

Further, the linkers may be modified by incorporation of N-glycosylation motifs as described above.

In a further embodiment, dimerization of the fusion proteins of the invention comprising an Fc-antibody fragment as an additional N- and/or C-terminal domain, may be obtained by the formation of intermolecular disulfide bridges between two of said fusion proteins. In that case, only one Fc-antibody fragment is present per dimer of a trimeric fusion protein. Thereby, in contrast to the Fc-antibody fragment fusion proteins of the art, formation of higher molecular weight aggregates is not very likely.

7.3.2 Single-Chain Fusion Polypeptides Comprising a Plurality of Additional Domains The single-chain fusion polypeptide may comprise one or more additional domains, e.g. a further antibody fragment and/or a further targeting domain and/or a further cytokine domain.

A fusion protein of the invention comprising an Fc-antibody fragment as one additional domain may be connected to a further Fab- or scFv-antibody fragment via the N-terminus of an N-terminal fused Fc-antibody fragment (FIG. 15) or directly via its N-terminus through a further linker structure (FIG. 16), if the Fc-antibody fragment is connected to the fusion protein of the invention via its C-terminus.

In addition to a further antibody fragment or instead of the further antibody fragment, a further cytokine, preferably an interleukin, may be connected to the fusion protein. Thereby, it is possible to obtain a combination of an agonistic scCD95L and an antagonistic scCD95L molecule or alternatively combinations of scTRAIL (R1-specific) and scTRAIL (R2-specific).

Said fusion proteins are especially useful for the induction of apoptosis.

What is claimed is:

1. A single-chain fusion polypeptide comprising:
   (i) a first soluble LIGHT cytokine domain,
   (ii) a first peptide linker,
   (iii) a second soluble LIGHT cytokine domain,
   (iv) a second peptide linker, and
   (v) a third soluble LIGHT cytokine domain,
   wherein each of the soluble LIGHT cytokine domains lacks a stalk region.

2. The polypeptide of claim 1, wherein the first, the second, and the third soluble LIGHT cytokine domains are, independently an N-terminally shortened domain of SEQ ID NO:16, and optionally consists of an amino acid mutation.

3. The polypeptide of claim 1, wherein the first, the second, and the third soluble LIGHT cytokine domains independently have the amino sequence of 93-240 or 94-240 or 95-240 of SEQ ID NO: 16.

4. The polypeptide of claim 1, wherein the first and second peptide linkers are, independently, glycine/serine linkers.

5. The polypeptide of claim 4, wherein the glycine/serine linkers comprise substituted asparagine residues.

6. The polypeptide of claim 1, which additionally comprises an N-terminal signal peptide domain.

7. The polypeptide of claim 6, wherein the N-terminal signal peptide domain comprises a protease cleavage site.

8. The polypeptide of claim 1, which additionally comprises a further domain at the N-terminal and/or C-terminal end.

9. The polypeptide of claim 1, which additionally comprises a further domain and a third peptide linker at the C-terminal end.

10. An isolated nucleic acid molecule encoding the fusion polypeptide of claim 1.

11. An isolated host cell or a non-human organism transformed or transfected with the nucleic acid molecule of claim 10.

* * * * *

SEQUENCE LISTING

<160> NUMBER OF SEQ ID NOS: 103

<210> SEQ ID NO 1
<211> LENGTH: 205
<212> TYPE: PRT
<213> ORGANISM: Homo sapiens
<220> FEATURE:
<221> NAME/KEY: MISC_FEATURE
<223> OTHER INFORMATION: human LTA

<400> SEQUENCE: 1

Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 2
<211> LENGTH: 233
<212> TYPE: PRT
<213> ORGANISM: Homo sapiens
<220> FEATURE:
<221> NAME/KEY: MISC_FEATURE
<223> OTHER INFORMATION: human TNFa

<400> SEQUENCE: 2

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

```
Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
            165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230
```

<210> SEQ ID NO 3
<211> LENGTH: 244
<212> TYPE: PRT
<213> ORGANISM: Homo sapiens
<220> FEATURE:
<221> NAME/KEY: MISC_FEATURE
<223> OTHER INFORMATION: human LTA
<220> FEATURE:
<221> NAME/KEY: MISC_FEATURE
<223> OTHER INFORMATION: human LTB

<400> SEQUENCE: 3

```
Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
            35                  40                  45

Gln Asp Gln Gly Gly Leu Val Thr Glu Thr Ala Asp Pro Gly Ala Gln
50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
            115                 120                 125

Gln Asp Gly Leu Tyr Tyr Leu Tyr Cys Leu Val Gly Tyr Arg Gly Arg
130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
            210                 215                 220

His Pro Asp Met Val Asp Phe Ala Arg Gly Lys Thr Phe Phe Gly Ala
225                 230                 235                 240

Val Met Val Gly
```

<210> SEQ ID NO 4
<211> LENGTH: 183
<212> TYPE: PRT
<213> ORGANISM: Homo sapiens
<220> FEATURE:
<221> NAME/KEY: MISC_FEATURE
<223> OTHER INFORMATION: human OX40L

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 261
<212> TYPE: PRT
<213> ORGANISM: Homo sapiens
<220> FEATURE:
<221> NAME/KEY: MISC_FEATURE
<223> OTHER INFORMATION: human CD40L

<400> SEQUENCE: 5

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

```
Met Gln Lys Gly Asp Gln Asn Pro Gln Ile Ala Ala His Val Ile Ser
            115                 120                 125
Glu Ala Ser Ser Lys Thr Thr Ser Val Leu Gln Trp Ala Glu Lys Gly
        130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
            180                 185                 190
Leu Cys Leu Lys Ser Pro Gly Arg Phe Glu Arg Ile Leu Leu Arg Ala
        195                 200                 205
Ala Asn Thr His Ser Ser Ala Lys Pro Cys Gly Gln Gln Ser Ile His
    210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
            260

<210> SEQ ID NO 6
<211> LENGTH: 281
<212> TYPE: PRT
<213> ORGANISM: Homo sapiens
<220> FEATURE:
<221> NAME/KEY: MISC_FEATURE
<223> OTHER INFORMATION: human CD95L

<400> SEQUENCE: 6

Met Gln Gln Pro Phe Asn Tyr Pro Tyr Pro Gln Ile Tyr Trp Val Asp
1               5                   10                  15
Ser Ser Ala Ser Ser Pro Trp Ala Pro Pro Gly Thr Val Leu Pro Cys
            20                  25                  30
Pro Thr Ser Val Pro Arg Arg Pro Gly Gln Arg Arg Pro Pro Pro Pro
        35                  40                  45
Pro Pro Pro Pro Pro Leu Pro Pro Pro Pro Pro Pro Pro Pro Leu Pro
    50                  55                  60
Pro Leu Pro Leu Pro Pro Leu Lys Lys Arg Gly Asn His Ser Thr Gly
65                  70                  75                  80
Leu Cys Leu Leu Val Met Phe Phe Met Val Leu Val Ala Leu Val Gly
                85                  90                  95
Leu Gly Leu Gly Met Phe Gln Leu Phe His Leu Gln Lys Glu Leu Ala
            100                 105                 110
Glu Leu Arg Glu Ser Thr Ser Gln Met His Thr Ala Ser Ser Leu Glu
        115                 120                 125
Lys Gln Ile Gly His Pro Ser Pro Pro Pro Glu Lys Lys Glu Leu Arg
    130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
            180                 185                 190
Ser Lys Val Tyr Phe Arg Gly Gln Ser Cys Asn Asn Leu Pro Leu Ser
        195                 200                 205
```

```
His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                    245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 7
<211> LENGTH: 193
<212> TYPE: PRT
<213> ORGANISM: Homo sapiens
<220> FEATURE:
<221> NAME/KEY: MISC_FEATURE
<223> OTHER INFORMATION: human CD27L

<400> SEQUENCE: 7

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
        130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 8
<211> LENGTH: 234
<212> TYPE: PRT
<213> ORGANISM: Homo sapiens
<220> FEATURE:
<221> NAME/KEY: MISC_FEATURE
<223> OTHER INFORMATION: human CD30L

<400> SEQUENCE: 8

Met Asp Pro Gly Leu Gln Gln Ala Leu Asn Gly Met Ala Pro Pro Gly
1               5                   10                  15
```

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 9
<211> LENGTH: 254
<212> TYPE: PRT
<213> ORGANISM: Homo sapiens
<220> FEATURE:
<221> NAME/KEY: MISC_FEATURE
<223> OTHER INFORMATION: human CD137L

<400> SEQUENCE: 9

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

```
Phe Gln Leu Glu Leu Arg Arg Val Val Ala Gly Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 10
<211> LENGTH: 281
<212> TYPE: PRT
<213> ORGANISM: Homo sapiens
<220> FEATURE:
<221> NAME/KEY: MISC_FEATURE
<223> OTHER INFORMATION: human TRAIL

<400> SEQUENCE: 10

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
```

```
                            245                 250                 255
        Phe Val Ser Val Thr Asn Glu His Leu Ile Asp Met Asp His Glu Ala
                        260                 265                 270

Ser Phe Phe Gly Ala Phe Leu Val Gly
                        275                 280

<210> SEQ ID NO 11
<211> LENGTH: 317
<212> TYPE: PRT
<213> ORGANISM: Homo sapiens
<220> FEATURE:
<221> NAME/KEY: MISC_FEATURE
<223> OTHER INFORMATION: human RANKL

<400> SEQUENCE: 11

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
                20                  25                  30

Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
        50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315
```

<210> SEQ ID NO 12
<211> LENGTH: 249
<212> TYPE: PRT
<213> ORGANISM: Homo sapiens
<220> FEATURE:
<221> NAME/KEY: MISC_FEATURE
<223> OTHER INFORMATION: human TWEAK

<400> SEQUENCE: 12

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
        130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 13
<211> LENGTH: 247
<212> TYPE: PRT
<213> ORGANISM: Homo sapiens
<220> FEATURE:
<221> NAME/KEY: MISC_FEATURE
<223> OTHER INFORMATION: human APRIL_ver1

<400> SEQUENCE: 13

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

```
Leu Thr Gln Gln Thr Glu Leu Gln Ser Leu Arg Arg Glu Val Ser Arg
         50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
210                 215                 220

Leu Ser Val Ile Ile Pro Arg Ala Arg Ala Lys Leu Asn Leu Ser Pro
225                 230                 235                 240

His Gly Thr Phe Leu Gly Leu
                245

<210> SEQ ID NO 14
<211> LENGTH: 250
<212> TYPE: PRT
<213> ORGANISM: Homo sapiens
<220> FEATURE:
<221> NAME/KEY: MISC_FEATURE
<223> OTHER INFORMATION: human APRIL_ver2

<400> SEQUENCE: 14

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
 50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160
```

```
Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 15
<211> LENGTH: 285
<212> TYPE: PRT
<213> ORGANISM: Homo sapiens
<220> FEATURE:
<221> NAME/KEY: MISC_FEATURE
<223> OTHER INFORMATION: human BAFF

<400> SEQUENCE: 15

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
```

```
                    260                 265                 270
Asp Gly Asp Val Thr Phe Phe Gly Ala Leu Lys Leu Leu
            275                 280                 285

<210> SEQ ID NO 16
<211> LENGTH: 240
<212> TYPE: PRT
<213> ORGANISM: Homo sapiens
<220> FEATURE:
<221> NAME/KEY: MISC_FEATURE
<223> OTHER INFORMATION: human LIGHT

<400> SEQUENCE: 16

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 17
<211> LENGTH: 251
<212> TYPE: PRT
<213> ORGANISM: Homo sapiens
<220> FEATURE:
<221> NAME/KEY: MISC_FEATURE
<223> OTHER INFORMATION: human TL1A

<400> SEQUENCE: 17

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
```

```
                35                  40                  45
Gly Leu Thr Thr Tyr Leu Leu Val Ser Gln Leu Arg Ala Gln Gly Glu
 50                  55                  60

Ala Cys Val Gln Phe Gln Ala Leu Lys Gly Gln Glu Phe Ala Pro Ser
 65                  70                  75                  80

His Gln Gln Val Tyr Ala Pro Leu Arg Ala Asp Gly Asp Lys Pro Arg
                 85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 18
<211> LENGTH: 177
<212> TYPE: PRT
<213> ORGANISM: Homo sapiens
<220> FEATURE:
<221> NAME/KEY: MISC_FEATURE
<223> OTHER INFORMATION: human GITRL

<400> SEQUENCE: 18

Met Cys Leu Ser His Leu Glu Asn Met Pro Leu Ser His Ser Arg Thr
 1               5                  10                  15

Gln Gly Ala Gln Arg Ser Ser Trp Lys Leu Trp Leu Phe Cys Ser Ile
             20                  25                  30

Val Met Leu Leu Phe Leu Cys Ser Phe Ser Trp Leu Ile Phe Ile Phe
         35                  40                  45

Leu Gln Leu Glu Thr Ala Lys Glu Pro Cys Met Ala Lys Phe Gly Pro
 50                  55                  60

Leu Pro Ser Lys Trp Gln Met Ala Ser Ser Glu Pro Pro Cys Val Asn
 65                  70                  75                  80

Lys Val Ser Asp Trp Lys Leu Glu Ile Leu Gln Asn Gly Leu Tyr Leu
                 85                  90                  95

Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
130                 135                 140
```

-continued

```
Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser

<210> SEQ ID NO 19
<211> LENGTH: 391
<212> TYPE: PRT
<213> ORGANISM: Homo sapiens
<220> FEATURE:
<221> NAME/KEY: MISC_FEATURE
<223> OTHER INFORMATION: human EDA-A1

<400> SEQUENCE: 19

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
                20                  25                  30

Arg Ala Gly Glu Gly Asn Ser Cys Leu Leu Phe Leu Gly Phe Phe Gly
            35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320
```

```
Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
370                 375                 380

Leu Gly Glu Ala Pro Ala Ser
385                 390

<210> SEQ ID NO 20
<211> LENGTH: 389
<212> TYPE: PRT
<213> ORGANISM: Homo sapiens
<220> FEATURE:
<221> NAME/KEY: MISC_FEATURE
<223> OTHER INFORMATION: human EDA-A2

<400> SEQUENCE: 20

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Pro Asp Glu Lys
    130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285
```

```
Arg Ser Gly Glu Leu Glu Val Leu Val Asp Gly Thr Tyr Phe Ile Tyr
        290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
            340                 345                 350

Lys Ala Arg Gln Lys Ile Ala Val Lys Met Val His Ala Asp Ile Ser
        355                 360                 365

Ile Asn Met Ser Lys His Thr Thr Phe Phe Gly Ala Ile Arg Leu Gly
            370                 375                 380

Glu Ala Pro Ala Ser
385

<210> SEQ ID NO 21
<211> LENGTH: 8
<212> TYPE: PRT
<213> ORGANISM: Artificial Sequence
<220> FEATURE:
<223> OTHER INFORMATION: linker

<400> SEQUENCE: 21

Gly Gly Ser Gly Ser Gly Ser Gly
1               5

<210> SEQ ID NO 22
<211> LENGTH: 6
<212> TYPE: PRT
<213> ORGANISM: Artificial Sequence
<220> FEATURE:
<223> OTHER INFORMATION: linker

<400> SEQUENCE: 22

Gly Gly Ser Gly Ser Gly
1               5

<210> SEQ ID NO 23
<211> LENGTH: 4
<212> TYPE: PRT
<213> ORGANISM: Artificial Sequence
<220> FEATURE:
<223> OTHER INFORMATION: linker

<400> SEQUENCE: 23

Gly Gly Ser Gly
1

<210> SEQ ID NO 24
<211> LENGTH: 8
<212> TYPE: PRT
<213> ORGANISM: Artificial Sequence
<220> FEATURE:
<223> OTHER INFORMATION: linker

<400> SEQUENCE: 24

Gly Gly Ser Gly Asn Gly Ser Gly
1               5

<210> SEQ ID NO 25
<211> LENGTH: 8
<212> TYPE: PRT
<213> ORGANISM: Artificial Sequence
```

<220> FEATURE:
<223> OTHER INFORMATION: linker

<400> SEQUENCE: 25

Gly Gly Asn Gly Ser Gly Ser Gly
1               5

<210> SEQ ID NO 26
<211> LENGTH: 6
<212> TYPE: PRT
<213> ORGANISM: Artificial Sequence
<220> FEATURE:
<223> OTHER INFORMATION: linker

<400> SEQUENCE: 26

Gly Gly Asn Gly Ser Gly
1               5

<210> SEQ ID NO 27
<211> LENGTH: 472
<212> TYPE: PRT
<213> ORGANISM: Artificial Sequence
<220> FEATURE:
<223> OTHER INFORMATION: fusion protein scCD95L

<400> SEQUENCE: 27

Met Glu Thr Asp Thr Leu Leu Leu Trp Val Leu Leu Leu Trp Val Pro
1               5                   10                  15

Ala Gly Asn Gly Ser Glu Leu Arg Ser Val Ala His Leu Thr Gly Lys
            20                  25                  30

Ser Asn Ser Arg Ser Met Pro Leu Glu Trp Glu Asp Thr Tyr Gly Ile
        35                  40                  45

Val Leu Leu Ser Gly Val Lys Tyr Lys Lys Gly Gly Leu Val Ile Asn
    50                  55                  60

Glu Thr Gly Leu Tyr Phe Val Tyr Ser Lys Val Tyr Phe Arg Gly Gln
65                  70                  75                  80

Ser Cys Asn Asn Leu Pro Leu Ser His Lys Val Tyr Met Arg Asn Ser
                85                  90                  95

Lys Tyr Pro Gln Asp Leu Val Met Met Glu Gly Lys Met Met Ser Tyr
            100                 105                 110

Cys Thr Thr Gly Gln Met Trp Ala Arg Ser Ser Tyr Leu Gly Ala Val
        115                 120                 125

Phe Asn Leu Thr Ser Ala Asp His Leu Tyr Val Asn Val Ser Glu Leu
    130                 135                 140

Ser Leu Val Asn Phe Glu Glu Ser Gln Thr Phe Phe Gly Leu Tyr Lys
145                 150                 155                 160

Leu Gly Gly Ser Gly Ser Gly Ser Gly Arg Ser Val Ala His Leu Thr
                165                 170                 175

Gly Lys Ser Asn Ser Arg Ser Met Pro Leu Glu Trp Glu Asp Thr Tyr
            180                 185                 190

Gly Ile Val Leu Leu Ser Gly Val Lys Tyr Lys Lys Gly Gly Leu Val
        195                 200                 205

Ile Asn Glu Thr Gly Leu Tyr Phe Val Tyr Ser Lys Val Tyr Phe Arg
    210                 215                 220

Gly Gln Ser Cys Asn Asn Leu Pro Leu Ser His Lys Val Tyr Met Arg
225                 230                 235                 240

Asn Ser Lys Tyr Pro Gln Asp Leu Val Met Met Glu Gly Lys Met Met
                245                 250                 255

-continued

```
Ser Tyr Cys Thr Thr Gly Gln Met Trp Ala Arg Ser Ser Tyr Leu Gly
        260                 265                 270

Ala Val Phe Asn Leu Thr Ser Ala Asp His Leu Tyr Val Asn Val Ser
    275                 280                 285

Glu Leu Ser Leu Val Asn Phe Glu Glu Ser Gln Thr Phe Phe Gly Leu
290                 295                 300

Tyr Lys Leu Gly Gly Ser Gly Ser Gly Ser Gly Arg Ser Val Ala His
305                 310                 315                 320

Leu Thr Gly Lys Ser Asn Ser Arg Ser Met Pro Leu Glu Trp Glu Asp
                325                 330                 335

Thr Tyr Gly Ile Val Leu Leu Ser Gly Val Lys Tyr Lys Lys Gly Gly
            340                 345                 350

Leu Val Ile Asn Glu Thr Gly Leu Tyr Phe Val Tyr Ser Lys Val Tyr
                355                 360                 365

Phe Arg Gly Gln Ser Cys Asn Asn Leu Pro Leu Ser His Lys Val Tyr
    370                 375                 380

Met Arg Asn Ser Lys Tyr Pro Gln Asp Leu Val Met Met Glu Gly Lys
385                 390                 395                 400

Met Met Ser Tyr Cys Thr Thr Gly Gln Met Trp Ala Arg Ser Ser Tyr
                405                 410                 415

Leu Gly Ala Val Phe Asn Leu Thr Ser Ala Asp His Leu Tyr Val Asn
            420                 425                 430

Val Ser Glu Leu Ser Leu Val Asn Phe Glu Glu Ser Gln Thr Phe Phe
                435                 440                 445

Gly Leu Tyr Lys Leu Gly Gly Pro Gly Ser Ser Ser Ser Ser Ser Ala
    450                 455                 460

Trp Ser His Pro Gln Phe Glu Lys
465                 470

<210> SEQ ID NO 28
<211> LENGTH: 538
<212> TYPE: PRT
<213> ORGANISM: Artificial Sequence
<220> FEATURE:
<223> OTHER INFORMATION: fusion protein scTRAILwt
<220> FEATURE:
<221> NAME/KEY: MISC_FEATURE
<222> LOCATION: (186)..(186)
<223> OTHER INFORMATION: Xaa = Ser or Asn
<220> FEATURE:
<221> NAME/KEY: MISC_FEATURE
<222> LOCATION: (188)..(188)
<223> OTHER INFORMATION: Xaa = Ser or Asn
<220> FEATURE:
<221> NAME/KEY: MISC_FEATURE
<222> LOCATION: (355)..(355)
<223> OTHER INFORMATION: Xaa = Ser or Asn
<220> FEATURE:
<221> NAME/KEY: MISC_FEATURE
<222> LOCATION: (357)..(357)
<223> OTHER INFORMATION: Xaa = Ser or Asn

<400> SEQUENCE: 28

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60
```

```
Leu Ser Asn Leu His Leu Arg Asn Gly Glu Leu Val Ile His Glu Lys
 65                  70                  75                  80

Gly Phe Tyr Tyr Ile Tyr Ser Gln Thr Tyr Phe Arg Phe Gln Glu Glu
                 85                  90                  95

Ile Lys Glu Asn Thr Lys Asn Asp Lys Gln Met Val Gln Tyr Ile Tyr
                100                 105                 110

Lys Tyr Thr Ser Tyr Pro Asp Pro Ile Leu Leu Met Lys Ser Ala Arg
            115                 120                 125

Asn Ser Cys Trp Ser Lys Asp Ala Glu Tyr Gly Leu Tyr Ser Ile Tyr
            130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Gly Ser Gly Xaa Gly Xaa Gly Ser Arg Val
                180                 185                 190

Ala Ala His Ile Thr Gly Thr Arg Gly Arg Ser Asn Thr Leu Ser Ser
            195                 200                 205

Pro Asn Ser Lys Asn Glu Lys Ala Leu Gly Arg Lys Ile Asn Ser Trp
210                 215                 220

Glu Ser Ser Arg Ser Gly His Ser Phe Leu Ser Asn Leu His Leu Arg
225                 230                 235                 240

Asn Gly Glu Leu Val Ile His Glu Lys Gly Phe Tyr Tyr Ile Tyr Ser
                245                 250                 255

Gln Thr Tyr Phe Arg Phe Gln Glu Glu Ile Lys Glu Asn Thr Lys Asn
                260                 265                 270

Asp Lys Gln Met Val Gln Tyr Ile Tyr Lys Tyr Thr Ser Tyr Pro Asp
            275                 280                 285

Pro Ile Leu Leu Met Lys Ser Ala Arg Asn Ser Cys Trp Ser Lys Asp
290                 295                 300

Ala Glu Tyr Gly Leu Tyr Ser Ile Tyr Gln Gly Gly Ile Phe Glu Leu
305                 310                 315                 320

Lys Glu Asn Asp Arg Ile Phe Val Ser Val Thr Asn Glu His Leu Ile
                325                 330                 335

Asp Met Asp His Glu Ala Ser Phe Phe Gly Ala Phe Leu Val Gly Gly
                340                 345                 350

Ser Gly Xaa Gly Xaa Gly Ser Arg Val Ala Ala His Ile Thr Gly Thr
            355                 360                 365

Arg Gly Arg Ser Asn Thr Leu Ser Ser Pro Asn Ser Lys Asn Glu Lys
            370                 375                 380

Ala Leu Gly Arg Lys Ile Asn Ser Trp Glu Ser Ser Arg Ser Gly His
385                 390                 395                 400

Ser Phe Leu Ser Asn Leu His Leu Arg Asn Gly Glu Leu Val Ile His
                405                 410                 415

Glu Lys Gly Phe Tyr Tyr Ile Tyr Ser Gln Thr Tyr Phe Arg Phe Gln
                420                 425                 430

Glu Glu Ile Lys Glu Asn Thr Lys Asn Asp Lys Gln Met Val Gln Tyr
            435                 440                 445

Ile Tyr Lys Tyr Thr Ser Tyr Pro Asp Pro Ile Leu Leu Met Lys Ser
            450                 455                 460

Ala Arg Asn Ser Cys Trp Ser Lys Asp Ala Glu Tyr Gly Leu Tyr Ser
465                 470                 475                 480
```

```
Ile Tyr Gln Gly Gly Ile Phe Glu Leu Lys Glu Asn Asp Arg Ile Phe
                485                 490                 495

Val Ser Val Thr Asn Glu His Leu Ile Asp Met Asp His Glu Ala Ser
            500                 505                 510

Phe Phe Gly Ala Phe Leu Val Gly Gly Pro Gly Ser Ser Ser Ser Ser
        515                 520                 525

Ser Ala Trp Ser His Pro Gln Phe Glu Lys
    530                 535

<210> SEQ ID NO 29
<211> LENGTH: 546
<212> TYPE: PRT
<213> ORGANISM: Artificial Sequence
<220> FEATURE:
<223> OTHER INFORMATION: fusion protein scTRAILR2
<220> FEATURE:
<221> NAME/KEY: MISC_FEATURE
<222> LOCATION: (194)..(194)
<223> OTHER INFORMATION: Xaa = Ser or Asn
<220> FEATURE:
<221> NAME/KEY: MISC_FEATURE
<222> LOCATION: (196)..(196)
<223> OTHER INFORMATION: Xaa = Ser or Asn
<220> FEATURE:
<221> NAME/KEY: MISC_FEATURE
<222> LOCATION: (363)..(363)
<223> OTHER INFORMATION: Xaa = Ser or Asn
<220> FEATURE:
<221> NAME/KEY: MISC_FEATURE
<222> LOCATION: (365)..(365)
<223> OTHER INFORMATION: Xaa = Ser or Asn

<400> SEQUENCE: 29

Met Glu Thr Asp Thr Leu Leu Leu Trp Val Leu Leu Leu Trp Val Pro
1               5                   10                  15

Ala Gly Asn Gly Ser Pro Gly Ser Ser Ser Ser Ser Ser Arg Val Ala
            20                  25                  30

Ala His Ile Thr Gly Thr Arg Gly Arg Ser Asn Thr Leu Ser Ser Pro
        35                  40                  45

Asn Ser Lys Asn Glu Lys Ala Leu Gly Arg Lys Ile Asn Ser Trp Glu
50                  55                  60

Ser Ser Arg Ser Gly His Ser Phe Leu Ser Asn Leu His Leu Arg Asn
65                  70                  75                  80

Gly Glu Leu Val Ile His Glu Lys Gly Phe Tyr Tyr Ile Tyr Ser Gln
                85                  90                  95

Thr Gln Phe Lys Phe Arg Glu Glu Ile Lys Glu Asn Thr Lys Asn Asp
            100                 105                 110

Lys Gln Met Val Gln Tyr Ile Tyr Lys Tyr Thr Ser Tyr Pro Asp Pro
        115                 120                 125

Ile Leu Leu Met Lys Ser Ala Arg Asn Ser Cys Trp Ser Lys Asp Ala
130                 135                 140

Glu Tyr Gly Leu Tyr Ser Ile Tyr Gln Gly Gly Ile Phe Glu Leu Lys
145                 150                 155                 160

Glu Asn Asp Arg Ile Phe Val Ser Val Thr Asn Glu Arg Leu Leu Gln
                165                 170                 175

Met Asp His Glu Ala Ser Phe Phe Gly Ala Phe Leu Val Gly Gly Ser
            180                 185                 190

Gly Xaa Gly Xaa Gly Ser Arg Val Ala Ala His Ile Thr Gly Thr Arg
        195                 200                 205

Gly Arg Ser Asn Thr Leu Ser Ser Pro Asn Ser Lys Asn Glu Lys Ala
210                 215                 220
```

```
Leu Gly Arg Lys Ile Asn Ser Trp Glu Ser Ser Arg Ser Gly His Ser
225                 230                 235                 240

Phe Leu Ser Asn Leu His Leu Arg Asn Gly Glu Leu Val Ile His Glu
            245                 250                 255

Lys Gly Phe Tyr Tyr Ile Tyr Ser Gln Thr Gln Phe Lys Phe Arg Glu
        260                 265                 270

Glu Ile Lys Glu Asn Thr Lys Asn Asp Lys Gln Met Val Gln Tyr Ile
    275                 280                 285

Tyr Lys Tyr Thr Ser Tyr Pro Asp Pro Ile Leu Leu Met Lys Ser Ala
290                 295                 300

Arg Asn Ser Cys Trp Ser Lys Asp Ala Glu Tyr Gly Leu Tyr Ser Ile
305                 310                 315                 320

Tyr Gln Gly Gly Ile Phe Glu Leu Lys Glu Asn Asp Arg Ile Phe Val
                325                 330                 335

Ser Val Thr Asn Glu Arg Leu Leu Gln Met Asp His Glu Ala Ser Phe
            340                 345                 350

Phe Gly Ala Phe Leu Val Gly Gly Ser Gly Xaa Gly Xaa Gly Ser Arg
        355                 360                 365

Val Ala Ala His Ile Thr Gly Thr Arg Gly Arg Ser Asn Thr Leu Ser
370                 375                 380

Ser Pro Asn Ser Lys Asn Glu Lys Ala Leu Gly Arg Lys Ile Asn Ser
385                 390                 395                 400

Trp Glu Ser Ser Arg Ser Gly His Ser Phe Leu Ser Asn Leu His Leu
                405                 410                 415

Arg Asn Gly Glu Leu Val Ile His Glu Lys Gly Phe Tyr Tyr Ile Tyr
            420                 425                 430

Ser Gln Thr Gln Phe Lys Phe Arg Glu Glu Ile Lys Glu Asn Thr Lys
        435                 440                 445

Asn Asp Lys Gln Met Val Gln Tyr Ile Tyr Lys Tyr Thr Ser Tyr Pro
450                 455                 460

Asp Pro Ile Leu Leu Met Lys Ser Ala Arg Asn Ser Cys Trp Ser Lys
465                 470                 475                 480

Asp Ala Glu Tyr Gly Leu Tyr Ser Ile Tyr Gln Gly Gly Ile Phe Glu
                485                 490                 495

Leu Lys Glu Asn Asp Arg Ile Phe Val Ser Val Thr Asn Glu Arg Leu
            500                 505                 510

Leu Gln Met Asp His Glu Ala Ser Phe Phe Gly Ala Phe Leu Val Gly
        515                 520                 525

Gly Pro Gly Ser Ser Ser Ser Ser Ala Trp Ser His Pro Gln Phe
530                 535                 540

Glu Lys
545
```

<210> SEQ ID NO 30
<211> LENGTH: 1452
<212> TYPE: DNA
<213> ORGANISM: Artificial Sequence
<220> FEATURE:
<223> OTHER INFORMATION: nucleotide sequence: fusion protein scCD95L

<400> SEQUENCE: 30
aagcttgccg ccaccatgga gactgacacc ctgctgttgt gggtcctact gctttgggtc      60
cctgcaggaa atggatccga attgcgtagc gtcgcacatc tgacaggaa gtccaacagc      120 agaagtatgc ccctcgaatg ggaggatacc tatgggattg tgctcctttc aggcgtgaaa      180

```
tacaagaagg gtgggctcgt catcaatgaa actggattgt acttcgtcta ttcaaaggtt      240
tactttcgtg gtcaatcttg taataacttg cctctcagcc ataaggtcta tatgcgtaac      300
tccaaatacc cacaagacct cgttatgatg agggtaaga tgatgagtta ctgcaccaca       360
gggcaaatgt gggccaggag tagttacctt ggcgcggtgt ttaacctcac tagcgccgat      420
catttgtacg ttaatgtcag cgagctgtcc ttggtgaact tcgaggaaag ccaaacattc      480
tttggcttat acaaactcgg tggcagcggt agtggctccg aagaagcgt cgcacacttg       540 actggcaaat ctaattcccg ttcaatgcct ctggagtggg aagacactta tggcatcgtc      600
ttgctgtctg gtgtaaagta taagaagggt ggcctggtga ttaacgaaac cggcttgtac      660
ttcgtgtata gcaaagtcta cttcagagga cagagctgca caacttgcc tctgtcccat       720 aaagtgtata tgaggaatag taaatatcca caggatctag ttatgatgga agggaagatg      780
atgtcgtatt gtacgaccgg ccagatgtgg gctcgcagca gctatctggg tgccgtattc      840
aacttgactt ctgcggatca cctctatgtg aacgtgtccg aattgtcgct ggtgaatttt      900
gaggagtcac agaccttctt cggactctac aagctgggag gcagtggtag tggtagcggc      960
cgctctgttg ctcatctgac gggaaagagc aactctagga gtatgccgct ggagtgggag     1020
gacacatacg gtatcgtgct gttatccggc gttaagtaca agaaaggcgg attggtcatc     1080
aacgagactg gactctactt tgtctactcg aaggtgtact ttcgcggcca atcctgcaac     1140
aaccttccac tctctcacaa ggtctacatg aggaactcca gtacccaca ggacttggtg      1200 atgatggagg gcaagatgat gagctactgc actaccggac agatgtgggc acgatcctcg     1260
taccttggtg ccgtcttcaa cctgacatca gccgaccatc tgtacgtcaa cgtcagcgaa     1320
ctgtctctgg tcaacttcga ggaaagtcag acgttcttcg gtttgtataa gctcggcggt     1380
cctggctcga gtagcagcag ttcagcttgg agtcacccac agttcgagaa gtaataggcg     1440
cgccgctcta ga                                                         1452

<210> SEQ ID NO 31
<211> LENGTH: 1650
<212> TYPE: DNA
<213> ORGANISM: Artificial Sequence
<220> FEATURE:
<223> OTHER INFORMATION: nucleotide sequence: fusion protein scTRAILwt

<400> SEQUENCE: 31
aagcttgccg ccaccatgga gactgacacc ctgctgttgt gggtcctact gctttgggtc       60
cctgcaggaa atgacagag agtggctgct cacatcaccg gaactcgggg taggtctaac      120
accctgtcca gcccgaattc taagaacgag aaggctctgg caggaagat caactcttgg      180 gagtccagca gatccggtca tagttttcctg tctaacttgc acctgagaaa cggcgagctg      240
gtgatccatg agaagggctt ctactacatc tactctcaga cctacttccg ctttcaggag      300
gagatcaagg agaacaccaa gaacgacaag cagatggtgc agtacatcta caagtacacc      360
agctatccag acccaatcct gctgatgaag tccgctagga actcctgttg gagcaaagac      420
gccgagtatg gcctgtatag catctatcag ggaggcatct tcgagctgaa ggagaacgac      480
aggatcttcg tgagcgtcac taatgagcat ctcatcgaca tggaccatga agcctctttc      540
ttcggcgctt tcttagtggg cggttccgga arcggtartg gtagtcgcgt cgcggcacat      600
attactggca cccgagggag aagtaatact ttgtcaagtc ccaatagcaa gaatgagaag      660
gccctgggtc gaaagatcaa tagctgggag tcaagtcggt ctggacacag ctttctcagt      720
```

```
aatctccatc tccgaaatgg tgaattggtc atacatgaga aggggttcta ttacatctat    780
agccaaactt actttaggtt ccaagaggag attaaggaga acacgaagaa tgataagcag    840
atggttcaat atatttacaa gtacacttcc tatccagacc cgatcttgct tatgaagtca    900
gcccgtaata gctgttggag taaagatgca gaatacggac tctatagtat ttaccaaggt    960
gggatatttg aactcaagga gaatgatcgc atattcgtat ctgtgacaaa cgaacacttg   1020
attgatatgg accacgaagc tagtttcttc ggagcattcc tggtgggcgg aagcggcart   1080
ggaarcggct ctagagtagc cgcccacata accgggacaa ggggacgaag caacacgcta   1140
agttctccta actcaaagaa cgagaaagca cttggacgta agatcaactc ctgggaaagt   1200
tctcgtagtg ggcattcctt cctgtccaac ctccacttga gaaatgggga gcttgtgatt   1260
cacgaaaagg gattctacta catctactcc cagacatact tccgattcca agaggaaatc   1320
aaggagaata ctaagaacga caaacagatg gtccagtaca tatacaagta cacctcatac   1380
cccgatccta tactgttgat gaaatctgca aggaactctt gctggtctaa ggacgctgag   1440
tatgggttgt actcgatcta ccagggcgga attttcgagt tgaaagagaa cgaccgcata   1500
ttcgtgtcag taaccaacga gcacctgata gatatggacc atgaggcatc cttctttggt   1560
gccttcctgg tgggcggtcc tggctcgagt agcagcagtt cagcttggag tcacccacag   1620
ttcgagaagt aataggcgcg ccgcgctagc                                    1650

<210> SEQ ID NO 32
<211> LENGTH: 1674
<212> TYPE: DNA
<213> ORGANISM: Artificial Sequence
<220> FEATURE:
<223> OTHER INFORMATION: nucleotide sequence: fusion protein scTRAILR2

<400> SEQUENCE: 32
aagcttgccg ccaccatgga gactgacacc ctgctgttgt gggtcctact gctttgggtc     60
cctgcaggaa atggatcccc tggaagttct tcaagctcta gcagagtggc tgctcacatc    120
accggaactc ggggtaggtc taacaccctg tccagcccga attccaagaa cgagaaggct    180
ctgggcagga gatcaactc ttgggagtcc agcagatccg gtcatagttt cctgtctaac    240
ttgcacctga gaaacggcga gctggtgatc catgagaagg gcttctacta catctactct    300
cagacccagt tcaagtttcg ggaggagatc aaggagaaca ccaagaacga caagcagatg    360
gtgcagtaca tctacaagta caccagctat ccagacccaa tcctgctgat gaagtccgct    420
aggaactcct gttggagcaa agacgccgag tatggcctgt atagcatcta tcagggaggc    480
atcttcgagc tgaaggagaa cgacaggatc ttcgtgagcg tcactaatga gaggctgctc    540
cagatggacc atgaagcctc tttcttcggc gctttcttag tgggcggttc cggaarcggt    600
artggtagtc gcgtcgcggc acatattact ggcacccgag ggagaagtaa tactttgtca    660
agtcccaata gcaagaatga aaggccctg ggtcgaaaga tcaatagctg ggagtcaagt    720
cggtctggac acagctttct cagtaatctc catctccgaa atggtgaatt ggtcatacat    780
gagaaggggt tctattacat ctatagccaa actcagtta agttccgaga ggagattaag    840
gagaacacga gaatgataa gcagatggtt caatatattt acaagtacac ttcctatcca    900
gacccgatct tgcttatgaa gtcagcccgt aatagctgtt ggagtaaaga tgcagaatac    960
ggactctata gtatttacca aggtgggata tttgaactca aggagaatga tcgcatattc   1020
gtatctgtga caaacgaacg cttgcttcag atggaccacg aagctagttt cttcggagca   1080
ttcctggtgg gcggaagcgg cartggaarc ggctctagag tagccgccca cataaccggg   1140
```

```
acaaggggac gaagcaacac gctaagttct cctaactcaa agaacgagaa agcacttgga    1200
cgtaagatca actcctggga aagttctcgt agtgggcatt ccttcctgtc caacctccac    1260
ttgagaaatg gggagcttgt gattcacgaa aagggattct actacatcta ctcccagaca    1320
cagttcaaat tccgagagga aatcaaggag aatactaaga acgacaaaca gatggtccag    1380
tacatataca agtacacctc ataccccgat cctatactgt tgatgaaatc tgcaaggaac    1440
tcttgctggt ctaaggacgc tgagtatggg ttgtactcga tctaccaggg cggaattttc    1500
gagttgaaag agaacgaccg catattcgtg tcagtaacca acgagcgcct gttgcagatg    1560
gaccatgagg catccttctt tggtgccttc ctggtgggcg gtcctggctc gagtagcagc    1620
agttcagctt ggagtcaccc acagttcgag aagtaatagg cgcgccgcgc tagc          1674
```

<210> SEQ ID NO 33
<211> LENGTH: 222
<212> TYPE: PRT
<213> ORGANISM: Artificial Sequence
<220> FEATURE:
<223> OTHER INFORMATION: pertuzumab Fab-Heavy Chain modul (VHCH1)

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 34
<211> LENGTH: 214
<212> TYPE: PRT
<213> ORGANISM: Artificial Sequence
<220> FEATURE:
<223> OTHER INFORMATION: pertuzumab Fab-Light Chain modul (VLCL)

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 16
<212> TYPE: PRT
<213> ORGANISM: Artificial Sequence
<220> FEATURE:
<223> OTHER INFORMATION: human IGG1 hinge region

<400> SEQUENCE: 35

Lys Ser Cys Asp Lys Thr His Thr Cys Pro Pro Cys Pro Ala Pro Glu
1               5                   10                  15

<210> SEQ ID NO 36
<211> LENGTH: 263
<212> TYPE: PRT
<213> ORGANISM: Artificial Sequence
<220> FEATURE:
<223> OTHER INFORMATION: pertuzumab scFv-module

<400> SEQUENCE: 36

Met Glu Thr Asp Thr Leu Leu Leu Trp Val Leu Leu Trp Val Pro
1               5                   10                  15

Ala Gly Asn Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Thr Met Asp Trp Val Arg Gln Ala Pro Gly Lys Gly
    50                  55                  60

```
Leu Glu Trp Val Ala Asp Val Asn Pro Asn Ser Gly Gly Ser Ile Tyr
 65                  70                  75                  80

Asn Gln Arg Phe Lys Gly Arg Phe Thr Leu Ser Val Asp Arg Ser Lys
                 85                  90                  95

Asn Thr Leu Tyr Leu Gln Met Asn Ser Leu Arg Ala Glu Asp Thr Ala
            100                 105                 110

Val Tyr Tyr Cys Ala Arg Asn Leu Gly Pro Ser Phe Tyr Phe Asp Tyr
        115                 120                 125

Trp Gly Gln Gly Thr Leu Thr Val Ser Ser Gly Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asp Val Ser Ile Gly Val Ala Trp Tyr Gln Gln
            180                 185                 190

Lys Pro Gly Lys Ala Pro Lys Leu Leu Ile Tyr Ser Ala Ser Tyr Arg
        195                 200                 205

Tyr Thr Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Tyr Tyr Ile Tyr Pro Tyr Thr Phe Gly Gln Gly Thr
                245                 250                 255

Lys Val Glu Ile Lys Arg Thr
                260

<210> SEQ ID NO 37
<211> LENGTH: 230
<212> TYPE: PRT
<213> ORGANISM: Artificial Sequence
<220> FEATURE:
<223> OTHER INFORMATION: human IGG1 Fc part (hinge+CH2+CH3)

<400> SEQUENCE: 37

Lys Ser Cys Asp Lys Thr His Thr Cys Pro Pro Cys Pro Ala Pro Glu
1                   5                  10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
        50                  55                  60

Val Glu Val His Asn Ala Lys Thr Lys Pro Arg Glu Glu Gln Tyr Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160
```

```
Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Lys
        180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 38
<211> LENGTH: 246
<212> TYPE: PRT
<213> ORGANISM: Artificial Sequence
<220> FEATURE:
<223> OTHER INFORMATION: N-terminal Fc-module with signal peptide

<400> SEQUENCE: 38

Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 39
<211> LENGTH: 265
<212> TYPE: PRT
<213> ORGANISM: Artificial Sequence
<220> FEATURE:
```

<223> OTHER INFORMATION: pertuzumab Fab heavy chain module with signal
      peptide

<400> SEQUENCE: 39

Met Glu Thr Asp Thr Leu Leu Leu Trp Val Leu Leu Leu Trp Val Pro
1               5                   10                  15

Ala Gly Asn Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Thr Met Asp Trp Val Arg Gln Ala Pro Gly Lys Gly
    50                  55                  60

Leu Glu Trp Val Ala Asp Val Asn Pro Asn Ser Gly Gly Ser Ile Tyr
65                  70                  75                  80

Asn Gln Arg Phe Lys Gly Arg Phe Thr Leu Ser Val Asp Arg Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asn Leu Gly Pro Ser Phe Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Gly Ser Pro Gly Ser Ser Ser Ser Ser Ser
                245                 250                 255

Ala Trp Ser His Pro Gln Phe Glu Lys
            260                 265

<210> SEQ ID NO 40
<211> LENGTH: 253
<212> TYPE: PRT
<213> ORGANISM: Artificial Sequence
<220> FEATURE:
<223> OTHER INFORMATION: pertuzumab Fab light chain module with signal
      peptide

<400> SEQUENCE: 40

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Ile Gly Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110

Ile Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Ser Pro Gly Ser Ser
225                 230                 235                 240

Ser Ser Ser Ser Ala Trp Ser His Pro Gln Phe Glu Lys
                245                 250

<210> SEQ ID NO 41
<211> LENGTH: 823
<212> TYPE: DNA
<213> ORGANISM: Artificial Sequence
<220> FEATURE:
<223> OTHER INFORMATION: pertuzumab Fab heavy chain gene module

<400> SEQUENCE: 41
aagcttgccg ccaccatgga gactgacacc ctgctgttgt gggtcctact gctttgggtc     60
cctgcaggta acggtgaagt gcagctcgtc gaaagcggtg gcggactggt tcagcccggt    120
ggttctctgc ggctgtcttg tgctgcctcg ggtttcacgt tcactgacta cacaatggac    180
tgggtgcgtc aggctcctgg aaagggattg gagtgggtag ccgacgttaa tccaaactcc    240
ggcgggagca tctacaacca gaggttcaag gggaggttca ctctgagcgt ggatcgctcc    300
aagaacacgc tgtacctcca gatgaactct ctcagggccg aggacacggc tgtttactat    360
tgcgcgagga acctgggtcc ttccttctac ttcgactact ggggacaggg aaccctggtg    420
accgtcagct ccgcttctac caagggtcct agtgtgttcc ctcttgctcc agctctaaa    480 agcacctccg gtgaactgc tgctctgggc tgtctggtta aggactactt ccccgaaccc    540
gtgaccgtat cttggaactc cggcgcactt acttctggcg tccacacttt cccagccgtc    600
ttacagtcct ctggcctgta ttctttgagc agcgtcgtga ccgtgcctag cagtagtctg    660
ggcacccaga cctacatctg caacgtcaac cacaagccta gcaacaccaa ggttgacaag    720
aaggtcgagc taagtcgtg cgacaagacg cacggatccc ctggctcgag ttcaagctct    780
tctgcctggt cacatccaca attcgagaag taataggcgc gcc                     823

<210> SEQ ID NO 42
<211> LENGTH: 787
<212> TYPE: DNA
<213> ORGANISM: Artificial Sequence
<220> FEATURE:
<223> OTHER INFORMATION: pertuzumab Fab light chain gene module

<400> SEQUENCE: 42

```
aagcttgccg ccaccatgga gaccgataca ctgctcttgt gggtactctt gctgtgggtt      60
ccggatcta ccggtgacat ccagatgaca caatctccta gcagtctgag cgcaagtgtt     120
ggagatcgtg tcaccatcac atgcaaggcc agccaggatg tgagcattgg agtcgcctgg     180
tatcagcaga acccggcaa ggcacccaag ctgctgatct actcggccag ttacagatac     240
actggcgtac cttcgaggtt tagtggtagc ggttctggaa ccgatttcac cctcaccatt     300
agctccctcc aacccgagga cttcgccacc tactactgcc agcaatacta catctaccct     360
tacacgttcg gccaaggcac taaggtcgag attaaacgta cggtcgcagc tccttccgta     420
ttcatcttcc cacctagcga cgagcagcta aagtctggaa ctgcgtccgt cgtgtgcctg     480
ctcaacaact tctaccctcg ggaagcgaag gtccagtgga agtggacaa cgctctccag     540
tccggcaata gccaggaatc cgtgaccgag caggacagca aggattctac ctactcactg     600
tccagcaccc ttacgctgtc caaggccgac tacgagaagc ataaggtgta cgcttgtgag     660
gtgactcacc aaggtctgtc aagccctgtg accaagagct tcaacagagg cgagtgcgga     720
tccctggct cgagttcaag ctcttctgcc tggtcacatc cacaattcga aagtaatag      780
gcgcgcc                                                              787
```

<210> SEQ ID NO 43
<211> LENGTH: 771
<212> TYPE: PRT
<213> ORGANISM: Artificial Sequence
<220> FEATURE:
<223> OTHER INFORMATION: scTRAILwt-Fc fusion protein with signal peptide

<400> SEQUENCE: 43

```
Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
                20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
        50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Gly Ser Gly Ser Gly Asn Gly Ser Arg Val
            180                 185                 190
```

```
Ala Ala His Ile Thr Gly Thr Arg Gly Arg Ser Asn Thr Leu Ser Ser
        195                 200                 205

Pro Asn Ser Lys Asn Glu Lys Ala Leu Gly Arg Lys Ile Asn Ser Trp
210                 215                 220

Glu Ser Ser Arg Ser Gly His Ser Phe Leu Ser Asn Leu His Leu Arg
225                 230                 235                 240

Asn Gly Glu Leu Val Ile His Glu Lys Gly Phe Tyr Ile Tyr Ser
                245                 250                 255

Gln Thr Tyr Phe Arg Phe Gln Glu Glu Ile Lys Glu Asn Thr Lys Asn
                260                 265                 270

Asp Lys Gln Met Val Gln Tyr Ile Tyr Lys Tyr Thr Ser Tyr Pro Asp
            275                 280                 285

Pro Ile Leu Leu Met Lys Ser Ala Arg Asn Ser Cys Trp Ser Lys Asp
290                 295                 300

Ala Glu Tyr Gly Leu Tyr Ser Ile Tyr Gln Gly Gly Ile Phe Glu Leu
305                 310                 315                 320

Lys Glu Asn Asp Arg Ile Phe Val Ser Val Thr Asn Glu His Leu Ile
                325                 330                 335

Asp Met Asp His Glu Ala Ser Phe Phe Gly Ala Phe Leu Val Gly Gly
            340                 345                 350

Ser Gly Ser Gly Asn Gly Ser Arg Val Ala Ala His Ile Thr Gly Thr
        355                 360                 365

Arg Gly Arg Ser Asn Thr Leu Ser Ser Pro Asn Ser Lys Asn Glu Lys
370                 375                 380

Ala Leu Gly Arg Lys Ile Asn Ser Trp Glu Ser Ser Arg Ser Gly His
385                 390                 395                 400

Ser Phe Leu Ser Asn Leu His Leu Arg Asn Gly Glu Leu Val Ile His
                405                 410                 415

Glu Lys Gly Phe Tyr Tyr Ile Tyr Ser Gln Thr Tyr Phe Arg Phe Gln
            420                 425                 430

Glu Glu Ile Lys Glu Asn Thr Lys Asn Asp Lys Gln Met Val Gln Tyr
                435                 440                 445

Ile Tyr Lys Tyr Thr Ser Tyr Pro Asp Pro Ile Leu Leu Met Lys Ser
450                 455                 460

Ala Arg Asn Ser Cys Trp Ser Lys Asp Ala Glu Tyr Gly Leu Tyr Ser
465                 470                 475                 480

Ile Tyr Gln Gly Gly Ile Phe Glu Leu Lys Glu Asn Asp Arg Ile Phe
                485                 490                 495

Val Ser Val Thr Asn Glu His Leu Ile Asp Met Asp His Glu Ala Ser
            500                 505                 510

Phe Phe Gly Ala Phe Leu Val Gly Gly Pro Gly Ser Ser Ser Ser Ser
515                 520                 525

Ser Gly Ser Asp Lys Thr His Thr Cys Pro Pro Cys Pro Ala Pro Pro
530                 535                 540

Val Ala Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
```

```
                610             615                 620
Asn Gly Lys Glu Tyr Lys Cys Lys Val Ser Asn Lys Gly Leu Pro Ser
625                 630                 635                 640

Ser Ile Glu Lys Thr Ile Ser Lys Ala Lys Gly Gln Pro Arg Glu Pro
            645                 650                 655

Gln Val Tyr Thr Leu Pro Pro Ser Arg Glu Glu Met Thr Lys Asn Gln
            660                 665                 670

Val Ser Leu Thr Cys Leu Val Lys Gly Phe Tyr Pro Ser Asp Ile Ala
            675                 680                 685

Val Glu Trp Glu Ser Asn Gly Gln Pro Glu Asn Asn Tyr Lys Thr Thr
            690                 695                 700

Pro Pro Val Leu Asp Ser Asp Gly Ser Phe Phe Leu Tyr Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Ser Ser Ser Ser Ser Ala Trp Ser His Pro Gln
        755                 760                 765

Phe Glu Lys
    770

<210> SEQ ID NO 44
<211> LENGTH: 2341
<212> TYPE: DNA
<213> ORGANISM: Artificial Sequence
<220> FEATURE:
<223> OTHER INFORMATION: scTRAILwt-FC01 gene module

<400> SEQUENCE: 44
aagcttgccg ccaccatgga gactgacacc ctgctgttgt gggtcctact gctttgggtc      60
cctgcaggaa atggacagag agtggctgct cacatcaccg gaactcgggg taggtctaac     120
accctgtcca gcccgaattc taagaacgag aaggctctgg caggaagatc aactcttgg      180
gagtccagca gatccggtca tagttttcctg tctaacttgc acctgagaaa cggcgagctg    240
gtgatccatg agaagggctt ctactacatc tactctcaga cctacttccg cttt caggag    300
gagatcaagg agaacaccaa gaacgacaag cagatggtgc agtacatcta caagtacacc    360
agctatccag acccaatcct gctgatgaag tccgctagga actcctgttg gagcaaagac    420
gccgagtatg gcctgtatag catctatcag ggaggcatct tcgagctgaa ggagaacgac    480
aggatcttcg tgagcgtcac taatgagcat ctcatcgaca tggaccatga agcctctttc    540
ttcggcgctt tcttagtggg cggttccgga agcggtaatg gtagtcgcgt cgcggcacat    600
attactggca cccgagggag aagtaatact ttgtcaagtc caatagcaa gaatgagaag    660
gccctgggtc gaaagatcaa tagctggagt caagtcggt ctggacacag ctttctcagt    720
aatctccatc tccgaaatgg tgaattggtc atacatgaga aggggttcta ttacatctat    780
agccaaactt actttaggtt ccaagaggag attaaggaga cacgaagaa tgataagcag    840
atggttcaat atatttacaa gtacacttcc tatccagacc cgatcttgct tatgaagtca    900
gcccgtaata gctgttggag taaagatgca gaatacggac tctatagtat ttaccaaggt    960
gggatatttg aactcaagga gaatgatcgc atattcgtat ctgtgacaaa cgaacacttg   1020
attgatatgg accacgaagc tagttttctc ggagcattcc tggtgggcgg aagcggcagt   1080
ggaaacggct ctagagtagc cgcccacata accgggacaa ggggacgaag caacacgcta   1140
```

-continued

```
agttctccta actcaaagaa cgagaaagca cttggacgta agatcaactc ctgggaaagt    1200
tctcgtagtg ggcattcctt cctgtccaac ctccacttga gaatggggga gcttgtgatt    1260
cacgaaaagg gattctacta catctactcc cagacatact tccgattcca agaggaaatc    1320
aaggagaata ctaagaacga caaacagatg gtccagtaca tatacaagta cacctcatac    1380
cccgatccta tactgttgat gaaatctgca aggaactctt gctggtctaa ggacgctgag    1440
tatgggttgt actcgatcta ccagggcgga attttcgagt tgaaagagaa cgaccgcata    1500
ttcgtgtcag taaccaacga gcacctgata gatatggacc atgaggcatc cttctttggt    1560
gccttcctgg tgggcggtcc tggctcgagt agctcctcat ccggctccga taagacccac    1620
acctgccctc cctgtcctgc ccctcctgtc gctggaccta gcgtgttcct gttccctcca    1680
aagcctaagg acaccctgat gatctccagg acccctgagg tgacctgtgt ggtggtggac    1740
gtgtctcacg aagatcccga ggtgaagttc aactggtacg tggacggcgt ggaggtccac    1800
aacgccaaga ccaagcctag ggaggagcag tacaactcca cctaccgggt ggtgtctgtg    1860
ctgaccgtgc tgcaccagga ttggctgaac ggaaaggagt ataagtgtaa ggtctccaac    1920
aagggcctgc cttcatctat cgagaaaacc atctccaagg ccaagggcca gcctcgggag    1980
cctcaggtgt acaccctgcc tcctagcagg gaggagatga ccaagaacca ggtgtccctg    2040
acctgtctgg tgaagggctt ctacccttcc gatatcgccg tggagtggga gtctaatggc    2100
cagcccgaga caactacaa gaccacccct cctgtgctgg actctgacgg ctccttcttc    2160
ctgtactcca agctgaccgt ggacaagtcc agatggcagc agggcaacgt gttctcctgc    2220
tccgtgatgc acgaggccct gcacaatcac tacacccaga gtccctgtc tctgagtccg    2280 ggctcatctt caagctcttc tgcctggtct catccgcaat tcgagaaata ataggcgcgc    2340
c                                                                    2341
```

<210> SEQ ID NO 45
<211> LENGTH: 773
<212> TYPE: PRT
<213> ORGANISM: Artificial Sequence
<220> FEATURE:
<223> OTHER INFORMATION: HC-scTRAILwt-SNSN

<400> SEQUENCE: 45

```
Met Glu Thr Asp Thr Leu Leu Leu Trp Val Leu Leu Trp Val Pro
1               5                   10                  15

Ala Gly Asn Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Thr Met Asp Trp Val Arg Gln Ala Pro Gly Lys Gly
    50                  55                  60

Leu Glu Trp Val Ala Asp Val Asn Pro Asn Ser Gly Gly Ser Ile Tyr
65                  70                  75                  80

Asn Gln Arg Phe Lys Gly Arg Phe Thr Leu Ser Val Asp Arg Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asn Leu Gly Pro Ser Phe Tyr Phe Asp Tyr
        115                 120                 125

Trp Gly Gln Gly Thr Leu Val Thr Val Ser Ser Ala Ser Thr Lys Gly
    130                 135                 140
```

```
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
    195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Val Glu Pro Lys
225                 230                 235                 240

Ser Cys Asp Lys Thr His Gly Ser Pro Gly Ser Ser Ser Ser Ser Ser
                245                 250                 255

Arg Val Ala Ala His Ile Thr Gly Thr Arg Gly Arg Ser Asn Thr Leu
            260                 265                 270

Ser Ser Pro Asn Ser Lys Asn Glu Lys Ala Leu Gly Arg Lys Ile Asn
        275                 280                 285

Ser Trp Glu Ser Arg Ser Gly His Ser Phe Leu Ser Asn Leu His
290                 295                 300

Leu Arg Asn Gly Glu Leu Val Ile His Glu Lys Gly Phe Tyr Tyr Ile
305                 310                 315                 320

Tyr Ser Gln Thr Tyr Phe Arg Phe Gln Glu Glu Ile Lys Glu Asn Thr
                325                 330                 335

Lys Asn Asp Lys Gln Met Val Gln Tyr Ile Tyr Lys Tyr Thr Ser Tyr
            340                 345                 350

Pro Asp Pro Ile Leu Leu Met Lys Ser Ala Arg Asn Ser Cys Trp Ser
        355                 360                 365

Lys Asp Ala Glu Tyr Gly Leu Tyr Ser Ile Tyr Gln Gly Gly Ile Phe
    370                 375                 380

Glu Leu Lys Glu Asn Asp Arg Ile Phe Val Ser Val Thr Asn Glu His
385                 390                 395                 400

Leu Ile Asp Met Asp His Glu Ala Ser Phe Phe Gly Ala Phe Leu Val
                405                 410                 415

Gly Gly Ser Gly Ser Gly Asn Gly Ser Arg Val Ala Ala His Ile Thr
            420                 425                 430

Gly Thr Arg Gly Arg Ser Asn Thr Leu Ser Ser Pro Asn Ser Lys Asn
        435                 440                 445

Glu Lys Ala Leu Gly Arg Lys Ile Asn Ser Trp Glu Ser Ser Arg Ser
    450                 455                 460

Gly His Ser Phe Leu Ser Asn Leu His Leu Arg Asn Gly Glu Leu Val
465                 470                 475                 480

Ile His Glu Lys Gly Phe Tyr Tyr Ile Tyr Ser Gln Thr Tyr Phe Arg
                485                 490                 495

Phe Gln Glu Glu Ile Lys Glu Asn Thr Lys Asn Asp Lys Gln Met Val
            500                 505                 510

Gln Tyr Ile Tyr Lys Tyr Thr Ser Tyr Pro Asp Pro Ile Leu Leu Met
        515                 520                 525

Lys Ser Ala Arg Asn Ser Cys Trp Ser Lys Asp Ala Glu Tyr Gly Leu
    530                 535                 540

Tyr Ser Ile Tyr Gln Gly Gly Ile Phe Glu Leu Lys Glu Asn Asp Arg
545                 550                 555                 560
```

```
Ile Phe Val Ser Val Thr Asn Glu His Leu Ile Asp Met Asp His Glu
                565                 570                 575
Ala Ser Phe Phe Gly Ala Phe Leu Val Gly Gly Ser Gly Ser Gly Asn
            580                 585                 590
Gly Ser Arg Val Ala Ala His Ile Thr Gly Thr Arg Gly Arg Ser Asn
        595                 600                 605
Thr Leu Ser Ser Pro Asn Ser Lys Asn Glu Lys Ala Leu Gly Arg Lys
    610                 615                 620
Ile Asn Ser Trp Glu Ser Ser Arg Ser Gly His Ser Phe Leu Ser Asn
625                 630                 635                 640
Leu His Leu Arg Asn Gly Glu Leu Val Ile His Glu Lys Gly Phe Tyr
                645                 650                 655
Tyr Ile Tyr Ser Gln Thr Tyr Phe Arg Phe Gln Glu Glu Ile Lys Glu
            660                 665                 670
Asn Thr Lys Asn Asp Lys Gln Met Val Gln Tyr Ile Tyr Lys Tyr Thr
        675                 680                 685
Ser Tyr Pro Asp Pro Ile Leu Leu Met Lys Ser Ala Arg Asn Ser Cys
    690                 695                 700
Trp Ser Lys Asp Ala Glu Tyr Gly Leu Tyr Ser Ile Tyr Gln Gly Gly
705                 710                 715                 720
Ile Phe Glu Leu Lys Glu Asn Asp Arg Ile Phe Val Ser Val Thr Asn
                725                 730                 735
Glu His Leu Ile Asp Met Asp His Glu Ala Ser Phe Phe Gly Ala Phe
            740                 745                 750
Leu Val Gly Gly Pro Gly Ser Ser Ser Ser Ser Ala Trp Ser His
        755                 760                 765
Pro Gln Phe Glu Lys
    770

<210> SEQ ID NO 46
<211> LENGTH: 2347
<212> TYPE: DNA
<213> ORGANISM: Artificial Sequence
<220> FEATURE:
<223> OTHER INFORMATION: HC-scTRAILwt-SNSN gene module

<400> SEQUENCE: 46
aagcttgccg ccaccatgga gactgacacc ctgctgttgt gggtcctact gctttgggtc      60
cctgcaggta acggtgaagt gcagctcgtc gaaagcggtg gcggactggt tcagcccggt     120
ggttctctgc ggctgtcttg tgctgcctcg ggtttcacgt tcactgacta cacaatggac     180
tgggtgcgtc aggctcctgg aaagggattg gagtgggtag ccgacgttaa tccaaactcc     240
ggcgggagca tctacaacca gaggttcaag gggaggttca ctctgagcgt ggatcgctcc     300
aagaacacgc tgtacctcca gatgaactct ctcagggccg aggacacggc tgtttactat     360
tgcgcgagga acctgggtcc ttccttctac ttcgactact ggggacaggg aaccctggtg     420
accgtcagct ccgcttctac caagggtcct agtgtgttcc ctcttgctcc agctctaaa      480 agcacctccg gtgaactgc tgctctgggc tgtctggtta aggactactt ccccgaaccc     540
gtgaccgtat cttggaactc cggcgcactt acttctggcg tccacacttt ccagccgtc      600 ttacagtcct ctggcctgta ttctttgagc agcgtcgtga ccgtgcctag cagtagtctg      660
ggcacccaga cctacatctg caacgtcaac cacaagccta gcaacaccaa ggttgacaag      720
aaggtcgagc taagtcgtg cgacaagacg cacggatccc ctgaagttc ttcaagctct       780 agcagagtgg ctgctcacat caccggaact cggggtaggt ctaacaccct gtccagcccg    840
```

```
aattctaaga acgagaaggc tctgggcagg aagatcaact cttgggagtc cagcagatcc      900
ggtcatagtt tcctgtctaa cttgcacctg agaaacggcg agctggtgat ccatgagaag      960
ggcttctact acatctactc tcagacctac ttccgctttc aggaggagat caaggagaac     1020
accaagaacg acaagcagat ggtgcagtac atctacaagt acaccagcta tccagaccca     1080
atcctgctga tgaagtccgc taggaactcc tgttggagca agacgccga gtatggcctg     1140
tatagcatct atcagggagg catcttcgag ctgaaggaga cgacaggat cttcgtgagc     1200
gtcactaatg agcatctcat cgacatggac catgaagcct ctttcttcgg cgctttctta     1260
gtgggcggtt ccggaagcgg taatggtagt cgcgtcgcgg cacatattac tggcacccga     1320
gggagaagta atactttgtc aagtcccaat agcaagaatg agaaggccct gggtcgaaag     1380
atcaatagct gggagtcaag tcggtctgga cacagctttc tcagtaatct ccatctccga     1440
aatggtgaat tggtcataca tgagaagggg ttctattaca tctatagcca aacttacttt     1500
aggttccaag aggagattaa ggagaacacg aagaatgata gcagatggt tcaatatatt     1560
tacaagtaca cttcctatcc agacccgatc ttgcttatga agtcagcccg taatagctgt     1620
tggagtaaag atgcagaata cggactctat agtatttacc aaggtgggat atttgaactc     1680
aaggagaatg atcgcatatt cgtatctgtg acaaacgaac acttgattga tatggaccac     1740
gaagctagtt tcttcggagc attcctggtg gcggaagcg gcagtggaaa cggctctaga     1800
gtagccgccc acataaccgg acaagggga cgaagcaaca cgctaagttc tcctaactca     1860
aagaacgaga agcacttgg acgtaagatc aactcctggg aaagttctcg tagtgggcat     1920
tccttcctgt ccaacctcca cttgagaaat ggggagcttg tgattcacga aaagggattc     1980
tactacatct actcccagac atacttccga ttccaagagg aaatcaagga gaatactaag     2040
aacgacaaac agatggtcca gtacatatac aagtacacct catccccga tcctatactg     2100
ttgatgaaat ctgcaaggaa ctcttgctgg tctaaggacg ctgagtatgg gttgtactcg     2160
atctaccagg gcggaatttt cgagttgaaa gagaacgacc gcatattcgt gtcagtaacc     2220
aacgagcacc tgatagatat ggaccatgag gcatccttct tggtgccttc cctggtgggc     2280
ggtcctggct cgagtagcag cagttcagct tggagtcacc cacagttcga gaagtaatag     2340
gcgcgcc                                                              2347
```

<210> SEQ ID NO 47
<211> LENGTH: 773
<212> TYPE: PRT
<213> ORGANISM: Artificial Sequence
<220> FEATURE:
<223> OTHER INFORMATION: HC-scTRAILR2-SNSN with signal peptide

<400> SEQUENCE: 47

Met Glu Thr Asp Thr Leu Leu Leu Trp Val Leu Leu Leu Trp Val Pro
1               5                   10                  15

Ala Gly Asn Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Thr Asp Tyr Thr Met Asp Trp Val Arg Gln Ala Pro Gly Lys Gly
    50                  55                  60

Leu Glu Trp Val Ala Asp Val Asn Pro Asn Ser Gly Gly Ser Ile Tyr
65                  70                  75                  80

Asn Gln Arg Phe Lys Gly Arg Phe Thr Leu Ser Val Asp Arg Ser Lys

```
                     85                  90                  95
Asn Thr Leu Tyr Leu Gln Met Asn Ser Leu Arg Ala Glu Asp Thr Ala
                100                 105                 110

Val Tyr Tyr Cys Ala Arg Asn Leu Gly Pro Ser Phe Tyr Phe Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Gly Ser Pro Gly Ser Ser Ser Ser Ser Ser
                245                 250                 255

Arg Val Ala Ala His Ile Thr Gly Thr Arg Gly Arg Ser Asn Thr Leu
                260                 265                 270

Ser Ser Pro Asn Ser Lys Asn Glu Lys Ala Leu Gly Arg Lys Ile Asn
                275                 280                 285

Ser Trp Glu Ser Ser Arg Ser Gly His Ser Phe Leu Ser Asn Leu His
                290                 295                 300

Leu Arg Asn Gly Glu Leu Val Ile His Glu Lys Gly Phe Tyr Tyr Ile
305                 310                 315                 320

Tyr Ser Gln Thr Gln Phe Lys Phe Arg Glu Glu Ile Lys Glu Asn Thr
                325                 330                 335

Lys Asn Asp Lys Gln Met Val Gln Tyr Ile Tyr Lys Tyr Thr Ser Tyr
                340                 345                 350

Pro Asp Pro Ile Leu Leu Met Lys Ser Ala Arg Asn Ser Cys Trp Ser
                355                 360                 365

Lys Asp Ala Glu Tyr Gly Leu Tyr Ser Ile Tyr Gln Gly Gly Ile Phe
                370                 375                 380

Glu Leu Lys Glu Asn Asp Arg Ile Phe Val Ser Val Thr Asn Glu Arg
385                 390                 395                 400

Leu Leu Gln Met Asp His Glu Ala Ser Phe Phe Gly Ala Phe Leu Val
                405                 410                 415

Gly Gly Ser Gly Ser Gly Asn Gly Ser Arg Val Ala Ala His Ile Thr
                420                 425                 430

Gly Thr Arg Gly Arg Ser Asn Thr Leu Ser Ser Pro Asn Ser Lys Asn
                435                 440                 445

Glu Lys Ala Leu Gly Arg Lys Ile Asn Ser Trp Glu Ser Ser Arg Ser
                450                 455                 460

Gly His Ser Phe Leu Ser Asn Leu His Leu Arg Asn Gly Glu Leu Val
465                 470                 475                 480

Ile His Glu Lys Gly Phe Tyr Tyr Ile Tyr Ser Gln Thr Gln Phe Lys
                485                 490                 495

Phe Arg Glu Glu Ile Lys Glu Asn Thr Lys Asn Asp Lys Gln Met Val
                500                 505                 510
```

-continued

```
Gln Tyr Ile Tyr Lys Tyr Thr Ser Tyr Pro Asp Pro Ile Leu Leu Met
            515                 520                 525
Lys Ser Ala Arg Asn Ser Cys Trp Ser Lys Asp Ala Glu Tyr Gly Leu
            530                 535                 540
Tyr Ser Ile Tyr Gln Gly Gly Ile Phe Glu Leu Lys Glu Asn Asp Arg
545                 550                 555                 560
Ile Phe Val Ser Val Thr Asn Glu Arg Leu Leu Gln Met Asp His Glu
                565                 570                 575
Ala Ser Phe Phe Gly Ala Phe Leu Val Gly Ser Gly Ser Gly Asn
                580                 585                 590
Gly Ser Arg Val Ala Ala His Ile Thr Gly Thr Arg Gly Arg Ser Asn
            595                 600                 605
Thr Leu Ser Ser Pro Asn Ser Lys Asn Glu Lys Ala Leu Gly Arg Lys
            610                 615                 620
Ile Asn Ser Trp Glu Ser Ser Arg Ser Gly His Ser Phe Leu Ser Asn
625                 630                 635                 640
Leu His Leu Arg Asn Gly Glu Leu Val Ile His Glu Lys Gly Phe Tyr
                645                 650                 655
Tyr Ile Tyr Ser Gln Thr Gln Phe Lys Phe Arg Glu Glu Ile Lys Glu
                660                 665                 670
Asn Thr Lys Asn Asp Lys Gln Met Val Gln Tyr Ile Tyr Lys Tyr Thr
            675                 680                 685
Ser Tyr Pro Asp Pro Ile Leu Leu Met Lys Ser Ala Arg Asn Ser Cys
            690                 695                 700
Trp Ser Lys Asp Ala Glu Tyr Gly Leu Tyr Ser Ile Tyr Gln Gly Gly
705                 710                 715                 720
Ile Phe Glu Leu Lys Glu Asn Asp Arg Ile Phe Val Ser Val Thr Asn
                725                 730                 735
Glu Arg Leu Leu Gln Met Asp His Gly Ala Ser Phe Phe Gly Ala Phe
                740                 745                 750
Leu Val Gly Gly Pro Gly Ser Ser Ser Ser Ser Ala Trp Ser His
            755                 760                 765
Pro Gln Phe Glu Lys
        770

<210> SEQ ID NO 48
<211> LENGTH: 2347
<212> TYPE: DNA
<213> ORGANISM: Artificial Sequence
<220> FEATURE:
<223> OTHER INFORMATION: HC-scTRAILR2-SNSN gene module

<400> SEQUENCE: 48
aagcttgccg ccaccatgga gactgacacc ctgctgttgt gggtcctact gctttgggtc      60
cctgcaggta acggtgaagt gcagctcgtc gaaagcggtg gcggactggt tcagcccggt     120
ggttctctgc ggctgtcttg tgctgcctcg ggtttcacgt tcactgacta cacaatggac     180
tgggtgcgtc aggctcctgg aaagggattg gagtgggtag ccgacgttaa tccaaactcc     240
ggcgggagca tctacaacca gaggttcaag ggaggttca ctctgagcgt ggatcgctcc     300
aagaacacgc tgtacctcca gatgaactct ctcagggccg aggacacggc tgtttactat     360
tgcgcgagga actgggtcc ttccttctac ttcgactact ggggacaggg aaccctggtg     420
accgtcagct ccgcttctac caagggtcct agtgtgttcc ctcttgctcc cagctctaaa     480
agcacctccg gtggaactgc tgctctgggc tgtctggtta aggactactt ccccgaaccc     540
```

```
gtgaccgtat cttggaactc cggcgcactt acttctggcg tccacacttt cccagccgtc    600
ttacagtcct ctggcctgta ttctttgagc agcgtcgtga ccgtgcctag cagtagtctg    660
ggcacccaga cctacatctg caacgtcaac cacaagccta gcaacaccaa ggttgacaag    720
aaggtcgagc ctaagtcgtg cgacaagacg cacggatccc ctggaagttc ttcaagctct    780
agcagagtgg ctgctcacat caccggaact cggggtaggt ctaacaccct gtccagcccg    840
aattccaaga cgagaaggc tctgggcagg aagatcaact cttgggagtc cagcagatcc    900
ggtcatagtt tcctgtctaa cttgcacctg agaaacggcg agctggtgat ccatgagaag    960 gcttctact acatctactc tcagacccag ttcaagtttc gggaggagat caaggagaac   1020
accaagaacg acaagcagat ggtgcagtac atctacaagt acaccagcta ccagaccca   1080 atcctgctga tgaagtccgc taggaactcc tgttggagca agacgccga gtatggcctg   1140 tatagcatct atcagggagg catcttcgag ctgaaggaga cgacaggat cttcgtgagc   1200 gtcactaatg agaggctgct ccagatggac catgaagcct ctttcttcgg cgctttctta   1260
gtgggcggtt ccggaagcgg taatggtagt cgcgtcgcgg cacatattac tggcacccga   1320
gggagaagta atactttgtc aagtcccaat agcaagaatg agaaggccct gggtcgaaag   1380
atcaatagct gggagtcaag tcggtctgga cacagctttc tcagtaatct ccatctccga   1440
aatggtgaat tggtcataca tgagaagggg ttctattaca tctatagcca aactcagttt   1500
aagttccgag aggagattaa ggagaacacg aagaatgata agcagatggt tcaatatatt   1560
tacaagtaca cttcctatcc agacccgatc ttgcttatga agtcagcccg taatagctgt   1620
tggagtaaag atgcagaata cggactctat agtatttacc aaggtgggat atttgaactc   1680
aaggagaatg atcgcatatt cgtatctgtg acaaacgaac gcttgcttca gatggaccac   1740
gaagctagtt tcttcggagc attcctggtg ggcggaagcg gcagtggaaa cggctctaga   1800
gtagccgccc acataaccgg gacaagggga cgaagcaaca cgctaagttc tcctaactca   1860
aagaacgaga aagcacttgg acgtaagatc aactcctggg aaagttctcg tagtgggcat   1920
tccttcctgt ccaacctcca cttgagaaat ggggagcttg tgattcacga aaagggattc   1980
tactacatct actcccagac acagttcaaa ttccgagagg aaatcaagga gaatactaag   2040
aacgacaaac agatggtcca gtacatatac aagtacacct cataccccga tcctatactg   2100
ttgatgaaat ctgcaaggaa ctcttgctgg tctaaggacg ctgagtatgg gttgtactcg   2160
atctaccagg gcggaatttt cgagttgaaa gagaacgacc gcatattcgt gtcagtaacc   2220
aacgagcgcc tgttgcagat ggaccatgag gcatccttct ttggtgcctt cctggtgggc   2280
ggtcctggct cgagtagcag cagttcagct tggagtcacc cacagttcga gaagtaatag   2340
gcgcgcc                                                             2347
```

<210> SEQ ID NO 49
<211> LENGTH: 773
<212> TYPE: PRT
<213> ORGANISM: Artificial Sequence
<220> FEATURE:
<223> OTHER INFORMATION: HC-scTRAILR2-SSSS with signal peptide

<400> SEQUENCE: 49

```
Met Glu Thr Asp Thr Leu Leu Leu Trp Val Leu Leu Leu Trp Val Pro
 1               5                  10                  15

Ala Gly Asn Gly Glu Val Gln Leu Val Glu Ser Gly Gly Gly Leu Val
            20                  25                  30
```

```
Gln Pro Gly Gly Ser Leu Arg Leu Ser Cys Ala Ala Ser Gly Phe Thr
         35                  40                  45

Phe Thr Asp Tyr Thr Met Asp Trp Val Arg Gln Ala Pro Gly Lys Gly
 50                  55                  60

Leu Glu Trp Val Ala Asp Val Asn Pro Asn Ser Gly Gly Ser Ile Tyr
65                  70                  75                  80

Asn Gln Arg Phe Lys Gly Arg Phe Thr Leu Ser Val Asp Arg Ser Lys
                 85                  90                  95

Asn Thr Leu Tyr Leu Gln Met Asn Ser Leu Arg Ala Glu Asp Thr Ala
            100                 105                 110

Val Tyr Tyr Cys Ala Arg Asn Leu Gly Pro Ser Phe Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Gly Ser Pro Gly Ser Ser Ser Ser Ser Ser
                245                 250                 255

Arg Val Ala Ala His Ile Thr Gly Thr Arg Gly Arg Ser Asn Thr Leu
                260                 265                 270

Ser Ser Pro Asn Ser Lys Asn Glu Lys Ala Leu Gly Arg Lys Ile Asn
            275                 280                 285

Ser Trp Glu Ser Ser Arg Ser Gly His Ser Phe Leu Ser Asn Leu His
    290                 295                 300

Leu Arg Asn Gly Glu Leu Val Ile His Glu Lys Gly Phe Tyr Tyr Ile
305                 310                 315                 320

Tyr Ser Gln Thr Gln Phe Lys Phe Arg Glu Ile Lys Glu Asn Thr
                325                 330                 335

Lys Asn Asp Lys Gln Met Val Gln Tyr Ile Tyr Lys Tyr Thr Ser Tyr
            340                 345                 350

Pro Asp Pro Ile Leu Leu Met Lys Ser Ala Arg Asn Ser Cys Trp Ser
        355                 360                 365

Lys Asp Ala Glu Tyr Gly Leu Tyr Ser Ile Tyr Gln Gly Gly Ile Phe
    370                 375                 380

Glu Leu Lys Glu Asn Asp Arg Ile Phe Val Ser Val Thr Asn Glu Arg
385                 390                 395                 400

Leu Leu Gln Met Asp His Glu Ala Ser Phe Phe Gly Ala Phe Leu Val
                405                 410                 415

Gly Gly Ser Gly Ser Gly Ser Gly Ser Arg Val Ala Ala His Ile Thr
            420                 425                 430

Gly Thr Arg Gly Arg Ser Asn Thr Leu Ser Ser Pro Asn Ser Lys Asn
        435                 440                 445

Glu Lys Ala Leu Gly Arg Lys Ile Asn Ser Trp Glu Ser Ser Arg Ser
```

```
                450             455             460
Gly His Ser Phe Leu Ser Asn Leu His Leu Arg Asn Gly Glu Leu Val
465                     470                 475                 480

Ile His Glu Lys Gly Phe Tyr Tyr Ile Tyr Ser Gln Thr Gln Phe Lys
                    485                 490                 495

Phe Arg Glu Glu Ile Lys Glu Asn Thr Lys Asn Asp Lys Gln Met Val
                500                 505                 510

Gln Tyr Ile Tyr Lys Tyr Thr Ser Tyr Pro Asp Pro Ile Leu Leu Met
                515                 520                 525

Lys Ser Ala Arg Asn Ser Cys Trp Ser Lys Asp Ala Glu Tyr Gly Leu
            530                 535                 540

Tyr Ser Ile Tyr Gln Gly Gly Ile Phe Glu Leu Lys Glu Asn Asp Arg
545                 550                 555                 560

Ile Phe Val Ser Val Thr Asn Glu Arg Leu Leu Gln Met Asp His Glu
                565                 570                 575

Ala Ser Phe Phe Gly Ala Phe Leu Val Gly Gly Ser Gly Ser Gly Ser
                580                 585                 590

Gly Ser Arg Val Ala Ala His Ile Thr Gly Thr Arg Gly Arg Ser Asn
            595                 600                 605

Thr Leu Ser Ser Pro Asn Ser Lys Asn Glu Lys Ala Leu Gly Arg Lys
                610                 615                 620

Ile Asn Ser Trp Glu Ser Ser Arg Ser Gly His Ser Phe Leu Ser Asn
625                 630                 635                 640

Leu His Leu Arg Asn Gly Glu Leu Val Ile His Glu Lys Gly Phe Tyr
                    645                 650                 655

Tyr Ile Tyr Ser Gln Thr Gln Phe Lys Phe Arg Glu Glu Ile Lys Glu
                660                 665                 670

Asn Thr Lys Asn Asp Lys Gln Met Val Gln Tyr Ile Tyr Lys Tyr Thr
                675                 680                 685

Ser Tyr Pro Asp Pro Ile Leu Leu Met Lys Ser Ala Arg Asn Ser Cys
            690                 695                 700

Trp Ser Lys Asp Ala Glu Tyr Gly Leu Tyr Ser Ile Tyr Gln Gly Gly
705                 710                 715                 720

Ile Phe Glu Leu Lys Glu Asn Asp Arg Ile Phe Val Ser Val Thr Asn
                    725                 730                 735

Glu Arg Leu Leu Gln Met Asp His Glu Ala Ser Phe Phe Gly Ala Phe
                740                 745                 750

Leu Val Gly Gly Pro Gly Ser Ser Ser Ser Ser Ala Trp Ser His
            755                 760                 765

Pro Gln Phe Glu Lys
770

<210> SEQ ID NO 50
<211> LENGTH: 2347
<212> TYPE: DNA
<213> ORGANISM: Artificial Sequence
<220> FEATURE:
<223> OTHER INFORMATION: HC-scTRAILR2-SSSS gene module

<400> SEQUENCE: 50
aagcttgccg ccaccatgga gactgacacc ctgctgttgt gggtcctact gctttgggtc        60
cctgcaggta acggtgaagt gcagctcgtc gaaagcggtg gcggactggt tcagcccggt       120
ggttctctgc ggctgtcttg tgctgcctcg ggtttcacgt tcactgacta cacaatggac       180
tgggtgcgtc aggctcctgg aaagggattg gagtgggtag ccgacgttaa tccaaactcc       240
```

```
ggcgggagca tctacaacca gaggttcaag gggaggttca ctctgagcgt ggatcgctcc    300
aagaacacgc tgtacctcca gatgaactct ctcagggccg aggacacggc tgtttactat    360
tgcgcgagga acctgggtcc ttccttctac ttcgactact ggggacaggg aaccctggtg    420
accgtcagct ccgcttctac caagggtcct agtgtgttcc ctcttgctcc agctctaaa    480 agcacctccg gtggaactgc tgctctgggc tgtctggtta aggactactt ccccgaaccc    540
gtgaccgtat cttggaactc cggcgcactt acttctggcg tccacacttt cccagccgtc    600
ttacagtcct ctggcctgta ttctttgagc agcgtcgtga ccgtgcctag cagtagtctg    660
ggcacccaga cctacatctg caacgtcaac cacaagccta gcaacaccaa ggttgacaag    720
aaggtcgagc ctaagtcgtg cgacaagacg cacggatccc ctggaagttc ttcaagctct    780
agcagagtgg ctgctcacat caccggaact cggggtaggt ctaacaccct gtccagcccg    840
aattccaaga acgagaaggc tctgggcagg aagatcaact cttgggagtc cagcagatcc    900
ggtcatagtt tcctgtctaa cttgcacctg agaaacggcg agctggtgat ccatgagaag    960
ggcttctact acatctactc tcagacccag ttcaagtttc gggaggagat caaggagaac   1020
accaagaacg acaagcagat ggtgcagtac atctacaagt acaccagcta tccagaccca   1080
atcctgctga tgaagtccgc taggaactcc tgttggagca agacgccga gtatggcctg   1140 tatagcatct atcagggagg catcttcgag ctgaaggaga acgacaggat cttcgtgagc   1200
gtcactaatg agaggctgct ccagatggac catgaagcct ctttcttcgg cgctttctta   1260
gtgggcggtt ccggaagcgg tagtggtagt cgcgtcgcgg cacatattac tggcacccga   1320
gggagaagta atactttgtc aagtcccaat agcaagaatg agaaggccct gggtcgaaag   1380
atcaatagct gggagtcaag tcggtctgga cacagctttc tcagtaatct ccatctccga   1440
aatggtgaat tggtcataca tgagaagggg ttctattaca tctatagcca aactcagttt   1500
aagttccgag aggagattaa ggagaacacg aagaatgata agcagatggt tcaatatatt   1560
tacaagtaca cttcctatcc agacccgatc ttgcttatga agtcagcccg taatagctgt   1620
tggagtaaag atgcagaata cggactctat agtatttacc aaggtgggat atttgaactc   1680
aaggagaatg atcgcatatt cgtatctgtg acaaacgaac gcttgcttca gatggaccac   1740
gaagctagtt tcttcggagc attcctggtg gcggaagcg gcagtggaag cggctctaga   1800
gtagccgccc acataaccgg gacaagggga cgaagcaaca cgctaagttc tcctaactca   1860
aagaacgaga agcacttgg acgtaagatc aactcctggg aaagttctcg tagtgggcat   1920
tccttcctgt ccaacctcca cttgagaaat ggggagcttg tgattcacga aaagggattc   1980
tactacatct actcccagac acagttcaaa ttccgagagg aaatcaagga gaatactaag   2040
aacgacaaac agatggtcca gtacatatac aagtacacct catccccga tcctatactg   2100 ttgatgaaat ctgcaaggaa ctcttgctgg tctaaggacg ctgagtatgg gttgtactcg   2160
atctaccagg gcggaatttt cgagttgaaa gagaacgacc gcatattcgt gtcagtaacc   2220
aacgagcgcc tgttgcagat ggaccatgag gcatccttct ttggtgcctt cctggtgggc   2280
ggtcctggct cgagtagcag cagttcagct tggagtcacc cacagttcga gaagtaatag   2340
gcgcgcc                                                              2347
```

<210> SEQ ID NO 51
<211> LENGTH: 761
<212> TYPE: PRT
<213> ORGANISM: Artificial Sequence
<220> FEATURE:

<223> OTHER INFORMATION: LC-scTRAILR2-SNSN

<400> SEQUENCE: 51

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Ile Gly Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Tyr
            100                 105                 110

Ile Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Ser Pro Gly Ser Ser
225                 230                 235                 240

Ser Ser Ser Ser Arg Val Ala Ala His Ile Thr Gly Thr Arg Gly Arg
                245                 250                 255

Ser Asn Thr Leu Ser Ser Pro Asn Ser Lys Asn Glu Lys Ala Leu Gly
            260                 265                 270

Arg Lys Ile Asn Ser Trp Glu Ser Ser Arg Ser Gly His Ser Phe Leu
        275                 280                 285

Ser Asn Leu His Leu Arg Asn Gly Glu Leu Val Ile His Glu Lys Gly
    290                 295                 300

Phe Tyr Tyr Ile Tyr Ser Gln Thr Gln Phe Lys Phe Arg Glu Glu Ile
305                 310                 315                 320

Lys Glu Asn Thr Lys Asn Asp Lys Gln Met Val Gln Tyr Ile Tyr Lys
                325                 330                 335

Tyr Thr Ser Tyr Pro Asp Pro Ile Leu Leu Met Lys Ser Ala Arg Asn
            340                 345                 350

Ser Cys Trp Ser Lys Asp Ala Glu Tyr Gly Leu Tyr Ser Ile Tyr Gln
        355                 360                 365

Gly Gly Ile Phe Glu Leu Lys Glu Asn Asp Arg Ile Phe Val Ser Val
    370                 375                 380

Thr Asn Glu Arg Leu Leu Gln Met Asp His Glu Ala Ser Phe Phe Gly
385                 390                 395                 400
```

Ala Phe Leu Val Gly Gly Ser Gly Asn Gly Ser Arg Val Ala
                405                 410                 415

Ala His Ile Thr Gly Thr Arg Gly Arg Ser Asn Thr Leu Ser Ser Pro
            420                 425                 430

Asn Ser Lys Asn Glu Lys Ala Leu Gly Arg Lys Ile Asn Ser Trp Glu
        435                 440                 445

Ser Ser Arg Ser Gly His Ser Phe Leu Ser Asn Leu His Leu Arg Asn
    450                 455                 460

Gly Glu Leu Val Ile His Glu Lys Gly Phe Tyr Tyr Ile Tyr Ser Gln
465                 470                 475                 480

Thr Gln Phe Lys Phe Arg Glu Glu Ile Lys Glu Asn Thr Lys Asn Asp
                485                 490                 495

Lys Gln Met Val Gln Tyr Ile Tyr Lys Tyr Thr Ser Tyr Pro Asp Pro
            500                 505                 510

Ile Leu Leu Met Lys Ser Ala Arg Asn Ser Cys Trp Ser Lys Asp Ala
        515                 520                 525

Glu Tyr Gly Leu Tyr Ser Ile Tyr Gln Gly Gly Ile Phe Glu Leu Lys
    530                 535                 540

Glu Asn Asp Arg Ile Phe Val Ser Val Thr Asn Glu Arg Leu Leu Gln
545                 550                 555                 560

Met Asp His Glu Ala Ser Phe Phe Gly Ala Phe Leu Val Gly Gly Ser
                565                 570                 575

Gly Ser Gly Asn Gly Ser Arg Val Ala Ala His Ile Thr Gly Thr Arg
            580                 585                 590

Gly Arg Ser Asn Thr Leu Ser Ser Pro Asn Ser Lys Asn Glu Lys Ala
        595                 600                 605

Leu Gly Arg Lys Ile Asn Ser Trp Glu Ser Ser Arg Ser Gly His Ser
    610                 615                 620

Phe Leu Ser Asn Leu His Leu Arg Asn Gly Glu Leu Val Ile His Glu
625                 630                 635                 640

Lys Gly Phe Tyr Tyr Ile Tyr Ser Gln Thr Gln Phe Lys Phe Arg Glu
                645                 650                 655

Glu Ile Lys Glu Asn Thr Lys Asn Asp Lys Gln Met Val Gln Tyr Ile
            660                 665                 670

Tyr Lys Tyr Thr Ser Tyr Pro Asp Pro Ile Leu Leu Met Lys Ser Ala
        675                 680                 685

Arg Asn Ser Cys Trp Ser Lys Asp Ala Glu Tyr Gly Leu Tyr Ser Ile
    690                 695                 700

Tyr Gln Gly Gly Ile Phe Glu Leu Lys Glu Asn Asp Arg Ile Phe Val
705                 710                 715                 720

Ser Val Thr Asn Glu Arg Leu Leu Gln Met Asp His Glu Ala Ser Phe
                725                 730                 735

Phe Gly Ala Phe Leu Val Gly Gly Pro Gly Ser Ser Ser Ser Ser Ser
            740                 745                 750

Ala Trp Ser His Pro Gln Phe Glu Lys
        755                 760

<210> SEQ ID NO 52
<211> LENGTH: 8
<212> TYPE: PRT
<213> ORGANISM: Artificial Sequence
<220> FEATURE:
<223> OTHER INFORMATION: linker sequence

<400> SEQUENCE: 52

```
Gly Ser Gly Ser Gly Ser Gly Ser
1               5

<210> SEQ ID NO 53
<211> LENGTH: 8
<212> TYPE: PRT
<213> ORGANISM: Artificial Sequence
<220> FEATURE:
<223> OTHER INFORMATION: linker sequence

<400> SEQUENCE: 53

Gly Ser Gly Ser Gly Asn Gly Ser
1               5

<210> SEQ ID NO 54
<211> LENGTH: 8
<212> TYPE: PRT
<213> ORGANISM: Artificial Sequence
<220> FEATURE:
<223> OTHER INFORMATION: linker sequence figure 21A
<220> FEATURE:
<221> NAME/KEY: MISC_FEATURE
<222> LOCATION: (0)..(0)
<223> OTHER INFORMATION: linker sequence figure 21A

<400> SEQUENCE: 54

Gly Ser Gly Asn Gly Ser Gly Ser
1               5

<210> SEQ ID NO 55
<211> LENGTH: 12
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<223> OTHER INFORMATION: Linker1 [DKTHTG(S)a(G)b; (a=0-5; b=0 or 1)],
      example1, when a=5 and b=1

<400> SEQUENCE: 55

Asp Lys Thr His Thr Gly Ser Ser Ser Ser Ser Gly
1               5                   10

<210> SEQ ID NO 56
<211> LENGTH: 11
<212> TYPE: PRT
<213> ORGANISM: Artificial Sequence
<220> FEATURE:
<223> OTHER INFORMATION: page 28, Linker1, [DKTHTG(S)a(G)b; (a=0-5; b=0
      or 1)]
<220> FEATURE:
<221> NAME/KEY: MISC_FEATURE
<223> OTHER INFORMATION: Linker1 [DKTHTG(S)a(G)b; (a=0-5; b=0 or 1)];
      example2, when a=5 and b=0

<400> SEQUENCE: 56

Asp Lys Thr His Thr Gly Ser Ser Ser Ser Ser
1               5                   10

<210> SEQ ID NO 57
<211> LENGTH: 15
<212> TYPE: PRT
<213> ORGANISM: Artificial Sequence
<220> FEATURE:
<223> OTHER INFORMATION: page 28, Linker2, [DKTHTGS(S)a(GS)bG(S)c;
      (a,b=0, 1-6; c=0 or 1)]
<220> FEATURE:
<221> NAME/KEY: MISC_FEATURE
<223> OTHER INFORMATION: Linker2 [DKTHTGS(S)a(GS)bG(S)c; (a,b=0, 1-6;
``` c=0 or 1)], example-1, when a=6 and b=0 and c=1

<400> SEQUENCE: 57

Asp Lys Thr His Thr Gly Ser Ser Ser Ser Ser Ser Ser Gly Ser
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: page 28, Linker2, [DKTHTGS(S)a(GS)bG(S)c;
      (a,b=0, 1-6; c=0 or 1)]
<220> FEATURE:
<221> NAME/KEY: MISC_FEATURE
<223> OTHER INFORMATION: Linker2 [DKTHTGS(S)a(GS)bG(S)c; (a,b=0, 1-6;
      c=0 or 1)], example2, when a=6 and b=1 and c=1

<400> SEQUENCE: 58

Asp Lys Thr His Thr Gly Ser Ser Ser Ser Ser Ser Ser Gly Ser Gly
1               5                   10                  15

Ser

<210> SEQ ID NO 59
<211> LENGTH: 14
<212> TYPE: PRT
<213> ORGANISM: Artificial Sequence
<220> FEATURE:
<223> OTHER INFORMATION: page 28, Linker2, [DKTHTGS(S)a(GS)bG(S)c;
      (a,b=0, 1-6; c=0 or 1)]
<220> FEATURE:
<221> NAME/KEY: MISC_FEATURE
<223> OTHER INFORMATION: Linker2 [DKTHTGS(S)a(GS)bG(S)c; (a,b=0, 1-6;
      c=0 or 1)], example3, when a=5 and b=0 and c=1

<400> SEQUENCE: 59

Asp Lys Thr His Thr Gly Ser Ser Ser Ser Ser Ser Gly Ser
1               5                   10

<210> SEQ ID NO 60
<211> LENGTH: 16
<212> TYPE: PRT
<213> ORGANISM: Artificial Sequence
<220> FEATURE:
<223> OTHER INFORMATION: page 28, Linker2, [DKTHTGS(S)a(GS)bG(S)c;
      (a,b=0, 1-6; c=0 or 1)]
<220> FEATURE:
<221> NAME/KEY: MISC_FEATURE
<223> OTHER INFORMATION: Linker2 [DKTHTGS(S)a(GS)bG(S)c; (a,b=0, 1-6;
      c=0 or 1)], example4, when a=5 and b=1 and c=1

<400> SEQUENCE: 60

Asp Lys Thr His Thr Gly Ser Ser Ser Ser Ser Ser Gly Ser Gly Ser
1               5                   10                  15

<210> SEQ ID NO 61
<211> LENGTH: 12
<212> TYPE: PRT
<213> ORGANISM: Artificial Sequence
<220> FEATURE:
<223> OTHER INFORMATION: page 28, Linker2, [DKTHTGS(S)a(GS)bG(S)c;
      (a,b=0, 1-6; c=0 or 1)]
<220> FEATURE:
<221> NAME/KEY: MISC_FEATURE
<223> OTHER INFORMATION: Linker2 [DKTHTGS(S)a(GS)bG(S)c; (a,b=0, 1-6;
      c=0 or 1)], example5, when a=3 and b=0 and c=1

<400> SEQUENCE: 61

Asp Lys Thr His Thr Gly Ser Ser Ser Ser Gly Ser

```
1               5                    10
```

<210> SEQ ID NO 62
<211> LENGTH: 10
<212> TYPE: PRT
<213> ORGANISM: Artificial Sequence
<220> FEATURE:
<223> OTHER INFORMATION: page 28, Linker3, [DKTG(S)a(G)b; (a=0-5;
      b=0 or1)]
<220> FEATURE:
<221> NAME/KEY: MISC_FEATURE
<223> OTHER INFORMATION: Linker3 [DKTG(S)a(G)b; (a=0-5; b=0 or1)],
      example1, when a=5 and b=1

<400> SEQUENCE: 62

```
Asp Lys Thr Gly Ser Ser Ser Ser Ser Gly
1               5                    10
```

<210> SEQ ID NO 63
<211> LENGTH: 13
<212> TYPE: PRT
<213> ORGANISM: Artificial Sequence
<220> FEATURE:
<223> OTHER INFORMATION: page 28, Linker4, [DKTG(S)a(GS)bG(S)c;
      (a,b =0, 1-6; c=0 or 1)]
<220> FEATURE:
<221> NAME/KEY: MISC_FEATURE
<223> OTHER INFORMATION: Linker4 [DKTG(S)a(GS)bG(S)c; (a,b =0, 1-6; c=0
      or 1)], example1, when a=6 and b=0 and c=1

<400> SEQUENCE: 63

```
Asp Lys Thr Gly Ser Ser Ser Ser Ser Ser Ser Gly Ser
1               5                    10
```

<210> SEQ ID NO 64
<211> LENGTH: 15
<212> TYPE: PRT
<213> ORGANISM: Artificial Sequence
<220> FEATURE:
<223> OTHER INFORMATION: page 28, Linker4, [DKTG(S)a(GS)bG(S)c; (a,b =0,
      1-6; c=0 or 1)]
<220> FEATURE:
<221> NAME/KEY: MISC_FEATURE
<223> OTHER INFORMATION: Linker4 [DKTG(S)a(GS)bG(S)c; (a,b =0, 1-6; c=0
      or 1)], example2, when a=6 and b=1 and c=1

<400> SEQUENCE: 64

```
Asp Lys Thr Gly Ser Ser Ser Ser Ser Ser Ser Gly Ser Gly Ser
1               5                    10                   15
```

<210> SEQ ID NO 65
<211> LENGTH: 14
<212> TYPE: PRT
<213> ORGANISM: Artificial Sequence
<220> FEATURE:
<223> OTHER INFORMATION: page 28, Linker4, [DKTG(S)a(GS)bG(S)c; (a,b =0,
      1-6; c=0 or 1)]
<220> FEATURE:
<221> NAME/KEY: MISC_FEATURE
<223> OTHER INFORMATION: Linker4 [DKTG(S)a(GS)bG(S)c; (a,b =0, 1-6; c=0
      or 1)], example3, when a=5 and b=1 and c=1

<400> SEQUENCE: 65

```
Asp Lys Thr Gly Ser Ser Ser Ser Ser Ser Gly Ser Gly Ser
1               5                    10
```

<210> SEQ ID NO 66
<211> LENGTH: 12
<212> TYPE: PRT
<213> ORGANISM: Artificial Sequence

```
<220> FEATURE:
<223> OTHER INFORMATION: page 28, Linker4, [DKTG(S)a(GS)bG(S)c; (a,b =0,
     1-6; c=0 or 1)]
<220> FEATURE:
<221> NAME/KEY: MISC_FEATURE
<223> OTHER INFORMATION: Linker4 [DKTG(S)a(GS)bG(S)c; (a,b =0, 1-6; c=0
     or 1)], example4, when a=5 and b=0 and c=1

<400> SEQUENCE: 66

Asp Lys Thr Gly Ser Ser Ser Ser Ser Ser Gly Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: page 28, Linker4, [DKTG(S)a(GS)bG(S)c; (a,b =0,
     1-6; c=0 or 1)]
<220> FEATURE:
<221> NAME/KEY: MISC_FEATURE
<223> OTHER INFORMATION: Linker4 [DKTG(S)a(GS)bG(S)c; (a,b =0, 1-6; c=0
     or 1)], example5, when a=3 and b=0 and c=1

<400> SEQUENCE: 67

Asp Lys Thr Gly Ser Ser Ser Ser Gly Ser
1               5                   10

<210> SEQ ID NO 68
<211> LENGTH: 8
<212> TYPE: PRT
<213> ORGANISM: Artificial Sequence
<220> FEATURE:
<223> OTHER INFORMATION: page 28, Linker5, [SSG(S)a(GS)bG(S)c; (a, b =0,
     1-6; c=0 or 1)]
<220> FEATURE:
<221> NAME/KEY: MISC_FEATURE
<223> OTHER INFORMATION: Linker5 [SSG(S)a(GS)bG(S)c; (a, b =0, 1-6; c=0
     or 1)], example1, when a=1 and b=1and c=1

<400> SEQUENCE: 68

Ser Ser Gly Ser Gly Ser Gly Ser
1               5

<210> SEQ ID NO 69
<211> LENGTH: 12
<212> TYPE: PRT
<213> ORGANISM: Artificial Sequence
<220> FEATURE:
<223> OTHER INFORMATION: page 28, Linker5, [SSG(S)a(GS)bG(S)c; (a, b =0,
     1-6; c=0 or 1)]
<220> FEATURE:
<221> NAME/KEY: MISC_FEATURE
<223> OTHER INFORMATION: Linker5 [SSG(S)a(GS)bG(S)c; (a, b =0, 1-6; c=0
     or 1)], example2, when a=5 and b=1and c=1

<400> SEQUENCE: 69

Ser Ser Gly Ser Ser Ser Ser Ser Gly Ser Gly Ser
1               5                   10

<210> SEQ ID NO 70
<211> LENGTH: 8
<212> TYPE: PRT
<213> ORGANISM: Artificial Sequence
<220> FEATURE:
<223> OTHER INFORMATION: page 28, Linker6, [SS(GGGS)aG(s)b, (a=0, 1-4,
     b=0 or 1)]
<220> FEATURE:
<221> NAME/KEY: MISC_FEATURE
<223> OTHER INFORMATION: Linker6 [SS(GGGS)aG(s)b, (a=0, 1-4, b=0 or 1)],
     example1, when a=1 and b=1
```

```
<400> SEQUENCE: 70

Ser Ser Gly Gly Gly Ser Gly Ser
1               5

<210> SEQ ID NO 71
<211> LENGTH: 12
<212> TYPE: PRT
<213> ORGANISM: Artificial Sequence
<220> FEATURE:
<223> OTHER INFORMATION: page 28, Linker6, [SS(GGGS)aG(s)b, (a=0, 1-4,
      b=0 or 1)]
<220> FEATURE:
<221> NAME/KEY: MISC_FEATURE
<223> OTHER INFORMATION: Linker6 [SS(GGGS)aG(s)b, (a=0, 1-4, b=0 or 1)],
      example2, when a=2 and b=1

<400> SEQUENCE: 71

Ser Ser Gly Gly Gly Ser Gly Gly Gly Ser Gly Ser
1               5                   10

<210> SEQ ID NO 72
<211> LENGTH: 11
<212> TYPE: PRT
<213> ORGANISM: Artificial Sequence
<220> FEATURE:
<223> OTHER INFORMATION: page 28, Linker7, [GSPGSSSSSS(G)a, (a=0 or 1)]
<220> FEATURE:
<221> NAME/KEY: MISC_FEATURE
<223> OTHER INFORMATION: Linker7[GSPGSSSSSS(G)a, (a=0 or 1)], example1,
      when a=1

<400> SEQUENCE: 72

Gly Ser Pro Gly Ser Ser Ser Ser Ser Ser Gly
1               5                   10

<210> SEQ ID NO 73
<211> LENGTH: 22
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example1, when a=1and b=1 and c=1

<400> SEQUENCE: 73

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 74
<211> LENGTH: 22
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example2, when a=1and b=1 and c=1

<400> SEQUENCE: 74

Gly Gly Ser Gly Ser Ser Lys Ser Cys Asp Lys Thr His Thr Cys Pro
1               5                   10                  15
```

Pro Cys Pro Ala Pro Glu
            20

<210> SEQ ID NO 75
<211> LENGTH: 27
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example3, when a=1and b=1 and c=6

<400> SEQUENCE: 75

Gly Gly Pro Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 76
<211> LENGTH: 27
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example4, when a=1and b=1 and c=6

<400> SEQUENCE: 76

Gly Gly Ser Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 77
<211> LENGTH: 29
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example5, when a=1and b=1 and c=8

<400> SEQUENCE: 77

Gly Gly Pro Gly Ser Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 78
<211> LENGTH: 29
<212> TYPE: PRT
<213> ORGANISM: Artificial Sequence
<220> FEATURE:
<223> OTHER INFORMATION: page 32, Linker8,
      [GG(P/S)a(GS)b(G/S)cKSCDKTHTCPPCPAPE; (a=0 or 1; b=0-8; c=0-8)]
<220> FEATURE:
<221> NAME/KEY: MISC_FEATURE
<223> OTHER INFORMATION: Linker8 [GG(P/S)a(GS)b(G/S)cKSCDKTHTCPPCPAPE;
      (a=0 or 1; b=0-8; c=0-8)], example6, when a=1and b=1 and c=8

-continued

```
<400> SEQUENCE: 78

Gly Gly Ser Gly Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 79
<211> LENGTH: 24
<212> TYPE: PRT
<213> ORGANISM: Artificial Sequence
<220> FEATURE:
<223> OTHER INFORMATION: page 32, Linker9,
      [GG(P/S)a(GSSGS)bGS(G/S)cDKTHTCPPCPAPE; (a=0 or 1; b=0-8; c=0-8)]
<220> FEATURE:
<221> NAME/KEY: MISC_FEATURE
<223> OTHER INFORMATION: Linker9 [GG(P/S)a(GSSGS)bGS(G/S)cDKTHTCPPCPAPE;
      (a=0 or 1; b=0-8; c=0-8)], example1, when a=1 and b=1 and c=1

<400> SEQUENCE: 79

Gly Gly Pro Gly Ser Ser Gly Ser Gly Ser Ser Asp Lys Thr His Thr
1               5                   10                  15

Cys Pro Pro Cys Pro Ala Pro Glu
            20

<210> SEQ ID NO 80
<211> LENGTH: 23
<212> TYPE: PRT
<213> ORGANISM: Artificial Sequence
<220> FEATURE:
<223> OTHER INFORMATION: page 32, Linker9,
      [GG(P/S)a(GSSGS)bGS(G/S)cDKTHTCPPCPAPE; (a=0 or 1; b=0-8; c=0-8)]
<220> FEATURE:
<221> NAME/KEY: MISC_FEATURE
<223> OTHER INFORMATION: Linker9 [GG(P/S)a(GSSGS)bGS(G/S)cDKTHTCPPCPAPE;
      (a=0 or 1; b=0-8; c=0-8)], example1, when a=1 and b=1 and c=0

<400> SEQUENCE: 80

Gly Gly Pro Gly Ser Ser Gly Ser Gly Ser Asp Lys Thr His Thr Cys
1               5                   10                  15

Pro Pro Cys Pro Ala Pro Glu
            20

<210> SEQ ID NO 81
<211> LENGTH: 21
<212> TYPE: PRT
<213> ORGANISM: Artificial Sequence
<220> FEATURE:
<223> OTHER INFORMATION: page 32, Linker10,
      [GG(P/S)a(S)b(GS)c(G/S)dDKTHTCPPCPAPE; (a=0 or 1; b=0-8; c=0-8;
      d=0-8)]
<220> FEATURE:
<221> NAME/KEY: MISC_FEATURE
<223> OTHER INFORMATION: Linker10 [GG(P/S)a(S)b(GS)c(G/S)dDKTHTCPPCPAPE;
      (a=0 or 1; b=0-8; c=0-8; d=0-8)], example1, when a=1and b=3 and
      c=1 and d=0

<400> SEQUENCE: 81

Gly Gly Pro Ser Ser Ser Gly Ser Asp Lys Thr His Thr Cys Pro Pro
1               5                   10                  15

Cys Pro Ala Pro Glu
            20

<210> SEQ ID NO 82
<211> LENGTH: 25
<212> TYPE: PRT
<213> ORGANISM: Artificial Sequence
```

```
<220> FEATURE:
<223> OTHER INFORMATION: page 32, Linker10,
      [GG(P/S)a(S)b(GS)c(G/S)dDKTHTCPPCPAPE; (a=0 or 1; b=0-8; c=0-8;
      d=0-8)]
<220> FEATURE:
<221> NAME/KEY: MISC_FEATURE
<223> OTHER INFORMATION: Linker10 [GG(P/S)a(S)b(GS)c(G/S)dDKTHTCPPCPAPE;
      (a=0 or 1; b=0-8; c=0-8; d=0-8)], example2, when a=1and b=7 and
      c=1 and d=0

<400> SEQUENCE: 82

Gly Gly Ser Ser Ser Ser Ser Ser Ser Gly Ser Asp Lys Thr His
1               5                   10                  15

Thr Cys Pro Pro Cys Pro Ala Pro Glu
            20                  25

<210> SEQ ID NO 83
<211> LENGTH: 11
<212> TYPE: PRT
<213> ORGANISM: Artificial Sequence
<220> FEATURE:
<223> OTHER INFORMATION: page 34, Linker11, [(S)a(GS)bG(S)c; (a,b=0,1-6;
      c=0 or 1)]
<220> FEATURE:
<221> NAME/KEY: MISC_FEATURE
<223> OTHER INFORMATION: Linker11 [(S)a(GS)bG(S)c; (a,b=0,1-6; c=0 or
      1)], example1, when a=1and b=5 and c=1

<400> SEQUENCE: 83

Ser Gly Ser Gly Ser Gly Ser Gly Ser Gly Ser
1               5                   10

<210> SEQ ID NO 84
<211> LENGTH: 12
<212> TYPE: PRT
<213> ORGANISM: Artificial Sequence
<220> FEATURE:
<223> OTHER INFORMATION: page 34, Linker11, [(S)a(GS)bG(S)c; (a,b=0,1-6;
      c=0 or 1)]
<220> FEATURE:
<221> NAME/KEY: MISC_FEATURE
<223> OTHER INFORMATION: Linker11 [(S)a(GS)bG(S)c; (a,b=0,1-6; c=0 or
      1)], example2, when a=6and b=2 and c=1

<400> SEQUENCE: 84

Ser Ser Ser Ser Ser Ser Gly Ser Gly Ser Gly Ser
1               5                   10

<210> SEQ ID NO 85
<211> LENGTH: 16
<212> TYPE: PRT
<213> ORGANISM: Artificial Sequence
<220> FEATURE:
<223> OTHER INFORMATION: page 34, Linker11, [(S)a(GS)bG(S)c; (a,b=0,1-6;
      c=0 or 1)]
<220> FEATURE:
<221> NAME/KEY: MISC_FEATURE
<223> OTHER INFORMATION: Linker11 [(S)a(GS)bG(S)c; (a,b=0,1-6; c=0 or
      1)], example3, when a=6 and b=5 and c=1

<400> SEQUENCE: 85

Ser Ser Ser Ser Ser Ser Gly Ser Gly Ser Gly Ser Gly Ser Gly Ser
1               5                   10                  15

<210> SEQ ID NO 86
<211> LENGTH: 11
<212> TYPE: PRT
<213> ORGANISM: Artificial Sequence
<220> FEATURE:
<223> OTHER INFORMATION: page 34, Linker12, [S(GGGS)aGb(S)c; (a,b=0,1-6;
```

```
           c=0 or 1)]
<220> FEATURE:
<221> NAME/KEY: MISC_FEATURE
<223> OTHER INFORMATION: Linker12 [S(GGGS)aGb(S)c; (a,b=0,1-6; c=0 or
      1)], example1, when a=2 and b=1 and c=1

<400> SEQUENCE: 86

Ser Gly Gly Gly Ser Gly Gly Gly Ser Gly Ser
1               5                   10

<210> SEQ ID NO 87
<211> LENGTH: 14
<212> TYPE: PRT
<213> ORGANISM: Artificial Sequence
<220> FEATURE:
<223> OTHER INFORMATION: page 35, Linker13, [DKTHTCPGSS(GS)aG(S)b; (a=0,
      1-6; b=0 or 1)]
<220> FEATURE:
<221> NAME/KEY: MISC_FEATURE
<223> OTHER INFORMATION: Linker13 [DKTHTCPGSS(GS)aG(S)b; (a=0,1-6; b=0
      or 1)], example1, when a=1 and b=1

<400> SEQUENCE: 87

Asp Lys Thr His Thr Cys Pro Gly Ser Ser Gly Ser Gly Ser
1               5                   10

<210> SEQ ID NO 88
<211> LENGTH: 12
<212> TYPE: PRT
<213> ORGANISM: Artificial Sequence
<220> FEATURE:
<223> OTHER INFORMATION: page 35, Linker14, [DKTHTCPGSSaG(S)b; (a=0,1-6;
      b=0 or 1)]
<220> FEATURE:
<221> NAME/KEY: MISC_FEATURE
<223> OTHER INFORMATION: Linker14 [DKTHTCPGSSaG(S)b; (a=0,1-6; b=0 or
      1)], example1, when a=1 and b=1

<400> SEQUENCE: 88

Asp Lys Thr His Thr Cys Pro Gly Ser Ser Gly Ser
1               5                   10

<210> SEQ ID NO 89
<211> LENGTH: 15
<212> TYPE: PRT
<213> ORGANISM: Artificial Sequence
<220> FEATURE:
<223> OTHER INFORMATION: page 35, Linker15, [DKTHTC(GSSGS)aGSG(S)b;
      (a=0,1-6; b=0 or 1)]
<220> FEATURE:
<221> NAME/KEY: MISC_FEATURE
<223> OTHER INFORMATION: Linker15 [DKTHTC(GSSGS)aGSG(S)b; (a=0,1-6; b=0
      or 1)], example1, when a=1 and b=1

<400> SEQUENCE: 89

Asp Lys Thr His Thr Cys Gly Ser Ser Gly Ser Gly Ser Gly Ser
1               5                   10                  15

<210> SEQ ID NO 90
<211> LENGTH: 13
<212> TYPE: PRT
<213> ORGANISM: Artificial Sequence
<220> FEATURE:
<223> OTHER INFORMATION: page 35, Linker16, [DKTHTCGSS(GS)aG(S)b;
      (a=0,1-6; b=0 or 1)]
<220> FEATURE:
<221> NAME/KEY: MISC_FEATURE
<223> OTHER INFORMATION: Linker16 [DKTHTCGSS(GS)aG(S)b; (a=0,1-6; b=0 or
      1)], example1, when a=1 and b=1

<400> SEQUENCE: 90
```

Asp Lys Thr His Thr Cys Gly Ser Ser Gly Ser Gly Ser
1               5                   10

<210> SEQ ID NO 91
<211> LENGTH: 11
<212> TYPE: PRT
<213> ORGANISM: Artificial Sequence
<220> FEATURE:
<223> OTHER INFORMATION: page 35, Linker17, [DKTHTCGSSaG(S)b; (a=0,1-6;
      b=0 or 1)]
<220> FEATURE:
<221> NAME/KEY: MISC_FEATURE
<223> OTHER INFORMATION: Linker17 [DKTHTCGSSaG(S)b; (a=0,1-6; b=0 or
      1)], example1, when a=1 and b=1

<400> SEQUENCE: 91

Asp Lys Thr His Thr Cys Gly Ser Ser Gly Ser
1               5                   10

<210> SEQ ID NO 92
<211> LENGTH: 14
<212> TYPE: PRT
<213> ORGANISM: Artificial Sequence
<220> FEATURE:
<223> OTHER INFORMATION: page 35, Linker18, [DKTHTC(GSSGS)aGS(G)b; (a=0,
      1-6; b=0 or 1)]
<220> FEATURE:
<221> NAME/KEY: MISC_FEATURE
<223> OTHER INFORMATION: Linker18 [DKTHTC(GSSGS)aGS(G)b; (a=0,1-6; b=0
      or 1)], example1, when a=1 and b=1

<400> SEQUENCE: 92

Asp Lys Thr His Thr Cys Gly Ser Ser Gly Ser Gly Ser Gly
1               5                   10

<210> SEQ ID NO 93
<211> LENGTH: 20
<212> TYPE: PRT
<213> ORGANISM: Artificial Sequence
<220> FEATURE:
<223> OTHER INFORMATION: page 35, Linker19, [DKTHTCPPCPGSSGSGSGS(G)b;
      (b=0 or 1)]
<220> FEATURE:
<221> NAME/KEY: MISC_FEATURE
<223> OTHER INFORMATION: Linker19 [DKTHTCPPCPGSSGSGSGS(G)b; (b=0 or 1)],
      example1, when a=1 and b=1

<400> SEQUENCE: 93

Asp Lys Thr His Thr Cys Pro Pro Cys Pro Gly Ser Ser Gly Ser Gly
1               5                   10                  15

Ser Gly Ser Gly
            20

<210> SEQ ID NO 94
<211> LENGTH: 18
<212> TYPE: PRT
<213> ORGANISM: Artificial Sequence
<220> FEATURE:
<223> OTHER INFORMATION: PAGE 35, LINKER20, [DKTHTCPPCP(GSSGS)AGS(G)B;
      (A=0, 1-6; B=0 OR 1)]
<220> FEATURE:
<221> NAME/KEY: MISC_FEATURE
<223> OTHER INFORMATION: Linker20 [DKTHTCPPCP(GSSGS)aGS(G)b; (a=0, 1-6;
      b=0 or 1)], example1, when a=1 and b=1

<400> SEQUENCE: 94

Asp Lys Thr His Thr Cys Pro Pro Cys Pro Gly Ser Ser Gly Ser Gly
1               5                   10                  15

```
Ser Gly

<210> SEQ ID NO 95
<211> LENGTH: 22
<212> TYPE: PRT
<213> ORGANISM: Artificial Sequence
<220> FEATURE:
<223> OTHER INFORMATION: page 35, Linker21, [DKTHTCPPCPGSS(GS)aGS(G)b;
      (a=0, 1-6; b=0 or 1)]
<220> FEATURE:
<221> NAME/KEY: MISC_FEATURE
<223> OTHER INFORMATION: Linker21 [DKTHTCPPCPGSS(GS)aGS(G)b; (a=0, 1-6;
      b=0 or 1)], example1, when a=3 and b=1

<400> SEQUENCE: 95

Asp Lys Thr His Thr Cys Pro Pro Cys Pro Gly Ser Ser Gly Ser Gly
1               5                   10                  15

Ser Gly Ser Gly Ser Gly
            20

<210> SEQ ID NO 96
<211> LENGTH: 16
<212> TYPE: PRT
<213> ORGANISM: Artificial Sequence
<220> FEATURE:
<223> OTHER INFORMATION: page 35, Linker22, [DKTHTCPPCPGSSaGS(G)b; (a=0,
      1-6; b=0 or 1)]
<220> FEATURE:
<221> NAME/KEY: MISC_FEATURE
<223> OTHER INFORMATION: Linker22 [DKTHTCPPCPGSSaGS(G)b; (a=0,1-6; b=0
      or 1)], example1, when a=1 and b=1

<400> SEQUENCE: 96

Asp Lys Thr His Thr Cys Pro Pro Cys Pro Gly Ser Ser Gly Ser Gly
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: page 33, table 2
<220> FEATURE:
<221> NAME/KEY: MISC_FEATURE
<223> OTHER INFORMATION: FC01_linker [(G)GSPGSSSSSSGSDKTH]

<400> SEQUENCE: 97

Gly Gly Ser Pro Gly Ser Ser Ser Ser Ser Ser Gly Ser Asp Lys Thr
1               5                   10                  15

His

<210> SEQ ID NO 98
<211> LENGTH: 15
<212> TYPE: PRT
<213> ORGANISM: Artificial Sequence
<220> FEATURE:
<223> OTHER INFORMATION: page 33, table 2
<220> FEATURE:
<221> NAME/KEY: MISC_FEATURE
<223> OTHER INFORMATION: FC02_linker [(G)GSPGSSSSGSDKTH]

<400> SEQUENCE: 98

Gly Gly Ser Pro Gly Ser Ser Ser Ser Gly Ser Asp Lys Thr His
1               5                   10                  15

<210> SEQ ID NO 99
<211> LENGTH: 13
<212> TYPE: PRT
```

```
<213> ORGANISM: Artificial Sequence
<220> FEATURE:
<223> OTHER INFORMATION: page 33, table 2
<220> FEATURE:
<221> NAME/KEY: MISC_FEATURE
<223> OTHER INFORMATION: FC03_linker [(G)GSPGSSGSDKTH]

<400> SEQUENCE: 99

Gly Gly Ser Pro Gly Ser Ser Gly Ser Asp Lys Thr His
1               5                   10

<210> SEQ ID NO 100
<211> LENGTH: 11
<212> TYPE: PRT
<213> ORGANISM: Artificial Sequence
<220> FEATURE:
<223> OTHER INFORMATION: page 33, table 2
<220> FEATURE:
<221> NAME/KEY: MISC_FEATURE
<223> OTHER INFORMATION: FC04_linker [(G)GSPGSSDKTH]

<400> SEQUENCE: 100

Gly Gly Ser Pro Gly Ser Ser Asp Lys Thr His
1               5                   10

<210> SEQ ID NO 101
<211> LENGTH: 7
<212> TYPE: PRT
<213> ORGANISM: Artificial Sequence
<220> FEATURE:
<223> OTHER INFORMATION: page 33, line 9
<220> FEATURE:
<221> NAME/KEY: MISC_FEATURE
<223> OTHER INFORMATION: flexible linker element connecting Fc-domain
      with a C-terminal Strep-Tag-II

<400> SEQUENCE: 101

Ser Ser Ser Ser Ser Ser Ala
1               5

<210> SEQ ID NO 102
<211> LENGTH: 8
<212> TYPE: PRT
<213> ORGANISM: Artificial Sequence
<220> FEATURE:
<223> OTHER INFORMATION: page 33, line 9
<220> FEATURE:
<221> NAME/KEY: MISC_FEATURE
<223> OTHER INFORMATION: Strep-tag-II sequence

<400> SEQUENCE: 102

Trp Ser His Pro Gln Phe Glu Lys
1               5

<210> SEQ ID NO 103
<211> LENGTH: 12
<212> TYPE: PRT
<213> ORGANISM: Artificial Sequence
<220> FEATURE:
<223> OTHER INFORMATION: page 30, line 24, Linker
<220> FEATURE:
<221> NAME/KEY: MISC_FEATURE
<223> OTHER INFORMATION: Linker

<400> SEQUENCE: 103

Gly Gly Gly Ser Gly Gly Gly Ser Gly Gly Gly Ser
1               5                   10
```